US011981934B2

(12) United States Patent
Fiedler et al.

(10) Patent No.: US 11,981,934 B2
(45) Date of Patent: May 14, 2024

(54) ADENO-ASSOCIATED VIRUS PURIFICATION METHODS

(71) Applicant: TAKEDA PHARMACEUTICAL COMPANY LIMITED, Osaka (JP)

(72) Inventors: Christian Fiedler, Vienna (AT); Meinhard Hasslacher, Vienna (AT); Jadranka Koehn, Laupheim (DE)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 758 days.

(21) Appl. No.: 16/958,974

(22) PCT Filed: Dec. 27, 2018

(86) PCT No.: PCT/US2018/067627
§ 371 (c)(1),
(2) Date: Jun. 29, 2020

(87) PCT Pub. No.: WO2019/133677
PCT Pub. Date: Jul. 4, 2019

(65) Prior Publication Data
US 2020/0332266 A1    Oct. 22, 2020

Related U.S. Application Data

(60) Provisional application No. 62/611,709, filed on Dec. 29, 2017.

(51) Int. Cl.
| | | |
|---|---|---|
| C07K 14/435 | (2006.01) | |
| A61K 38/00 | (2006.01) | |
| B01D 15/16 | (2006.01) | |
| B01D 15/36 | (2006.01) | |
| B01D 15/38 | (2006.01) | |
| B01D 15/42 | (2006.01) | |
| C07K 14/705 | (2006.01) | |
| C07K 16/28 | (2006.01) | |
| C12N 7/00 | (2006.01) | |
| G01N 33/569 | (2006.01) | |

(52) U.S. Cl.
CPC ............ *C12N 7/00* (2013.01); *B01D 15/166* (2013.01); *B01D 15/363* (2013.01); *B01D 15/3809* (2013.01); *B01D 15/426* (2013.01); *G01N 33/56983* (2013.01); *C12N 2750/14151* (2013.01); *G01N 2333/075* (2013.01)

(58) Field of Classification Search
CPC .. C07K 14/705; C07K 2317/76; A61K 38/00; B01D 15/3804; C12N 2750/14151
See application file for complete search history.

(56) References Cited

U.S. PATENT DOCUMENTS

| | | |
|---|---|---|
| 4,543,363 A | 9/1985 | Yanagihara |
| 2003/0207439 A1 | 11/2003 | Wright et al. |
| 2015/0275195 A1 | 10/2015 | Godawat et al. |

FOREIGN PATENT DOCUMENTS

| | | |
|---|---|---|
| CN | 104232687 | 12/2014 |
| JP | 2003512834 | 4/2003 |
| RU | 2588387 | 6/2016 |
| WO | 200075195 | 12/2000 |
| WO | 200130983 | 5/2001 |
| WO | 200212455 | 2/2002 |
| WO | 2010148143 | 12/2010 |
| WO | 2016128408 A1 | 8/2016 |
| WO | 2017100676 | 6/2017 |
| WO | 2017160360 | 9/2017 |
| WO | 2021101987 | 5/2021 |

OTHER PUBLICATIONS

Sep. 16, 2021 Extended European Search Report mailed in connection with EPO No. 18895008.
Arnold et al., "Metabolic Biotinylation Provides a Unique Platform for the Purification and Targeting of Multiple AAV Vector Serotypes" Molecular Therapy, Elsevier Inc. US, vol. 14, No. 1, Jul. 1, 2006, pp. 97-106.
International Search Report dated Mar. 14, 2019 in connection with PCT/US2018/067627.
Wright et al. "Identification of factors that contribute to recombinant AAV2 particle aggregation and methods to prevent its occurrence during vector purification and formulation,"Mol Ther, Jul. 1, 2005 (Jul. 1, 2005), vol. 12, No. 1 pp. 171-178.
Chahal et al. "Primary recovery and chromatographic purification of adeno-associated virus type 2 produced by baculovirus/insect cell system,"J Virol Methods, Oct. 20, 2006 (Oct. 20, 2006), vol. 139, No. 1, pp. 61-70.
Yu et al. "Interaction between various polymerized human albumins and hepatitis B surface antigen,"J Virol, Sep. 1, 1985 (Sep. 1, 1985), vol. 55, No. 3, pp. 736-743.
Tsumoto et al., "Effects of Salts on Protein-Surface Interactions: Applications for Column Chromatography", Journal of Pharmaceutical Sciences, vol. 96, No. 7, Jul. 2007, pp. 1677-1690.
Shiyama et al., "Design and synthesis of novel hydrophilic spacers for the reduction of nonspecific binding proteins on affinity resins" Bioogranic & Medicinal Chemistry, 12 (2004) 2831-2841.
POROS® 20 HS, SP, S, and CM, Perfusion Chromatography®, Bulk Media for Cation Exchange Chromatography, Operating Instructions.
Office Action dated Oct. 25, 2022 in connection with Japanese Patent Application No. 2020-536656.

(Continued)

*Primary Examiner* — Barry A Chestnut

(74) *Attorney, Agent, or Firm* — Troutman Pepper Hamilton Sanders LLP

(57) ABSTRACT

Provided herein are methods of producing an adeno-associated virus (AAV) product and methods of purifying adeno-associated virus. AAV is loaded onto an affinity resin, wash steps are undertaken, and AAV is eluted from the affinity resin. Various buffers are disclosed for use in the wash steps and elution.

29 Claims, 39 Drawing Sheets

(56) References Cited

OTHER PUBLICATIONS

Office Action and Search Report dated Feb. 8, 2022 in connection with Russian Patent Application No. 2020124946.
Office Action dated May 30, 2023 in connection with Chinese Patent Application No. 201880087932.0.
Weihong Qu et al., "Research Progress in Adeno-associated Virus Vector Purification Technology", China Pharmacy, vol. 26 (34), pp. 133-137 (2015).

SDS PAGE 12% Anti AAV Western Blot

Lane 1: Marker Precision plus Dual Color
Lane 2: AAV8 reference 130ng/Lane [ 60µg/ml AAV8 ]
Lane 3: Blank
Lane 4: Affinity eluate according to Shire Procedure [ 190µg/ml AAV8 Antigen ]
Lane 5: Blank
Lane 6: Affinity eluate according Procedure 2 [ 190µg/ml AAV8 Antigen ]

NuPAGE 4-12% Bis-Tris Midi Gel 1.0mm, 20 well Cat.Nr. WG1402BX10
MES SDS Running Buffer, Invitrogen, Cat.Nr. NP0002
SB+DTT Incubation 10min bei 70°C.10min cool down JAA treatment 1st Antibody: Mab to VP1, VP2 and VP3 of AAV (Adeno-Associated Virus)
  Protein A affinity chromatography
  PROGEN61058
2nd Antibody: GOAT anti Mouse ALP
  SIGMA A4656 1:2000 1h

FIG. 3

ADENO-ASSOCIATED VIRUS PURIFICATION METHODS

CROSS-REFERENCE TO RELATED APPLICATIONS

This application is a U.S. National Phase of International Patent Application No. PCT/US2018/067627, filed on Dec. 27, 2018, which claims priority to U.S. Provisional Application No. 62/611,709, filed on Dec. 29, 2017, the disclosures of which are each herein incorporated by reference in their entirety.

TECHNICAL FIELD

The invention relates to materials and methods of purifying adeno-associated virus (AAV).

BACKGROUND

Adeno-associated virus (AAV) is a small, non-enveloped virus that packages a linear single-stranded DNA genome. AAV belongs to the family Parvoviridae and the genus Dependovirus, since productive infection by AAV occurs only in the presence of a helper virus, such as, for example, adenovirus or herpes virus. Even in the absence of a helper virus, AAV (serotype 2) can achieve latency by integrating into chromosome 19q13.4 of a host human genome. It is the only mammalian DNA virus known to be capable of site-specific integration (Daya and Berns, Clinical Microbiology Reviews, pages 583-593 (2008)).

For AAV to be safely used in the clinic, AAV has been genetically modified at several locations within its genome. For example, the Rep gene, which is required for viral replication, and the element required for site-specific integration have been eliminated from the AAV genome in many viral vectors. Such recombinant AAV (rAAV) exist in an extrachromosomal state and have very low integration efficiency into the genomic DNA. The possibility of rAAV inducing random mutagenesis in a host cell is thus reduced, if not eliminated altogether. Because of these properties and the lack of pathogenicity, rAAV has shown great promise as a gene therapy vector in multiple aspects of pre-clinical and clinical applications. New serotypes and self-complementary vectors are being tested in the clinic. Alongside these ongoing vector developments, continued effort has focused on scalable manufacturing processes that can efficiently generate high titer quantities of rAAV vectors with high purity and potency.

Though the effort to design efficient, large-scale methods to purify an AAV product suitable for human administration has been great, there remains a need for better AAV purification methods. There are various other proteins and materials from the host cell culture matrix that could be more efficiently removed during the purification of AAV. AAV purification methods which include steps for removing host cell material from the final AAV product are therefore desired.

SUMMARY

A feature of AAV vector generation in cell culture is the formation of a complex matrix that comprises material from disrupted cells. In particular, host cell proteins, proteasomes, cell debris and potential virus-specific receptors are often present in the material from disrupted cells. The disclosed methods which include steps for removing host cell material from the final AAV product in conditions that result in greater purity at a physiologically applicable pH.

In one aspect is provided a method of purifying an adeno-associated virus (AAV) comprising
 (a) loading an AAV containing solution onto an affinity resin targeted against AAV under conductions that allow binding between the AAV in the solution and the affinity resin;
 (b) undertaking at least two wash steps; and
 (c) eluting the AAV from the affinity resin.

In some embodiments, the method further comprises contacting the AAV containing solution with an anion exchanger and eluting the AAV containing solution from the anion exchanger prior to loading the AAV containing solution onto the affinity resin.

In some embodiments, at least one of the wash steps comprises applying to the affinity resin a buffer comprising an organic solvent or detergent. In some embodiments, the buffer comprises TrisHCl and a salt. In some embodiments, the buffer comprises one or more of Histidine, Histidine-HCl, Arginine-HCl, Lysine-HCl, Glycine, Taurine, MES-Na, Bis-Tris, and N-acetyl-D,L-tryptophan. In some embodiments, the salt is NaCl. In some embodiments, the buffer comprises sodium acetate. In some embodiments, the buffer comprises magnesium chloride. In some embodiments, the buffer comprises TrisHCl and ethylene glycol. In some embodiments, the buffer comprises Arginine-HCl and one of sucrose and glycerol. In some embodiments, the buffer comprises Taurine and ethylene glycol. In some embodiments, the buffer comprises Arginine-HCl, Lysine-HCl, and Histidine-HCl. In some embodiments, the buffer comprises TrisHCl and DMSO.

In some embodiments, at least three wash steps are performed. In some embodiments, three wash steps are performed. In some embodiments, the three wash steps are performed in succession.

In some embodiments, the organic solvent or detergent is polysorbate 80, ethylene glycol, sorbitol, mannitol, xylitol, DMSO, sucrose, or trehalose. In some embodiments, the detergent comprises one or more of Triton X100, polysorbate 80, and tri (n-butyl) phosphate (TNBP). In some embodiments, the buffer comprises Bis-Tris.

In some embodiments, the first wash step comprises applying to the affinity resin a first buffer comprising from about 50 to about 2000 mM sodium acetate and from about 0.05 to about 0.2% polysorbate 80, and the first buffer has a pH from about 5.2 to about 6.8;
 the second wash step comprises applying to the affinity resin a second buffer comprising from about 30 to about 200 mM TrisHCl and from about 75 to about 500 mM salt, and the second buffer has a pH from about 7.5 to about 9.2; and
 the third wash step comprises applying to the affinity resin a third buffer comprising from about 30 to about 200 mM TrisHCl and from about 30 to about 75 vol % ethylene glycol, and the third buffer has a pH from about 7.3 to about 8.8.

In some embodiments, a first wash step comprises applying to the affinity resin a first buffer comprising from about 50 to about 500 mM sodium salt of 2-(N-morpholino) ethanesulfonic acid (MES-Na), from about 3 to about 30 mM EDTA, and a solvent/detergent mixture comprising polysorbate 80, DMSO and tri(n-butyl)phosphate (TNBP), and the first buffer has a pH from about 5.2 to about 6.8;
 the second wash step comprises applying to the affinity resin a second buffer comprising from about 30 to about 200 mM TrisHCl or Arginine-HCl and from about 75 to about 500 mM salt, and the second buffer has a pH from about 7.5 to about 9.2; and the third wash step comprises applying to the affinity resin a third buffer comprising from about 20 to about 80 mM Arginine-HCl and from about 50 to about 200 mM salt, and the third buffer has a pH from about 7.3 to about 8.8.

In some embodiments, the first wash step comprises applying to the affinity resin a first buffer comprising from about 50 to about 200 mM taurine, and 0.2 to 1.5% PEG (e.g., PEG 6000), where the first buffer has a pH from about 5.2 to about 6.8;

the second wash step comprises applying to the affinity resin a second buffer comprising from about 30 to about 300 mM glycine, and the second buffer has a pH from about 7.5 to about 9.2; and the third wash step comprises applying to the affinity resin a third buffer comprising from about 20 to about 150 mM taurine, from about 30 to about 75 vol % ethylene glycol, and from 0.05 to 0.2% octylglycopyranoside, and the third buffer has a pH from about 7.3 to about 8.8.

In some embodiments, the first wash step comprises applying to the affinity resin a first buffer comprising from about 80 to about 400 mM Bis-Tris, and about 10 to about 20 grams of a solvent/detergent mixture comprising about Triton-X100, polysorbate 80 and TNBP in a ratio of about 11:3:3 (by weight), where the first buffer has a pH from about 5.2 to about 6.8;

the second wash step comprises applying to the affinity resin a second buffer comprising from about 5 to about 20 mmol sodium citrate, and where the second buffer has a pH from about 7.5 to about 9.2; and the third wash step comprises applying to the affinity resin a third buffer comprising from about 50 to about 200 mM Arginine-HCl, from about 50 to about 200 mM Lysine HCl, from about 50 to about 200 mM Histidine-HCl, and from about 1 mM to about 4 mM N-acetyl-D,L-tryptophan, and about 10% to about 40% (w/w) polysorbate 80, and where the third buffer has a pH from about 7.3 to about 8.8.

In some embodiments, the first wash step comprises applying to the affinity resin a first buffer comprising from about 50 nM to about 200 mM NaAcetate and from about 0.05 to about 0.2% Polysorbate80, where the first buffer has a pH of about 5.2 to about 6.8;

the second wash step comprises applying to the affinity resin a second buffer comprising from about 20 nM to about 100 mM TrisHCl and from about 50 nM to about 200 nM of salt, where the second buffer has a pH of about 7.5 to about 8.8; and the third wash step comprises applying to the affinity resin a third buffer comprising about 20 mM to 100 mM TrisHCl, from about 40% to about 60% (w/w) ethylene glycol, and where the third buffer has a pH from about 7.5 to about 8.8.

In some embodiments, the first wash step comprises applying to the affinity resin a first buffer comprising from about 50 nM to about 200 mM NaAcetate and from about 0.05 to about 0.2% Polysorbate80, where the first buffer has a pH of about 5.2 to about 6.8;

the second wash step comprises applying to the affinity resin a second buffer comprising from about 20 nM to about 100 mM TrisHCl and from about 50 nM to about 200 nM of salt, where the second buffer has a pH of about 7.5 to about 8.8; and the third wash step comprises applying to the affinity resin a third buffer comprising about 20 mM to 100 mM TrisHCl, from about 40% to about 60% (w/w) ethylene glycol, and the third buffer has a pH from about 7.5 to about 8.8.

In some embodiments, the salt is selected from NaC, KCl, $MgCl_2$, $CaCl_2$), Sodium Citrate, LiC, CsCl, Sodium Acetate, and a combination of one or more of NaCl, KCl, $MgCl_2$, $CaCl_2$), Sodium Citrate, LiCl, CsCl, and Sodium Acetate. In some embodiments, the salt is NaCl.

In some embodiments, the concentration of the salt does not exceed 500 mM. In some embodiments, the concentration of the salt does not exceed 200 mM. In some embodiments, the concentration of salt in the third buffer does not exceed 500 mM. In some embodiments, the concentration of salt in the third buffer does not exceed 200 mM.

In some embodiments, the method further comprises a fourth wash step that takes place before the first wash step and comprises applying to the affinity resin a fourth buffer comprising from about 10 to about 30 mM TrisHCl and from about 75 to about 250 mM NaCl, and the fourth buffer has a pH from about 6.5 to about 8.0.

In some embodiments, the first buffer comprises about 100 mM sodium acetate, about 0.1% polysorbate 80, and the first buffer has a pH of about 6.0. In some embodiments, the second buffer comprises about 50 mM TrisHCl and about 125 mM NaCl, and the second buffer has a pH of about 8.5. In some embodiments, the third buffer comprises about 50 mM TrisHCl and about 50 vol % ethylene glycol, and the third buffer has a pH of about 8.5.

In some embodiments, the first wash step comprises applying to the affinity resin a first buffer comprising from about 50 to about 200 mM sodium acetate and from about 0.05 to about 0.2% polysorbate 80, and the first buffer has a pH from about 5.5 to about 6.5;

the second wash step comprises applying to the affinity resin a second buffer comprising from about 10 to about 70 mM TrisHCl and from about 75 to about 250 mM NaCl, and the second buffer has a pH from about 8.0 to about 9.0; and the third wash step comprises applying to the affinity resin a third buffer comprising from about 10 to about 70 mM TrisHCl and from about 30 to about 75 vol % ethylene glycol, and the third buffer has a pH from about 8.0 to about 9.0. In some embodiments, the method further comprises a fourth wash step that takes place before the first wash step and comprises applying to the affinity resin a fourth buffer comprising from about 10 to about 30 mM TrisHCl and from about 75 to about 250 mM NaCl, and the fourth buffer has a pH from about 6.5 to about 8.0.

In some embodiments, the first buffer comprises about 100 mM sodium acetate and about 0.1% Polysorbate 80, and the first buffer has a pH of about 6.0. In some embodiments, the second buffer comprises about 50 mM TrisHCl and about 125 mM NaCl, and the second buffer has a pH of about 8.5. In some embodiments, the third buffer comprises about 50 mM TrisHCl and about 50 vol % ethylene glycol, and the third buffer has a pH of about 8.0.

In some embodiments, an acidic component is removed. In some embodiments, the acidic component is host cell DNA, such as HEK293 DNA, and where the acidic component is reduced to a value below 250 pg per microgram of AAV antigen as measured by qPCR. In some embodiments, the acidic component is host cell DNA, such as HEK293 DNA, and where the acidic component is reduced to a value below 250 pg per microgram of AAV antigen as measured by ELISA.

In some embodiments, eluting comprises applying a continuous linear increase of the conductivity of an elution buffer by gradient elution. In some embodiments, eluting comprises applying continuous linear increase of the concentration of an organic solvent by gradient elution. In some embodiments, eluting comprises contacting the affinity resin with an elution buffer comprising ethylene glycol, a salt such as NaCl, and a buffer such as TrisHCl, where the pH is at least 7.0. In some embodiments, the salt concentration is about 750 mM, the buffer concentration is about 50 mM, and the ethylene glycol is 50-60% (w/w). In some embodiments, the pH is about 8.0. In some embodiments, the salt is NaCl and the buffer is TrisHCl.

In some embodiments, eluting comprises contacting the affinity resin with an elution buffer comprising about 750 mM NaCl and 50-60% (w/w) ethylene glycol at a pH of at least 7.0. In some embodiments, the elution buffer comprises at least about 55% (w/w) ethylene glycol. In some embodiments, eluting comprises contacting the affinity resin with an elution buffer comprising about 50 mM Tris HCl, about 750 mM to about 1250 mM NaCl and about 60% (w/w) ethylene glycol at a pH of at least 7.8.

In some embodiments, eluting comprises contacting the affinity resin with an elution buffer comprising about 2 mM magnesium chloride, about 50 mM Arginine-HCl, about 750 mM to about 1000 mM NaCl and at least about 55% (w/w) sucrose at a pH of at least about 8.0.

In some embodiments, eluting further comprises
(a) contacting the affinity resin with a fifth buffer comprising from about 20 to about 100 mM Arginine-HCl and from about 75 to about 250 mM NaCl, and the fifth buffer has a pH from about 7.5 to about 8.5; and
(b) contacting the affinity resin with a second elution buffer comprising from about 20 to about 100 mM Arginine-HCl, from about 40 to about 60% (w/w) glycerol, and from about 500 to 1000 mM salt, and the second elution buffer has a pH from about 7.5 to about 8.5.

In some embodiments, the steps are performed in succession.

In some embodiments, eluting comprises contacting the affinity resin with an elution buffer comprising about 2 mM magnesium chloride, about 50 mM Arginine-HCl, about 750 mM to about 1000 mM NaCl and at least about 50% (w/w) glycerol at a pH of at least about 8.0.

In some embodiments, eluting comprises contacting the affinity resin with an elution buffer comprising about 2 mM magnesium chloride, about 50 mM Taurine, about 600 mM to about 1000 mM NaCl, about 0.05 to about 0.2% octylglycopyranoside, and about 60% (w/w) ethylene glycol at a pH of at least about 7.8. In some embodiments, eluting further comprises
(a) contacting the affinity resin with a fifth buffer comprising from about 20 to about 100 mM Tris-HCl and from about 75 to about 250 mM NaCl, and the fifth buffer has a pH from about 8.0 to about 8.8; and
(b) contacting the affinity resin with a second elution buffer comprising about 1 M ammonium sulfate, about 50 mM Tris HCl, and about 50% (v/v) ethylene glycol at a pH of at least about 6.8.

In some embodiments, the steps are performed in succession.

In some embodiments, eluting comprises contacting the affinity resin with an elution buffer comprising about 1 M ammonium sulfate, about 50 mM Tris HCl, and about 50% (v/v) ethylene glycol at a pH of at least about 6.8. In some embodiments, eluting comprises contacting the affinity resin with an elution buffer comprising about 20% (w/w) sucrose, about 10% (w/w) sorbitol, about 5% (w/w) mannitol or about 5% (w/w) sucrose, about 15% (w/w) glycerol, about 50 mM Histidine, and about 750 to about 1000 mM NaCl at a pH of at least about 7.8.

In some embodiments, eluting further comprises
(a) contacting the affinity resin with a fifth buffer comprising from about 20 to about 100 mM Histidine, from about 80 to about 120 mM NaCl, and the fifth buffer has a pH from about 8.0 to about 8.8; and
(b) contacting the affinity resin with a second elution buffer comprising from about 20 to about 100 mM Histidine, from about 600 to about 900 mM NaCl, and from about 5 to 60% (w/w) DMSO, and the fifth buffer has a pH from about 6.5 to about 8.5.

In some embodiments, the steps are performed in succession. In some embodiments, eluting comprises contacting the affinity resin with an elution buffer comprising about 100 mM Glycine-HCl, about 200 mM NaCl, at a pH of about 2.5.

In some embodiments, the elution buffer is at a pH of about 8.0. In some embodiments, the elution buffer is at a pH of 8.0.

In some embodiments, eluting comprises a stepwise increase of a counter ion concentration. In some embodiments, eluting comprises a stepwise increase of an organic solvent concentration. In some embodiments, the salt in the elution buffer is selected from monovalent, divalent or polyvalent anions, such as chloride, acetate, sulfate, and citrate.

In some embodiments, the first wash step comprises applying to the affinity resin a first buffer comprising from about 50 to about 200 mM sodium acetate, from about 0.05 to about 0.2% Polysorbate80, and the first buffer has a pH from about 5.2 to about 6.8;

the second wash step comprises applying to the affinity resin a second buffer comprising from about 25 to about 100 mM TrisHCl and from about 50 to about 200 mM NaCl, and the second buffer has a pH from about 7.5 to about 9.2; and the third wash step comprises applying to the affinity resin a third buffer comprising from about 20 to about 100 mM TrisHCl and from about 75 to about 250 mM NaCl, and the third buffer has a pH from about 7.5 to about 8.8. In some embodiments, the method further comprises elution by applying to the affinity resin purified water, followed by applying to the affinity resin from about 20 to about 50 mM HCl at a pH from about 1.7 to about 2.5. In some embodiments, the method further comprises elution by applying a gradient of 0 to 100% 20-50 mM Hydrochloric acid/800-1200 mM NaCl in 0.5-2.0 mM Hydrochloric acid.

In some embodiments, the AAV obtained from the eluting step has an HC impurity level of ≤99.9%. In some embodiments, the AAV obtained from the eluting step has an HC impurity level of ≤99.0%.

In some embodiments, the AAV is AAV8, the affinity resin is POROS™ CaptureSelect™ AAV8, and the elution buffer is acidic and does not comprise ethylene glycol. In some embodiments, the AAV is AAV9, the affinity resin is POROS™ CaptureSelect™ AAV9, and the elution buffer is acidic and does not comprise ethylene glycol.

In some embodiments, the AAV is AAV8, and the affinity resin is an immune affinity resin consisting of an immobilized monoclonal antibody against AAV8 from type ADK8 or ADK8/9 immobilized on a chromatography matrix. In some embodiments, the AAV is AAV9, and the affinity resin is an immune affinity resin consisting of an immobilized monoclonal antibody against AAV9 from type ADK9 or ADK8/9 immobilized on a chromatography matrix.

In some embodiments, the method further comprises contacting the AAV containing solution with a filter comprising positively charged groups effective to deplete acidic charged contaminants from the AAV containing solution.

In some embodiments, the method further comprises nanofiltration of an AAV fraction to remove viruses greater than 35 nm.

In some embodiments, the method further comprises a polish step comprising performing AEX chromatography with a column comprising tentacle gel.

In some embodiments, the method further comprises testing an AAV fraction via an AAV-specific ELISA.

In some embodiments, the AAV specific ELISA is a sandwich ELISA specific for AAV.

In another aspect is provided an AAV product produced by a method according to any one of claims 1 to 83.

BRIEF DESCRIPTION OF THE DRAWINGS

FIG. 3 depicts a Western Blot showing more AAV8 present in an eluate prepared according to a purification protocol with multiple wash steps described herein (lane 4) than in an eluate from a comparative purification protocol without the wash steps (lane 6). An AAV8 reference sample is in lane 2.

DETAILED DESCRIPTION

Figure 1:
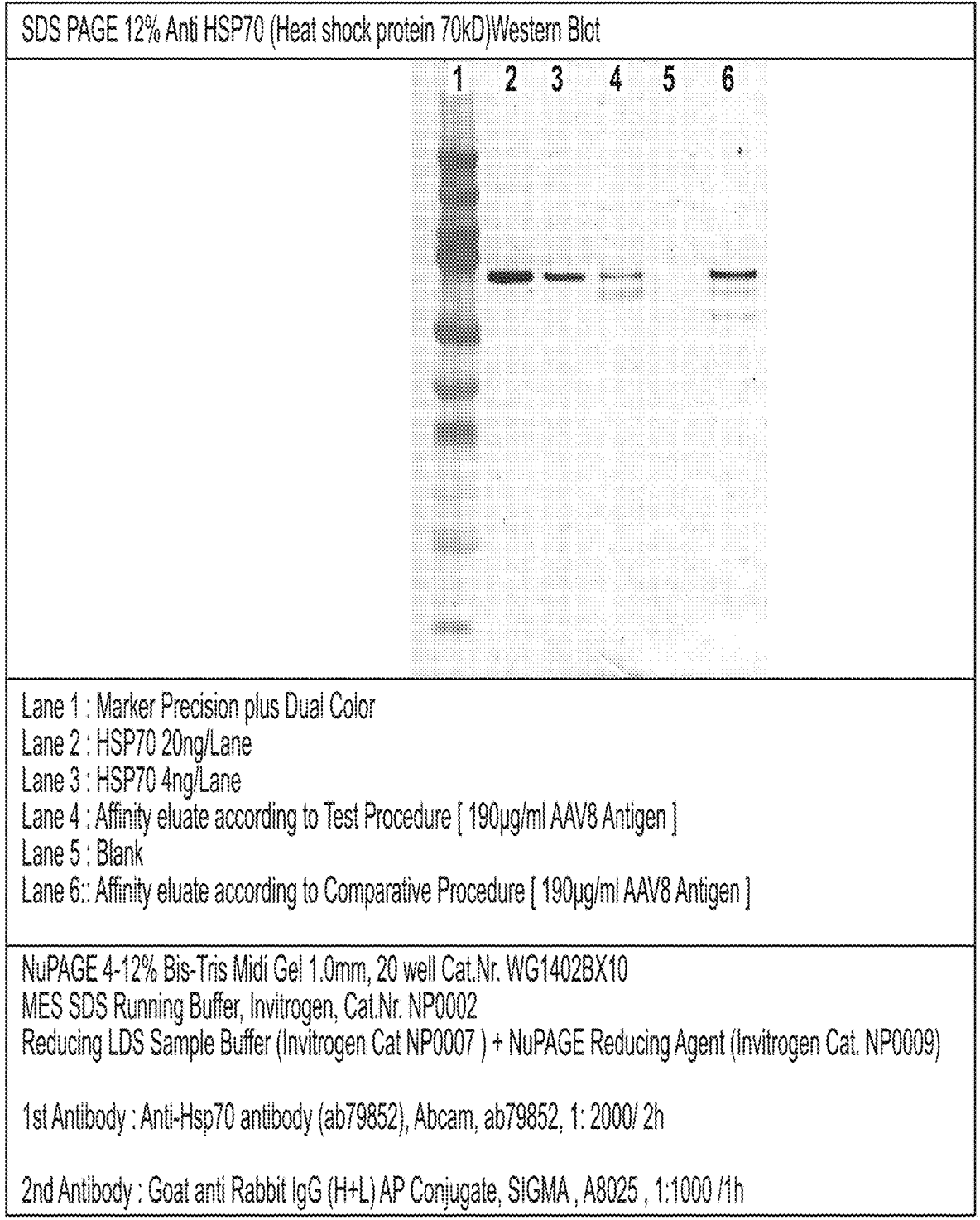
FIG. 1 depicts a Western Blot showing substantially less Heat Shock Protein 70 kDa (HSP70) according to a purification protocol with multiple wash steps described herein (lane 4) as opposed to a comparative purification protocol without the wash steps (lane 6).

Provided herein are methods of producing an adeno-associated virus (AAV) product, methods of purifying AAV, and methods of purifying full AAV capsids from a concentrated AAV fraction comprising empty AAV capsids and full AAV capsids.

The use of the terms "a," "an" and "the", and similar referents in the context of describing the disclosure (especially in the context of the following claims), are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

A feature of AAV vector generation in cell culture is the formation of a complex matrix that comprises material from disrupted cells. In particular, host cell proteins, proteasomes, cell debris and potential virus-specific receptors are often present in the material from disrupted cells. The disclosed methods which include steps for removing host cell material from the final AAV product in conditions that result in greater purity at a physiologically applicable pH.

In one aspect is provided a method of purifying an adeno-associated virus (AAV). The method comprises (a) loading an AAV containing solution onto an affinity resin targeted against AAV under conductions that allow binding between the AAV in the solution and the affinity resin; (b) undertaking at least two wash steps; and (c) eluting the AAV from the affinity resin.

In some embodiments, the AAV purified by the methods described herein are of AAV1 serotype, AAV2 serotype, AAV3 serotype, AAV4 serotype, AAV5 serotype, AAV6 serotype, AAV7 serotype, AAV8 serotype, AAV9 serotype, AAV10 serotype, AAV11 serotype, AAV12 serotype, AAV13 serotype, AAAV serotype, BAAV serotype, AAV (VR-195) serotype, and AAV (VR-355) serotype. In some embodiments, the AAV is modified by genetic engineering and/or is chemically modified.

In some embodiments, the method further comprises contacting the AAV-containing solution with an anion exchanger and eluting the AAV containing solution from the anion exchanger prior to loading the AAV containing solution onto the affinity resin. The anion exchanger may be operated in flow-through mode. In some embodiments, at least one of the wash steps comprises applying to the affinity resin a buffer comprising an organic solvent or detergent. In some embodiments, the buffer comprises TrisHCl and a salt, e.g., NaCl. In some embodiments, the buffer comprises sodium acetate. In some embodiments, the buffer comprises magnesium chloride. In some embodiments, the buffer comprises TrisHCl and ethylene glycol. In some embodiments, the buffer comprises Arginine-HCl and one of sucrose and glycerol. In some embodiments, the buffer comprises Taurine and ethylene glycol. In some embodiments, the buffer comprises Arginine-HCl, Lysine-HCl, and Histidine-HCl. In some embodiments, the buffer comprises TrisHCl and DMSO.

In some embodiments, the buffer comprises Arginine-HCl and a salt, e.g., NaCl. In some embodiments, the buffer comprises histidine and a salt, e.g., NaCl. In some embodiments, the buffer comprises TrisHCl and ethylene glycol. In some embodiments, the organic solvent is ethylene glycol. In some embodiments, the organic solvent is DMSO. In some embodiments, the salt is selected from NaC, KCl, $MgCl_2$, $CaCl_2$, Sodium Citrate, LiCl, CsCl, Sodium Acetate, and a combination of one or more of NaCl, KCl, $MgCl_2$, $CaCl_2$, Sodium Citrate, LiCl, CsCl, and Sodium Acetate. In some embodiments, the concentration of the salt does not exceed 500 mM. In some embodiments, the concentration of the salt does not exceed 200 mM.

In some embodiments, at least three wash steps are performed. In some embodiments, three wash steps are performed. In some embodiments, the three wash steps are performed in succession.

In some embodiments, the organic solvent or detergent is polysorbate 80, ethylene glycol, sorbitol, mannitol, xylitol, DMSO, sucrose, or trehalose. In some embodiments, the detergent comprises one or more of Triton X100, polysorbate 80, and tri (n-butyl) phosphate (TNBP). In some embodiments, the buffer comprises Bis-Tris.

In some embodiments, at least three wash steps are performed; a first wash step comprises applying to the affinity resin a first buffer comprising from about 50 to about 2000 mM sodium acetate and from about 0.05 to about 0.2% polysorbate 80, and where the first buffer has a pH from about 5.2 to about 6.8; a second wash step comprises applying to the affinity resin a second buffer comprising from about 30 to about 200 mM TrisHCl and from about 75 to about 500 mM salt, and where the second buffer has a pH from about 7.5 to about 9.2; and a third wash step comprises applying to the affinity resin a third buffer comprising from about 30 to about 200 mM TrisHCl and from about 30 to about 75 vol % ethylene glycol, and where the third buffer has a pH from about 7.3 to about 8.8. In some embodiments, the salt is selected from NaC, KCl, $MgCl_2$, $CaCl_2$, sodium citrate, LiCl, CsCl, sodium acetate, and a combination of one or more of NaCl, KCl, $MgCl_2$, $CaCl_2$, sodium citrate, LiCl, CsCl, and sodium acetate. In some embodiments, the salt is NaCl. In some embodiments, the concentration of the salt does not exceed 500 mM. In some embodiments, the concentration of the salt does not exceed 200 mM. In some embodiments, the concentration of salt in the third buffer does not exceed 500 mM. In some embodiments, the concentration of salt in the third buffer does not exceed 200 mM. In some embodiments, the method further comprises a fourth wash step that takes place before the first wash step and comprises applying to the affinity resin a fourth buffer comprising from about 10 to about 30 mM TrisHCl and from about 75 to about 250 mM NaCl, and where the fourth buffer has a pH from about 6.5 to about 8.0. In some embodiments, the first buffer comprises about 100 mM sodium acetate, about 0.1% polysorbate 80, and where the first buffer has a pH of about 6.0. In some embodiments, the second buffer comprises about 50 mM TrisHCl and about 125 mM NaCl, and where the second buffer has a pH of about 8.5. In some embodiments, the third buffer comprises about 50 mM TrisHCl and about 50 vol % ethylene glycol, and where the third buffer has a pH of about 8.5.

In some embodiments, the organic solvent or detergent is polysorbate 80, ethylene glycol, sorbitol, mannitol, xylitol, sucrose, or trehalose.

In some embodiments, at least three wash steps are performed; a first wash step comprises applying to the affinity resin a first buffer comprising from about 50 to about 200 mM sodium acetate and from about 0.05 to about 0.2% polysorbate 80, and where the first buffer has a pH from about 5.5 to about 6.5; a second wash step comprises applying to the affinity resin a second buffer comprising from about 10 to about 70 mM TrisHCl and from about 75 to about 250 mM NaCl, and where the second buffer has a pH from about 8.0 to about 9.0; and a third wash step comprises applying to the affinity resin a third buffer comprising from about 10 to about 70 mM TrisHCl and from about 30 to about 75 vol % ethylene glycol, and where the third buffer has a pH from about 8.0 to about 9.0. In some embodiments, the method further comprises a fourth wash step that takes place before the first wash step and comprises applying to the affinity resin a fourth buffer comprising from about 10 to about 30 mM TrisHCl and from about 75 to about 250 mM NaCl, and where the fourth buffer has a pH from about 6.5 to about 8.0. In some embodiments, the first buffer comprises about 100 mM sodium acetate and about 0.1% Polysorbate 80, and the first buffer has a pH of about 6.0. In some embodiments, the second buffer comprises about 50 mM TrisHCl and about 125 mM NaCl, and where the second buffer has a pH of about 8.5. In some embodiments, the third buffer comprises about 50 mM TrisHCl and about 50 vol % ethylene glycol, and where the third buffer has a pH of about 8.0.

In yet more embodiments, at least three wash steps are performed; a first wash step comprises applying to the affinity resin a first buffer comprising from about 50 to about 500 mM sodium salt of 2-(N-morpholino)ethanesulfonic acid (MES-Na), from about 3 to about 30 mM EDTA, and a solvent/detergent mixture comprising polysorbate 80, DMSO and tri(n-butyl)phosphate (TNBP), and where the first buffer has a pH from about 5.2 to about 6.8; a second wash step comprises applying to the affinity resin a second buffer comprising from about 30 to about 200 mM TrisHCl or Arginine-HCl and from about 75 to about 500 mM salt, and where the second buffer has a pH from about 7.5 to about 9.2; and a third wash step comprises applying to the affinity resin a third buffer comprising from about 20 to about 80 mM Arginine-HCl and from about 50 to about 60% (w/w) sucrose, and where the third buffer has a pH from about 7.3 to about 8.8. In some embodiments, the salt is selected from NaCl, KCl, $MgCl_2$, $CaCl_2$, sodium citrate, LiCl, CsCl, sodium acetate, and a combination of one or more of NaCl, KCl, $MgCl_2$, $CaCl_2$, sodium citrate, LiCl, CsCl, and sodium acetate. In some embodiments, the salt is NaCl. In some embodiments, the concentration of the salt does not exceed 500 mM. In some embodiments, the concentration of the salt does not exceed 200 mM. In some embodiments, the concentration of salt in the third buffer does not exceed 500 mM. In some embodiments, the concentration of salt in the third buffer does not exceed 200 mM. In some embodiments, the method further comprises a fourth wash step that takes place before the first wash step and comprises applying to the affinity resin a fourth buffer comprising from about 20 to about 100 mM Arginine-HCl and from about 75 to about 250 mM NaCl, and where the fourth buffer has a pH from about 7.5 to about 8.8. In some embodiments, the first elution step comprises applying to the affinity resin a first elution buffer comprising from about 20 to about 100 mM Arginine-HCl and from about 40 to about 60% (w/w) sucrose, and where the first elution buffer has a pH from about 7.5 to about 8.5. In some embodiments, the method further comprises a fifth wash step that takes place after the first elution step and before a second elution step, the wash step comprising applying to the affinity resin a fifth buffer comprising from about 20 to about 100 mM Arginine-HCl and from about 75 to about 250 mM NaCl, and where the fifth buffer has a pH from about 7.5 to about 8.5. In some embodiments, the second elution step comprises applying to the affinity resin a second elution buffer comprising from about 20 to about 100 mM Arginine-HCl, from about 40 to about 60% (w/w) glycerol, and from about 500 to 1000 mM salt (e.g., NaCl), and where the second elution buffer has a pH from about 7.5 to about 8.5. The fifth wash step may be effective to minimize fronting effects between the first and second elution steps, e.g., providing for elution triggered only by the first and second elution buffers themselves and not from fronting that may result from a mixture of the first and second elution buffers. In some embodiments, the method further comprises a sixth wash step that takes place after the fifth wash step and the second elution step, the wash step comprising applying to the affinity resin a sixth buffer comprising from about 20 to about 100 mM Arginine-HCl and from about 75 to about 250 mM NaCl, and where the fifth buffer has a pH from about 7.5 to about 8.5.

In certain embodiments, the first buffer comprises about 100 mM sodium salt of 2-(N-morpholino)ethanesulfonic acid (MES-Na), about 10 mM EDTA, and about 11 g/kg of a solvent/detergent mixture comprising about 18 grams of polysorbate 80, 3.5 grams DMSO and 3.5 grams of tri(n-butyl)phosphate (TNBP), and where the first buffer has a pH of about 6.0. In certain embodiments, the second buffer comprises about 50 mM Arginine-HCl and about 100 mM NaCl, and where the second buffer has a pH of about 8.0. In certain embodiments, the third buffer comprises about 50 mM Arginine-HCl and about 50% (w/w) sucrose, and where the third buffer has a pH of about 8.5. In certain embodiments, the fourth buffer comprises about 50 mM Arginine-HCl and about 100 mM NaCl, and where the fourth buffer has a pH of about 8.0. In certain embodiments, the fifth buffer comprises about 50 mM Arginine-HCl and about 100 mM NaCl, and where the fifth buffer has a pH of about 8.0. In certain embodiments, the sixth buffer comprises about 50 mM Arginine-HCl and about 100 mM NaCl, and where the sixth buffer has a pH of about 8.0.

In some embodiments, at least three wash steps are performed; a first wash step comprises applying to the affinity resin a first buffer comprising from about 50 to about 200 mM taurine, and 0.2 to 1.5% PEG (e.g., PEG 6000), and where the first buffer has a pH from about 5.2 to about 6.8; a second wash step comprises applying to the affinity resin a second buffer comprising from about 30 to about 300 mM glycine, and where the second buffer has a pH from about 7.5 to about 9.2; and a third wash step comprises applying to the affinity resin a third buffer comprising from about 20 to about 150 mM taurine, from about 30 to about 75 vol % ethylene glycol, and from 0.05 to 0.2% octylglycopyranoside, and where the third buffer has a pH from about 7.3 to about 8.8. In some embodiments, the salt is selected from NaCl, KCl, $MgCl_2$, $CaCl_2$), sodium citrate, LiC, CsCl, sodium acetate, and a combination of one or more of NaCl, KCl, $MgCl_2$, $CaCl_2$), sodium citrate, LiC, CsCl, and sodium acetate. In some embodiments, the salt is NaCl. In some embodiments, the concentration of the salt does not exceed 500 mM. In some embodiments, the concentration of the salt does not exceed 200 mM. In some embodiments, the method further comprises a fourth wash step that takes place before the first wash step and comprises applying to the affinity resin a fourth buffer comprising from about 20 to about 100 mM TrisHCl and from about 75 to about 250 mM NaCl, and where the fourth buffer has a pH from about 7.5 to about 8.8.

In some embodiments, the first elution step comprises applying to the affinity resin a first elution buffer comprising from about 30 to about 70 mM taurine, from about 50 to about 70 vol % ethylene glycol, from 0.05 to 0.2% octylglycopyranoside, and from about 600 to about 900 mM NaCl, and where the first elution buffer has a pH from about 7.5 to about 8.5. In some embodiments, the method further comprises a fifth wash step that takes place after the first elution step and before a second elution step, the wash step comprising applying to the affinity resin a fifth buffer comprising from about 20 to about 100 mM TrisHCl and from about 75 to about 250 mM NaCl, and where the fifth buffer has a pH from about 7.5 to about 8.8. The fifth wash step may be effective to minimize fronting effects. In some embodiments, the second elution step comprises applying to the affinity resin a second elution buffer comprising from about 30 to about 70 mM TrisHCl, from 0.05 to 0.2 M ammonium sulfate, and from about 40 to about 60 vol % ethylene glycol and where the second elution buffer has a pH from about 6.5 to about 7.5. The fifth wash step may be effective to minimize fronting effects between the first and second elution steps, e.g., providing for elution triggered only by the first and second elution buffers themselves and not from fronting that may result from a mixture of the first and second elution buffers.

In some embodiments, the method further comprises a sixth wash step that takes place after the fifth wash step and the second elution step, the wash step comprising applying to the affinity resin a sixth buffer comprising from about 20 to about 100 mM TrisHCl and from about 75 to about 250 mM NaCl, and where the fifth buffer has a pH from about 7.5 to about 8.8.

In certain embodiments, the first buffer comprises about 100 mM taurine, and about 0.5% PEG 6000 where the first buffer has a pH of about 6.0. In certain embodiments, the second buffer comprises about 100 mM glycine, and the second buffer has a pH from about 7.5 to about 9.2. In certain embodiments, the third buffer comprises about 50 mM taurine, about 50% (w/w) ethylene glycol, and 0.1% octylglycopyranoside, and where the third buffer has a pH of about 8.5. In certain embodiments, the fourth buffer comprises about 50 mM TrisHCl and about 125 mM NaCl, and where the fourth buffer has a pH of about 8.5. In certain embodiments, the fifth buffer comprises about 50 mM TrisHCl and about 125 mM NaCl, and where the fifth buffer has a pH of about 8.5. In certain embodiments, the sixth buffer comprises about 50 mM TrisHCl and about 125 mM NaCl, and where the sixth buffer has a pH of about 8.5.

In some embodiments, at least three wash steps are performed; a first wash step comprises applying to the affinity resin a first buffer comprising from about 80 to about 400 mM Bis-Tris, and about 10 to about 20 grams of a solvent/detergent mixture comprising Triton-X100, polysorbate 80 and TNBP in a ratio of about 11:3:3 (by weight), and where the first buffer has a pH from about 5.2 to about 6.8; a second wash step comprises applying to the affinity resin a second buffer comprising from about 5 to about 20 mmol sodium citrate, and where the second buffer has a pH from about 7.5 to about 9.2; and a third wash step comprises applying to the affinity resin a third buffer comprising from about 50 to about 200 mM Arginine-HCl, from about 50 to about 200 mM Lysine HCl, from about 50 to about 200 mM Histidine-HCl, from about 1 mM to about 4 mM N-acetyl-D,L-tryptophan, and about 10% to about 40% (w/w) polysorbate 80, and where the third buffer has a pH from about 7.3 to about 8.8. In some embodiments, the salt is selected from NaCl, KCl, $MgCl_2$, $CaCl_2$, sodium citrate, LiCl, CsCl, sodium acetate, and a combination of one or more of NaCl, KCl, $MgCl_2$, $CaCl_2$, sodium citrate, LiCl, CsCl, and sodium acetate. In some embodiments, the salt is NaCl. In some embodiments, the concentration of the salt does not exceed 500 mM. In some embodiments, the concentration of the salt does not exceed 200 mM. In some embodiments, the method further comprises a fourth wash step that takes place before the first wash step and comprises applying to the affinity resin a fourth buffer comprising from about 20 to about 100 mM Histidine and from about 75 to about 250 mM NaCl, and where the fourth buffer has a pH from about 7.5 to about 8.8.

In some embodiments, the first elution step comprises applying to the affinity resin a first elution buffer comprising from about 15 to 25% sucrose, 5% to 15% (w/w) sorbitol, 3% to 7% (w/w) mannitol, 10% to 20% (w/w) glycerol, 40 to 60 mM histidine and from 700 to 900 mM salt (e.g., NaCl), and where the first elution buffer has a pH from about 7.5 to about 8.5. In some embodiments, the method further comprises a fifth wash step that takes place after the first elution step and before a second elution step, the wash step comprising applying to the affinity resin a fifth buffer comprising from about 20 to about 100 mM Histidine and from about 75 to about 250 mM NaCl, and where the fifth buffer has a pH from about 7.5 to about 8.8. In some embodiments, the second elution step comprises applying to the affinity resin a second elution buffer comprising from about 30 to about 70 mM TrisHCl, from about 700 to about 900 mM salt (e.g., NaCl), and from 40% to 60% (w/w) DMSO and where the second elution buffer has a pH from about 7.5 to about 8.5. The fifth wash step may be effective to minimize fronting effects between the first and second elution steps, e.g., providing for elution triggered only by the first and second elution buffers themselves and not from fronting that may result from a mixture of the first and second elution buffers. In some embodiments, the method further comprises a sixth wash step that takes place after the fifth wash step and a second elution step, the wash step comprising applying to the affinity resin a sixth buffer comprising from about 20 to about 100 mM Histidine and from about 75 to about 250 mM NaCl, and where the fifth buffer has a pH from about 7.5 to about 8.8.

In certain embodiments, the first buffer comprises about 200 mM Bis-Tris, about 16 to about 17 grams of a solvent/detergent mixture comprising about Triton-X100, polysorbate 80 and TNBP in a ratio of about 11:3:3 (by weight) where the first buffer has a pH of about 6.0. In some embodiments, the second buffer comprises about 10 mmol sodium citrate, and the second buffer has a pH of about 8.5. In some embodiments, the third buffer comprises about 100 mM Arginine-HCl, about 100 mM Lysine-HCl, about 100 mM Histidine-HCl, about 2 mM N-acetyl-D,L-tryptophan, and about 20% (w/w) polysorbate 80, and the third buffer has a pH of about 8.5. In certain embodiments, the fourth buffer comprises about 50 mM Histidine and about 100 mM NaCl, and where the fourth buffer has a pH of about 8.5. In certain embodiments, the fifth buffer comprises about 50 mM Histidine and about 100 mM NaCl, and where the fifth buffer has a pH of about 8.5. In certain embodiments, the sixth buffer comprises about 50 mM Histidine and about 100 mM NaCl, and where the sixth buffer has a pH of about 8.5.

In some embodiments, at least three wash steps are performed; a first wash step comprises applying to the affinity resin a first buffer comprising from about 50 nM to about 200 mM NaAcetate and from about 0.05 to about 0.2% Polysorbate80, where the first buffer has a pH of about 5.2 to about 6.8; a second wash step comprises applying to the affinity resin a second buffer comprising from about 20 nM to about 100 mM TrisHCl and from about 50 nM to about 200 nM of salt, where the second buffer has a pH of about 7.5 to about 8.8; and a third wash step comprises applying to the affinity resin a third buffer comprising about 20 mM to 100 mM TrisHCl, from about 40% to about 60% (w/w) ethylene glycol, and where the third buffer has a pH from about 7.5 to about 8.8. In some embodiments, the salt is selected from NaCl, KCl, $MgCl_2$, $CaCl_2$), sodium citrate, LiC, CsCl, sodium acetate, and a combination of one or more of NaCl, KCl, $MgCl_2$, $CaCl_2$), sodium citrate, LiCl, CsCl, and sodium acetate. In some embodiments, the salt is NaCl. In some embodiments, the concentration of the salt does not exceed 500 mM. In some embodiments, the concentration of the salt does not exceed 200 mM. In some embodiments, the method further comprises a fourth wash step that takes place before the first wash step and comprises applying to the affinity resin a fourth buffer comprising from about 10 to about 50 mM TrisHCl and from about 75 to about 250 mM NaCl, and where the fourth buffer has a pH from about 6.5 to about 8.0. In some embodiments, the method further comprises a fifth wash step that takes place after the third wash step, and comprises applying to the affinity resin a fifth buffer comprising from about 20 mM to about 100 mM TrisHCl, from about 50% to about 70% (w/w) ethylene glycol, and from about 500 to about 900 mM NaCl, and where the fifth buffer has a pH from about 7.5 to about 8.5. In some embodiments, the method further comprises a sixth wash step that takes place after the fifth wash step, and comprises applying to the affinity resin a sixth buffer comprising from about 10 mM to about 50 mM TrisHCl and from about 75 to about 250 mM NaCl, and where the sixth buffer has a pH from about 7.0 to about 8.0.

In certain embodiments, the first buffer comprises about 100 mM taurine, and about 0.5% PEG 6000 where the first buffer has a pH of about 6.0. In certain embodiments, the second buffer comprises about 100 mM glycine, and the second buffer has a pH from about 7.5 to about 9.2. In certain embodiments, the third buffer comprises about 50 mM taurine, about 50 vol % ethylene glycol, and from 0.1% octylglycopyranoside, and where the third buffer has a pH of about 8.5. In certain embodiments, the fourth buffer comprises about 20 mM Tris-HCl and about 150 mM NaCl, and where the fourth buffer has a pH of about 7.4. In certain embodiments, the fifth buffer comprises about 50 mM TrisHCl, 60% (w/w) ethylene glycol, and 750 mM NaCl, and where the fifth buffer has a pH of about 8.0. In certain embodiments, the sixth buffer comprises about 20 mM TrisHCl and about 150 mM NaCl, and where the sixth buffer has a pH of about 7.4.

In some embodiments, at least three wash steps are performed; a first wash step comprises applying to the affinity resin a first buffer comprising from about 50 nM to about 200 mM NaAcetate and from about 0.05 to about 0.2% Polysorbate80, where the first buffer has a pH of about 5.2 to about 6.8; a second wash step comprises applying to the affinity resin a second buffer comprising from about 20 nM to about 100 mM TrisHCl and from about 50 nM to about 200 nM of salt, where the second buffer has a pH of about 7.5 to about 8.8; and a third wash step comprises applying to the affinity resin a third buffer comprising about 20 mM to 100 mM TrisHCl, from about 40% to about 60% (w/w) ethylene glycol, and where the third buffer has a pH from about 7.5 to about 8.8. In some embodiments, the salt is selected from NaCl, KCl, MgCl$_2$, CaCl$_2$), sodium citrate, LiC, CsCl, sodium acetate, and a combination of one or more of NaCl, KCl, MgCl$_2$, CaCl$_2$), sodium citrate, LiC, CsCl, and sodium acetate. In some embodiments, the salt is NaCl. In some embodiments, the concentration of the salt does not exceed 500 mM. In some embodiments, the concentration of the salt does not exceed 200 mM. In some embodiments, the method further comprises a fourth wash step that takes place before the first wash step and comprises applying to the affinity resin a fourth buffer comprising from about 10 to about 50 mM TrisHCl and from about 75 to about 250 mM NaCl, and where the fourth buffer has a pH from about 6.5 to about 8.0. In some embodiments, the method further comprises a fifth wash step that takes place after the third wash step and comprises applying to the affinity resin a fifth buffer comprising from about 20 mM to about 100 mM TrisHCl, from about 50% to about 70% (w/w) ethylene glycol, and from about 500 to about 900 mM NaCl, and where the fifth buffer has a pH from about 7.5 to about 8.5. In some embodiments, the method further comprises a sixth wash step that takes place after the fifth wash step and comprises applying to the affinity resin a sixth buffer comprising from about 10 mM to about 50 mM TrisHCl and from about 75 to about 250 mM NaCl, and where the sixth buffer has a pH from about 7.0 to about 8.0.

In certain embodiments, the first buffer comprises about 100 mM taurine, and about 0.5% PEG 6000 where the first buffer has a pH of about 6.0. In certain embodiments, the second buffer comprises about 100 mM glycine, and the second buffer has a pH from about 7.5 to about 9.2. In certain embodiments, the third buffer comprises about 50 mM taurine, about 50 vol % ethylene glycol, and from 0.1% octylglycopyranoside, and where the third buffer has a pH of about 8.5. In certain embodiments, the fourth buffer comprises about 20 mM Tris-HCl and about 150 mM NaCl, and where the fourth buffer has a pH of about 7.4. In certain embodiments, the fifth buffer comprises about 50 mM TrisHCl, 60% (w/w) ethylene glycol, and 750 mM NaCl, and where the fifth buffer has a pH of about 8.0. In certain embodiments, the sixth buffer comprises about 20 mM TrisHCl and about 150 mM NaCl, and where the sixth buffer has a pH of about 7.4.

In some embodiments, at least three wash steps are performed; a first wash step comprises applying to the affinity resin a first buffer comprising from about 50 to about 200 mM sodium acetate, and 0.05 to 0.2% Polysorbate80, and where the first buffer has a pH from about 5.2 to about 6.8; a second wash step comprises applying to the affinity resin a second buffer comprising from about 25 to about 100 mM TrisHCl and from about 50 to 200 mM salt, and where the second buffer has a pH from about 7.5 to about 9.2. In some embodiments, the salt is selected from NaCl, KCl, MgCl$_2$, CaCl$_2$, sodium citrate, LiCl, CsCl, sodium acetate, and a combination of one or more of NaC, KCl, MgCl$_2$, CaCl$_2$, sodium citrate, LiCl, CsCl, and sodium acetate. In some embodiments, the salt is NaCl. In some embodiments, the method further comprises a third wash step that takes place before the first wash step and comprises applying to the affinity resin a third buffer comprising from about 20 to about 100 mM TrisHCl and from about 75 to about 250 mM NaCl, and where the third buffer has a pH from about 7.5 to about 8.8. In some embodiments, the first elution step comprises applying to the affinity resin purified water, followed by applying 0.5 to 2 mM HCl at a pH of 3.0 to 3.5, followed by applying a buffer comprising from about 25 to about 100 mM TrisHCl, from about 500 to about 1000 mM NaCl, and from about 25% to about 75% DMSO (w/w), and where the buffer comprises a pH from about 7.5 to about 8.5. In some embodiments, the method further comprises a fourth wash step that takes place after the first elution step and before a second elution step, the wash step comprising applying purified water to the affinity resin. In some embodiments, the second elution step comprises applying to the affinity resin from about 20 to about 50 mM HCl at a pH from about 1.7 to about 2.5.

In certain embodiments, the first buffer comprises about 100 mM sodium acetate, and about 0.1% Polysorbate80, where the first buffer has a pH of about 6.0. In certain embodiments, the second buffer comprises about 50 mM TrisHCl, about 125 mM NaCl, and the second buffer has a pH of about 8.5. In certain embodiments, the third buffer comprises about 50 mM TrisHCl and from about 125 mM NaCl, and where the third buffer has a pH of about 8.5. In certain embodiments, the first elution step comprises applying to the affinity resin purified water, followed by applying 1 mM HCl at a pH of about 3.2, followed by applying to the affinity resin a buffer comprising about 50 mM TrisHCl, about 750 mM NaCl, and about 50% DMSO (w/w), and where the buffer comprises a pH of about 8.0. In certain embodiments, the second elution step comprises applying to the affinity resin about 33 mM HCl at a pH of about 2.0.

In some embodiments, at least three wash steps are performed; a first wash step comprises applying to the affinity resin a first buffer comprising from about 50 to about 200 mM sodium acetate, and 0.05 to 0.2% Polysorbate80, and where the first buffer has a pH from about 5.2 to about 6.8; a second wash step comprises applying to the affinity resin a second buffer comprising from about 25 to about 100 mM TrisHCl and from about 50 to 200 mM salt, and where the second buffer has a pH from about 7.5 to about 9.2. In some embodiments, the salt is selected from NaCl, KCl, MgCl$_2$, CaCl$_2$, sodium citrate, LiCl, CsCl, sodium acetate, and a combination of one or more of NaC, KCl, MgCl$_2$, CaCl$_2$, sodium citrate, LiCl, CsCl, and sodium acetate. In some embodiments, the salt is NaCl. In some embodiments, the method further comprises a third wash step that takes place before the first wash step and comprises applying to the affinity resin a third buffer comprising from about 20 to about 100 mM TrisHCl and from about 75 to about 250 mM NaCl, and where the third buffer has a pH from about 7.5 to about 8.8. In some embodiments, the first elution step comprises applying to the affinity resin a gradient of 0 to 100% 20-50 mM Hydrochloric acid/800-1200 mMNaCl in 0.5-2.0 mM Hydrochloric acid. In certain embodiments, the gradient is of 0 to 100% 33 mM Hydrochloric acid/1000 mMNaCl in 1 mM Hydrochloric acid. In certain embodiments, the first elution step is preceded by a wash with purified water.

In certain embodiments, the first buffer comprises about 100 mM sodium acetate, and about 0.1% Polysorbate80, where the first buffer has a pH of about 6.0. In certain embodiments, the second buffer comprises about 50 mM TrisHCl, about 125 mM NaCl, and the second buffer has a pH of about 8.5. In certain embodiments, the third buffer comprises about 50 mM TrisHCl and from about 125 mM NaCl, and where the third buffer has a pH of about 8.5. In certain embodiments, the first elution step comprises applying to the affinity resin a buffer comprising from about 50 mM TrisHCl, about 750 mM NaCl, and about 50% DMSO (w/w), and where the buffer comprises a pH of about 8.0.

In some embodiments, the organic solvent or detergent is polysorbate 80, ethylene glycol, sorbitol, mannitol, xylitol, sucrose, or trehalose.

In some embodiments, an acidic component is removed. In some embodiments, the acidic component is host cell DNA, such as HEK293 DNA, and the acidic component is reduced to a value below 250 pg per microgram of AAV antigen as measured by qPCR. In some embodiments, the acidic component is host cell DNA, such as HEK293 DNA, and where the acidic component is reduced to a value below 250 pg per microgram of AAV antigen as measured by ELISA.

In some embodiments, eluting comprises contacting the affinity resin with an elution buffer comprising ethylene glycol, a salt such as NaCl, and a buffer such as TrisHCl, where the pH is at least 7.0. In some embodiments, the salt concentration is about 750 mM, the buffer concentration is about 50 mM, and the ethylene glycol is 50-60% (w/w). In some embodiments, the concentration of ethylene glycol is at least 55% (w/w). In some embodiments, the salt is NaCl and the buffer is TrisHCl. In some embodiments, the pH of the elution buffer is about 8.0. In some embodiments, the pH of the elution buffer is 8.0.

In some embodiments, eluting comprises contacting the affinity resin with an elution buffer comprising a sugar, such as sucrose, a salt, and a buffer, such as Arginine-HCl, where the pH is at least 8.0. In some embodiments, the salt concentration is about 800 mM. In some embodiments, the buffer concentration is about 50 mM. In some embodiments, the sugar is sucrose and the elution buffer comprises 50-60% (w/w) sucrose. In some embodiments, the elution buffer comprises 1-3 mM MgCl$_2$, or about 2 mM MgCl$_2$. In some embodiments, the salt is NaCl and the buffer is Arginine-HCl. In some embodiments, the pH of the elution buffer is about 8.0. In some embodiments, the pH of the elution buffer is 8.0.

In some embodiments, eluting comprises contacting the affinity resin with an elution buffer comprising ethylene glycol, a salt such as NaCl, and taurine, where the pH is at least 7.0. In some embodiments, the pH is 8.0. In some embodiments, the salt concentration is about 750 mM. In some embodiments, the buffer concentration is about 50 mM. In some embodiments, the ethylene glycol is concentration is 50-70% (w/w). In some embodiments, the concentration of ethylene glycol is at least 55% (w/w). In some embodiments, the elution buffer further comprises 0.05-0.2% octylglycopyranoside. In some embodiments, the pH of the elution buffer is about 8.0. In some embodiments, the pH of the elution buffer is 8.0.

In some embodiments, eluting comprises contacting the affinity resin with an elution buffer comprising (i) a mixture of sucrose, sorbitol, mannitol and glycerol, (ii) a salt such as NaCl, and (iii) a buffer such as histidine, where the pH is at least 7.8. In some embodiments, the salt concentration is about 800 mM. In some embodiments, the buffer concentration is about 50 mM. In some embodiments, the concentration of sucrose is about 20% (w/w). In some embodiments, the concentration of sorbitol is about 10% (w/w). In some embodiments, the concentration of mannitol is about 5% (w/w). In some embodiments, the concentration of glycerol is about 15% (w/w). In some embodiments, the salt is NaCl and the buffer is histidine. In some embodiments, the pH of the elution buffer is about 8.0. In some embodiments, the pH of the elution buffer is 8.0.

In some embodiments, a second eluting step is undertaken which comprises contacting the affinity resin with an elution buffer comprising (i) a buffer, (ii) a salt such as NaCl, and (iii) 50-60% (w/w) ethylene glycol, where the pH is at least 8.0. In some embodiments, the salt concentration is about 1000 mM. In some embodiments, the buffer concentration is about 50 mM. In some embodiments, the concentration of ethylene glycol is 60% (w/w). In some embodiments, the buffer is Tris HCl. In some embodiments, the salt is NaCl and the buffer is histidine. In some embodiments, the pH of the elution buffer is about 8.0. In some embodiments, the pH of the elution buffer is 8.0.

In some embodiments, a second eluting step is undertaken which comprises contacting the affinity resin with an elution buffer comprising (i) a buffer, (ii) a salt such as NaCl, and (iii) 50-60% (v/v) glycerol, where the pH is at least 8.0. In some embodiments, the salt concentration is about 800 mM, the buffer concentration is about 50 mM, and the concentration of glycerol is 50% (v/v). In some embodiments, the salt is NaCl and the buffer is Arginine-HCl. In some embodiments, the pH of the elution buffer is about 8.0. In some embodiments, the pH of the elution buffer is 8.0. In various embodiments, a fifth wash step is conducted after the first elution step and before the second eluting step. The fifth was step comprises contacting the affinity resin with a fifth buffer comprising 40-60 mM Arginine-HCl and 80-120 mM NaCl, at a pH of 7.5 to 8.5. The fifth wash step may be effective to minimize fronting effects between the first and second elution steps, e.g., providing for elution triggered only by the first and second elution buffers themselves and not from fronting that may result from a mixture of the first and second elution buffers.

In some embodiments, a second eluting step is undertaken which comprises contacting the affinity resin with an elution buffer comprising (i) a buffer, (ii) a salt such as (NH$_4$)$_2$SO$_4$, and (iii) 40-60% (v/v) ethylene glycol, where the pH is at least 8.0. In some embodiments, the salt concentration is about 1 M, the buffer concentration is about 50 mM, and the concentration of ethylene glycol is 50% (v/v). In some embodiments, the salt is $(NH_4)_2SO_4$ and the buffer is TrisHCl. In some embodiments, the pH of the elution buffer is about 7.0. In some embodiments, the pH of the elution buffer is 7.0. In various embodiments, a fifth wash step is conducted after the first elution step and before the second eluting step. The fifth was step comprises contacting the affinity resin with a fifth buffer comprising 40-60 mM Taurine, 50-70% (w/w) ethylene glycol, 600-900 mM NaCl, and 0.05-0.2% Octylglycopyranoside, at a pH of 7.5 to 8.5. The fifth wash step may be effective to minimize fronting effects between the first and second elution steps, e.g., providing for elution triggered only by the first and second elution buffers themselves and not from fronting that may result from a mixture of the first and second elution buffers.

In some embodiments, a second eluting step is undertaken which comprises contacting the affinity resin with an elution buffer comprising (i) a buffer, (ii) a salt such as NaCl, and (iii) 50-60% (w/w) DMSO, where the pH is at least 8.0. In some embodiments, the salt concentration is about 1000 mM. In some embodiments, the buffer concentration is about 50 mM. In some embodiments, the concentration of DMSO is 50% (w/w). In some embodiments, the salt is NaC and the buffer is TrisHCl. In some embodiments, the pH of the elution buffer is about 8.0. In some embodiments, the pH of the elution buffer is 8.0. In various embodiments, the DMSO-containing elution buffer is effective to elute AAV9 but not AAV8 from Capture Select AAV8 resin. In various embodiments, the DMSO-containing elution buffer is effective to elute AAV8 and AAV9 from Capture Select AAVx resin. In various embodiments, the DMSO-containing elution buffer is effective to elute one or more of AAV2, AAV3, AAV4, AAV5, AAV6, AAV7, AAV10, AAV11, AAV12, AAV13, AAAV, BAAV, AAV (VR-195) and AAV (VR-355), but not AAV8, from Capture Select AAV8 resin. In various embodiments, the DMSO-containing elution buffer is effective to elute any of AAV2, AAV3, AAV4, AAV5, AAV6, AAV7, AAV8, AAV10, AAV11, AAV12, AAV13, AAAV, BAAV, AAV (VR-195) and AAV (VR-355) from Capture Select AAVx resin.

In various embodiments, a fifth wash step is conducted after the first elution step and before the second eluting step. The fifth was step comprises contacting the affinity resin with a fifth buffer comprising 40-60 mM histidine and 70-130 mM NaCl, at a pH of 8.0 to 8.8. The fifth wash step may be effective to minimize fronting effects between the first and second elution steps, e.g., providing for elution triggered only by the first and second elution buffers themselves and not from fronting that may result from a mixture of the first and second elution buffers.

In some embodiments, eluting comprises a continuous linear increase of the conductivity of the elution buffer by gradient elution. In some embodiments, eluting comprises a continuous linear increase of the concentration of the organic solvent by gradient elution. In some embodiments, eluting comprises contacting the affinity resin with an elution buffer comprising about 750 mM NaCl and 50-60% (w/w) ethylene glycol at a pH of at least 7.0. In some embodiments, the concentration of ethylene glycol is at least 55% (w/w). In some embodiments, the elution buffer is at a pH of about 8.0. In some embodiments, the elution buffer is at a pH of 8.0.

In some embodiments, eluting comprises a stepwise increase of a counter ion concentration. In some embodiments, eluting comprises a stepwise increase of an organic solvent concentration. In some embodiments, the salt in the elution buffer is selected from monovalent, divalent or polyvalent anions, such as chloride, acetate, sulfate, and citrate. In some embodiments, the AAV obtained from the eluting step has an HC impurity level of ≤99.9%. In some embodiments, the AAV obtained from the eluting step has an HC impurity level of ≤99.0%.

In some embodiments, the AAV is AAV8, the affinity resin is POROS™ CaptureSelect™ AAV8, and the elution buffer is acidic and does not comprise ethylene glycol. In some embodiments, the AAV is AAV9, the affinity resin is POROS™ CaptureSelect™ AAV9, and where the elution buffer is acidic and does not comprise ethylene glycol. In some embodiments, the AAV is AAV8, and where the affinity resin is an immune affinity resin consisting of an immobilized monoclonal antibody against AAV8 from type ADK8 or ADK8/9 immobilized on a chromatography matrix. In some embodiments, the AAV is AAV9, and where the affinity resin is an immune affinity resin consisting of an immobilized monoclonal antibody against AAV9 from type ADK9 or ADK8/9 immobilized on a chromatography matrix.

In some embodiments, the method further comprises contacting the AAV containing solution with a filter comprising positively charged groups effective to deplete acidic charged contaminants from the AAV containing solution. In some embodiments, the method further comprises nanofiltration of an AAV fraction to remove viruses greater than 35 nm. In some embodiments, the method further comprises a polish step comprising performing AEX chromatography with a column comprising tentacle gel. In some embodiments, the method further comprises testing an AAV fraction via an AAV-specific ELISA, e.g., specific for AAV8 or specific for AAV9. The AAV specific ELISA may be a sandwich ELISA specific for AAV, e.g., AAV8 or AAV9.

In another aspect is provided an AAV product produced by any method described herein.

AAV particles, e.g., AAV8 and AAV9 particles, are purified with an affinity step by undertaking a plurality of defined wash steps, e.g., by applying wash buffers to an AAV-bound affinity matrix, and an elution at conditions near neutral pH to retain the infectivity of the said virus. In certain embodiments, an anion exchange step is included prior to the affinity step. The anion exchanger step may be conducted in flow through mode. In certain embodiments, contaminants may be depleted that have an impact on the cycle time of the affinity resin used in the affinity step.

The methods of the present invention may result in higher purity of AAV, removal of host cell proteins, depletion of host cell DNA, removal of potential virus receptors, partial to complete inactivation of lipid enveloped viruses where AAV is bound on the ligand (e.g., during the wash step), and partial to complete inactivation of lipid enveloped viruses in liquid phase (e.g., during the elution step). Without wishing to be bound by theory, ethylene glycol on its own, or in combination with another additive, can inactivate such lipid enveloped viruses. Exemplary additives include nonionic detergents, aliphatic agents (e.g., TnBP), and detergents (e.g., polysorbate (e.g., Tween), Triton X100, TnBP). For example, the solvent-detergent mixture can comprise 1% Triton X100, 0.3% Tri-N-butyl phosphate, and 0.3% TWEEN 80.

The inactivation of enveloped viruses can be of particular importance when a Baculo transfection system is used. Elution according to the various embodiments described herein can prevent low pH exposure and retain high potency of the AAV. Further improvement can be seen when undertaking the wash steps and elution steps in succession according to the various embodiments and examples described herein.

The inactivation of lipid enveloped viruses "on column" was tested in various affinity chromatography runs in the above Examples 11, 12 and 13, as summarized in Table 1 below.

TABLE 1

Solvent detergent treatments used in Variant A, B and C

| Step at which Detergent Solvent was Applied | Example 11 | Example 12 | Example 13 |
|---|---|---|---|
| WASH 2 Possible on step: LOAD, WASH 1, WASH 2, WASH 3, WASH 4, ELUATE | Potential SD-Treatment 10 to 30 g/kg of a mixture of 18.0 g Tween 80 3.4 g DMSO, 3.6 g TnBP | None | Established SD-Treatment 16.6 g S/D solution of 10.87 g Triton X100 3.31 g Polysorbate 80 3.01 g TnBP |
| WASH 4 Possible on step: WASH 1, WASH 2, WASH 3, WASH4 | None | Elevated pH 8.5 in presence of 50 to 60%(w/w) Ethylene glycol and detergent e.g., 0.1 -10% Octylglyopyranoside Not in eluate | 1 to 20% (w/w) Polysorbate 80 Possible in eluate |
| WASH x | None | None | Polar organic solvent 50% Dimethlysufoxide |

The DMSO containing buffer Wash X buffer may be effective to trigger elution of AAV9, but not AAV, on a CaptureSelect AAV8 resin at near to neutral pH (e.g., pH 8.0), a result which was surprising. The DMSO containing buffer Wash X buffer may be effective to trigger elution of various AAVs, including but not limited to, AAV1, AAV2, AAV3, AAV4, AAV5, AAV6, AAV7, AAV8, AAV9, AAV10, AAV11, AAV12, AAV13, AAAV, BAAV, AAV (R-95), and AAV (VR-355), on a CaptureSelect AAVx resin at near to neutral pH (e.g., pH 8.0), a result which was surprising. Without wishing to be bound by theory, the Wash X buffer is expected to have the activities of washing the column and/or inactivating or disintegrating lipid-enveloped viruses. There was no expectation that the Wash X buffer would differentially elute AAV9 over AAV8.

The affinity purification step comprises one or more wash steps. The one or more wash steps can be followed by one or more elution steps. In certain embodiments, the methods of the present disclosure comprise a filtration step, which occurs prior to the affinity purification steps.

After culturing host cells, e.g., HEK293 cells, to produce AAV particles (e.g., AAV8, AAV9, etc.), and the clarified cell free culture supernatant is concentrated and/or filtered, the viral particles are loaded onto the affinity matrix. In certain embodiments, the viral particles are loaded in solution having a pH ranging from about 7.4 to about 7.8. In certain embodiments, the viral particles are loaded in solution having a pH ranging from about 8.3 to about 8.7. In certain embodiments, the viral particles are loaded in a solution having a pH of about 8.5. In certain embodiments, the pH is from 8.3 to 8.7 and the solution comprises NaCl and TrisHCl. In certain embodiments, the viral particles are loaded in a solution comprising about 20 mM TrisHCl and about 150 mM NaCl, and having a pH of about 8.5.

At least three different wash steps can be undertaken, each involving the same or different buffer. In certain embodiments, the wash buffers are different.

In certain embodiments, the first wash step uses a first buffer, which can be a sodium acetate (NaAcetate) based buffer. In certain embodiments, the first wash step uses a first buffer comprising a sodium salt of 2-(N-morpholino)ethanesulfonic acid (MES-Na), EDTA, and a solvent/detergent mixture comprising polysorbate 80, DMSO and tri(n-butyl) phosphate (TNBP). In certain embodiments, the first wash step uses a first buffer comprising from about 50 to about 200 mM taurine, and 0.2 to 1.5% PEG (e.g., PEG 6000). In certain embodiments, the first wash step uses a first buffer comprising Bis-Tris, and a solvent/detergent mixture comprising Triton-X100, polysorbate 80 and TNBP. In certain embodiments, the first wash step uses a first buffer comprising sodium acetate and polysorbate 80.

In certain embodiments, the second wash step uses a second buffer, which can be a Tris based buffer comprising sodium chloride (NaCl), a glycine-based buffer, a sodium citrate-based buffer, or an Arginine-HCl based buffer comprising NaCl. In certain embodiments, the third wash step uses a third buffer, which can be a Tris-based buffer comprising ethylene glycol and/or NaCl, a taurine-based buffer, or an Arginine-HCl based buffer comprising NaCl. Alternatively, one or more of sorbitol, mannitol, xylitol, sucrose, or trehalose can be used in conjunction with ethylene glycol or instead of ethylene glycol. In certain embodiments, an optional fourth wash step, or reequilibration step, is performed prior to the three wash steps listed above. In the optional fourth wash step, a fourth buffer is used, which can be a Tris-based buffer comprising NaCl.

In certain embodiments, pre-purification can be undertaken to remove one or more of complex acidic protein structures and host cell DNA, prior to affinity purification of the AAV-containing solution from host cell production. Pre-purification may be conducted by anion exchange in flow through mode. The pre-purification step may be undertaken before any of the affinity purification methods described herein. One of more of the following may be removed by pre-purification of such AAV-containing solution: histones (e.g., histone H2A type 1, histone H2B type 1-B, histone H4, histone H1.4), 60S ribosomal proteins (e.g., 60S ribosomal protein L27, 60S ribosomal protein L6 and 60S ribosomal protein L30), cytoplasmic actin (e.g., cytoplasmic actin 1), tubulin (e.g., tubulin beta-2A chain), heterogeneous nuclear ribonucleoprotein C, Rep68 protein, HEK293 laminin receptor 37 kDa form (LamR 37 kDa) and ATP-dependent molecular chaperone HSC82.

The wash steps may be effective to remove strongly-bound contaminants from AAV and/or a base resin of the affinity matrix. For example, the buffer can comprise one or more of TrisHCl, acetate, phosphate, histidine, imidazole, lysine, arginine, glycine, taurine, citrate, HEPES, MES, MES-Na, borate, Bis-Tris, MOPS, bicine, tricine, TAPS, TAPSO, MES, PIPES, TES (2-[[1,3-dihydroxy-2-(hydroxymethyl)propan-2-yl]amino]ethanesulfonic acid), sodium barbital (Veronal), ADA(N-(2-Acetamido)iminodiacetic acid), ACES(N-(2-Acetamido)-2-aminoethanesulfonic acid), Bis-Tris Propane, BES(N,N-Bis(2-hydroxyethyl)-2-aminoethanesulfonic acid), DIPSO(3-(N,N-Bis[2-hydroxyethyl]amino)-2-hydroxypropanesulfonic acid), Trizma, HEPPSO(4-(2-Hydroxyethyl)piperazine-1-(2-hydroxypropanesulfonic acid)), POPSO(Piperazine-1,4-bis(2-hydroxypropanesulfonic acid) dehydrate), TEA, EPPS (4-(2-Hydroxyethyl)-1-piperazinepropanesulfonic acid), HEPBS(N-(2-Hydroxyethyl)piperazine-N'-(4-butanesulfonic acid), AMPD(2-Amino-2-methyl-1,3-propanediol), AMPSO(N-(1,1-Dimethyl-2-hydroxyethyl)-3-amino-2-hydroxypropanesulfonic acid), single amino acids or any combination of two or more amino acids that ensures the pH range and depletion rate of HEK-HCP, for example glycine, arginine, tryptophan, derivatives of amino acids, e.g., taurine (oxidized cysteine), N-Acetyl-Tryptophan, and glycylglycine. At the same time, the buffers used in the wash steps do not substantially elute the AAV.

In certain embodiments, the wash buffer can further comprise an organic solvent or detergent. For example, the organic solvent or detergent can be, but is not limited to, Tween 80, polysorbate 80, Triton X100, tri (n-butyl) phosphate (TNBP), ethylene glycol, sorbitol, mannitol, xylitol, sucrose, or trehalose. For example, the detergent can be, but not limited to, a nonionic polyoxyethylene surfactant (e.g., Brij 35), 4-Nonylphenyl-polyethylene glycol (Arkopal N100), octylglcoside, n-Dodecyl β-D-maltoside, Digitonin, 6-Cyclohexylhexyl β-D-maltoside, or octylglycopyranoside. For example, ethylene glycol can be PEG, such as but not limited to, PEG 2000, PEG4000, PEG6000 (Macrogol). For example, the organic solvent can be, but not limited to, glycerol (1,2,3-Propanetriol), and erythritol (meso-1,2,3,4-Butantetrol).

The organic solvent or detergent need not be present in all wash buffers used. However, an organic solvent or detergent is present in at least one of the wash buffers used. In some embodiments, a wash buffer, e.g., the first wash buffer, comprises both sodium acetate and Tween 80. In some embodiments, a wash buffer comprises one or more of Tween 80, DMSO and tri(n-butyl)phosphate (TNBP). In some embodiments, a wash buffer comprises one or more of Triton-X100, polysorbate 80 and TNBP. In some embodiments, a wash buffer, e.g., the third wash buffer, comprises Tris and ethylene glycol. Without wishing to be bound by theory, the organic solvents and detergents in the wash buffers are effective to remove strongly bound host proteins and virus receptors, while also inactivating and/or disintegrating lipid enveloped viruses.

The first buffer can comprise from about 50 to about 2000 mM sodium acetate, or 50 to about 250 mM sodium acetate, and from about 0.05 to about 5% polysorbate 80 or Tween 80 or 0.05 to about 0.2% polysorbate 80 or Tween 80, with a pH from 5.2 to 6.8. In certain embodiments, the first buffer can comprise from about 50 to about 75 mM; about 75 to about 100 mM; about 90 to about 110 mM; about 100 to about 125 mM; about 125 to about 150 mM sodium acetate; about 150 to about 175 mM sodium acetate; about 175 to about 200 mM sodium acetate; about 200 to about 250 mM sodium acetate; about 250 to about 300 mM sodium acetate; about 300 to about 350 mM sodium acetate; about 350 to about 400 mM sodium acetate; about 400 to about 450 mM sodium acetate; about 450 to about 500 mM sodium acetate; about 500 to about 550 mM sodium acetate; about 550 to about 600 mM sodium acetate; about 600 to about 650 mM sodium acetate; about 650 to about 700 mM sodium acetate; about 700 to about 750 mM sodium acetate; about 750 to about 800 mM sodium acetate; about 800 to about 850 mM sodium acetate; about 850 to about 900 mM sodium acetate; about 900 to about 950 mM sodium acetate; about 950 to about 1000 mM sodium acetate; about 1000 to about 1050 mM sodium acetate; about 1050 to about 1100 mM sodium acetate; about 1100 to about 1150 mM sodium acetate; about 1150 to about 1200 mM sodium acetate; about 1200 to about 1250 mM sodium acetate; about 1250 to about 1300 mM sodium acetate; about 1300 to about 1350 mM sodium acetate; about 1350 to about 1400 mM sodium acetate; about 1400 to about 1450 mM sodium acetate; about 1450 to about 1500 mM sodium acetate; about 1500 to about 1550 mM sodium acetate; about 1550 to about 1600 mM sodium acetate; about 1600 to about 1650 mM sodium acetate; about 1650 to about 1700 mM sodium acetate; about 1700 to about 1750 mM sodium acetate; about 1750 to about 1800 mM sodium acetate; about 1800 to about 1850 mM sodium acetate; about 1850 to about 1900 mM sodium acetate; about 1900 to about 1950 mM sodium acetate; or about 1950 to about 2000 mM sodium acetate.

In certain embodiments, the first buffer can comprise from about 50 to about 500 mM sodium salt of 2-(N-morpholino) ethanesulfonic acid (MES-Na), from about 3 to about 30 mM EDTA, and a solvent/detergent mixture comprising polysorbate 80, DMSO and tri(n-butyl)phosphate (TNBP). In certain embodiments, the first buffer can comprise from about 50 to about 75 mM; about 75 to about 100 mM; about 90 to about 110 mM; about 100 to about 125 mM; about 125 to about 150 mM; about 150 to about 175 mM; about 175 to about 200 mM; about 200 to about 250 mM; about 250 to about 300 mM; about 300 to about 350 mM; about 350 to about 400 mM; about 400 to about 450 mM; or about 450 to about 500 mM sodium salt of MES-Na. In certain embodiments, the first buffer can comprise about 50; about 75; about 90 mM; about 100 mM; about 125 mM; about 150 mM; about 175 mM; about 200 mM; about 250 mM; about 300 mM; about 350 mM; about 400 mM; about 450 mM; or about 500 mM sodium salt of MES-Na.

In certain embodiments, the first buffer can comprise from about 50 to about 200 mM taurine. In certain embodiments, the first buffer can comprise from about 50 to about 75 mM; about 75 to about 100 mM; about 90 to about 110 mM; about 100 to about 125 mM; about 125 to about 150 mM; about 150 to about 175 mM; about 175 to about 200 mM taurine. In certain embodiments, the first buffer can comprise about 50; about 75; about 90 mM; about 100 mM; about 125 mM; about 150 mM; about 175 mM; about 200 mM taurine.

In certain embodiments, the first buffer can comprise from about 80 to about 400 mM Bis-Tris. In certain embodiments, the first buffer can comprise from about 80 to about 100 mM; about 90 to about 110 mM; about 100 to about 125 mM; about 125 to about 150 mM; about 150 to about 175 mM; about 175 to about 200 mM; about 200 to about 250 mM; about 250 to about 300 mM; about 300 to about 350 mM; about 350 to about 400 mM Bis-Tris. In certain embodiments, the first buffer can comprise about 50; about 75; about 90 mM; about 100 mM; about 125 mM; about 150 mM; about 175 mM; about 200 mM; about 250 mM; about 300 mM; about 350 mM; about 400 mM Bis-Tris.

In certain embodiments, the first buffer can comprise from about 50 to about 200 mM sodium acetate. In certain embodiments, the first buffer can comprise from about 50 to about 80 mM; about 70 to about 100 mM; about 80 to about 110 mM; about 90 to about 120 mM; about 100 to about 130 mM; about 120 to about 150 mM; about 140 to about 170 mM; about 170 to about 200 mM sodium acetate. In certain embodiments, the first buffer can comprise about 60; about 70 mM; about 80 mM; about 90 mM; about 100 mM; about 110 mM; about 120 mM; about 130 mM; about 140 mM; about 150 mM; or about 160 mM sodium acetate.

In certain embodiments, the first buffer can comprise about 25 mM sodium acetate, about 50 mM sodium acetate, about 75 mM sodium acetate, about 100 mM sodium acetate, about 125 mM sodium acetate, about 150 mM sodium acetate, about 175 mM sodium acetate, about 200 mM sodium acetate, about 225 mM sodium acetate, about 250 mM sodium acetate, about 275 mM sodium acetate, about 300 mM sodium acetate, about 325 mM sodium acetate, about 350 mM sodium acetate, about 375 mM sodium acetate, about 400 mM sodium acetate, about 425 mM sodium acetate, about 450 mM sodium acetate, about 475 mM sodium acetate, about 500 mM sodium acetate, about 525 mM sodium acetate, about 550 mM sodium acetate, about 575 mM sodium acetate, about 600 mM sodium acetate, about 625 mM sodium acetate, about 650 mM sodium acetate, about 675 mM sodium acetate, about 700 mM sodium acetate, about 725 mM sodium acetate, about 750 mM sodium acetate, about 775 mM sodium acetate, about 800 mM sodium acetate, about 825 mM sodium acetate, about 850 mM sodium acetate, about 875 mM sodium acetate, about 900 mM sodium acetate, about 925 mM sodium acetate, about 950 mM sodium acetate, about 975 mM sodium acetate, about 1000 mM sodium acetate, about 1025 mM sodium acetate, about 1050 mM sodium acetate, about 1075 mM sodium acetate, about 1100 mM sodium acetate, about 1125 mM sodium acetate, about 1150 mM sodium acetate, about 1175 mM sodium acetate, about 1200 mM sodium acetate, about 1225 mM sodium acetate, about 1250 mM sodium acetate, about 1275 mM sodium acetate, about 1300 mM sodium acetate, about 1325 mM sodium acetate, about 1350 mM sodium acetate, about 1375 mM sodium acetate, about 1400 mM sodium acetate, about 1425 mM sodium acetate, about 1450 mM sodium acetate, about 1475 mM sodium acetate, about 1500 mM sodium acetate, about 1525 mM sodium acetate, about 1550 mM sodium acetate, about 1575 mM sodium acetate, about 1600 mM sodium acetate, about 1625 mM sodium acetate, about 1650 mM sodium acetate, about 1675 mM sodium acetate, about 1700 mM sodium acetate, about 1725 mM sodium acetate, about 1750 mM sodium acetate, about 1775 mM sodium acetate, about 1800 mM sodium acetate, about 1825 mM sodium acetate, about 1850 mM sodium acetate, about 1875 mM sodium acetate, about 1900 mM sodium acetate, about 1925 mM sodium acetate, about 1950 mM sodium acetate, about 1975 mM sodium acetate, or about 2000 mM sodium acetate. In certain embodiments, the first buffer can comprise about 100 mM, or 100 mM sodium acetate.

In certain embodiments, the first buffer can comprise about 0.05 to about 0.08%; about 0.08 to about 0.11%; about 0.11 to about 0.14%; about 0.14 to about 0.17%; or about 0.17 to about 0.20% polysorbate 80. In certain embodiments, the first buffer can comprise about 0.1%, or 0.1% polysorbate 80. In certain embodiments, the first buffer can comprise about 0.05 to about 0.08%; about 0.08 to about 0.11%; about 0.11 to about 0.14%; about 0.14 to about 0.17%; or about 0.17 to about 0.20% Tween 80. In certain embodiments, the first buffer can comprise about 0.1% Tween 80. In certain embodiments, the pH may be from about 5.2 to about 5.5; about 5.5 to about 5.8; about 5.8 to about 6.1; about 6.1 to about 6.4; or about 6.4 to about 6.8. In certain embodiments, the first buffer has a pH of about 6.0, or 6.0.

In certain embodiments, the first buffer comprises a chelating agent, e.g., EDTA.

The second buffer can comprise from about 30 to about 200 mM TrisHCl, or 30 to about 80 mM TrisHCl, and a salt, with the second buffer having a pH from about 7.5 to about 9.2. In some embodiments, the salt is NaCl, KCl, $MgCl_2$, $CaCl_2$, sodium citrate, LiC, CsCl, sodium acetate, or a combination of one or more of NaCl, KCl, $MgCl_2$, $CaCl_2$), sodium citrate, LiC, CsCl, and sodium acetate. In some embodiments, the salt is NaCl. The concentration of the salt, e.g., NaCl, can be from about 75 to about 500 mM. In some embodiments, the salt concentration, e.g., NaCl concentration, is from about 75 to about 200 mM. In some embodiments, the salt concentration, e.g., NaCl concentration, does not exceed 500 mM. In some embodiments, the salt concentration, e.g., NaCl concentration, does not exceed 200 mM. Without wishing to be bound by theory, a salt concentration not exceeding 500 mM, or not exceeding 200 mM, can prevent elution of AAV during the wash step because the conductivity of the salt solution is too low to bring about elution.

The second buffer can comprise from about 30 to about 35 mM; about 35 to about 40 mM; about 40 to about 45 mM; about 45 to about 50 mM; about 50 to about 55 mM; about 55 to about 60 mM; about 60 to about 65 mM; about 65 to about 70 mM; about 70 to about 75 mM; or about 75 to about 80 mM TrisHCl. In certain embodiments, the second buffer can comprise about 50 mM, or 50 mM TrisHCl. In certain embodiments, the second buffer can comprise from about 75 to about 100 mM; about 100 to about 125 mM; about 125 to about 150 mM; about 150 to about 175 mM; about 175 to about 200 mM; about 200 to about 225 mM; or about 225 to about 250 mM NaCl. In certain embodiments, the second buffer can comprise about 150 mM, or 150 mM NaCl. In certain embodiments, the pH of the second buffer can be from about 7.5 to about 7.7; about 7.7 to about 7.9; about 7.9 to about 8.1; about 8.1 to about 8.3; about 8.3 to about 8.5; about 8.5 to about 8.7; about 8.7 to about 8.9; or about 8.9 to about 9.2. In certain embodiments, the pH of the second buffer can be about 8.5, or 8.5.

The second buffer can comprise from about 30 to about 35 mM; about 35 to about 40 mM; about 40 to about 45 mM; about 45 to about 50 mM; about 50 to about 55 mM; about 55 to about 60 mM; about 60 to about 65 mM; about 65 to about 70 mM; about 70 to about 75 mM; or about 75 to about 80 mM Arginine-HCl. In certain embodiments, the second buffer can comprise about 50 mM, or 50 mM Arginine-HCl. In certain embodiments, the second buffer can comprise from about 75 to about 100 mM; about 100 to about 125 mM; about 125 to about 150 mM; about 150 to about 175 mM; about 175 to about 200 mM; about 200 to about 225 mM; or about 225 to about 250 mM NaCl. In certain embodiments, the second buffer can comprise about 150 mM, or 150 mM NaCl. In certain embodiments, the pH of the second buffer can be from about 7.5 to about 7.7; about 7.7 to about 7.9; about 7.9 to about 8.1; about 8.1 to about 8.3; about 8.3 to about 8.5; about 8.5 to about 8.7; about 8.7 to about 8.9; or about 8.9 to about 9.2. In certain embodiments, the pH of the second buffer can be about 8.5, or 8.5.

The second buffer can comprise from about 50 to about 200 mM glycine. In certain embodiments, the second buffer can comprise from about 50 to about 100 mM; about 70 to about 120 mM; about 100 to about 150 mM; about 120 to about 170 mM; about 150 to about 200 mM glycine. In certain embodiments, the pH of the second buffer can be from about 7.5 to about 7.7; about 7.7 to about 7.9; about 7.9 to about 8.1; about 8.1 to about 8.3; about 8.3 to about 8.5; about 8.5 to about 8.7; about 8.7 to about 8.9; or about 8.9 to about 9.2. In certain embodiments, the pH of the second buffer can be about 8.5, or 8.5.

The second buffer can comprise from about 50 to about 20 mM sodium citrate. In certain embodiments, the second buffer can comprise from about 5 to about 10 mM; about 7 to about 12 mM; about 10 to about 15 mM; about 12 to about 17 mM; about 15 to about 20 mM sodium citrate. In certain embodiments, the pH of the second buffer can be from about 7.5 to about 7.7; about 7.7 to about 7.9; about 7.9 to about 8.1; about 8.1 to about 8.3; about 8.3 to about 8.5; about 8.5 to about 8.7; about 8.7 to about 8.9; or about 8.9 to about 9.2. In certain embodiments, the pH of the second buffer can be about 8.5, or 8.5.

In certain embodiments, the second buffer comprises a chelating agent, e.g., EDTA.

The third buffer can comprise from about 30 to about 200 mM TrisHCl and from about 30 to about 75 vol % ethylene glycol, with a pH from about 7.5 to about 9.2. The third buffer can comprise from about 20 to about 80 mM Arginine-HCl and from about 50 to about 200 mM salt, with a pH from about 7.3 to about 8.8. The third buffer can comprise about 50 mM TrisHCl and about 50 vol % ethylene glycol, with a pH of about 8.5. The third buffer can comprise about 20 to about 150 mM taurine, about 30 to about 75 vol % ethylene glycol, and from 0.05 to 0.2% octylglycopyranoside, with a pH from about 7.3 to about 8.8. The third buffer can comprise about 50 to about 200 mM Arginine-HCl, about 50 to about 200 mM Lysine HCl, about 50 to about 200 mM Histidine-HCl, and about 1 mM to about 4 mM N-acetyl-D,L-tryptophan, and about 10% to about 40% (w/w) polysorbate 80, with a pH from about 7.3 to about 8.8. If a salt, e.g., NaCl, is present in the third buffer, in certain embodiments the concentration of the salt does not exceed 500 mM and in certain embodiments the concentration of the salt does not exceed 200 mM. In certain embodiments, the salt is NaCl, KCl, $MgCl_2$, $CaCl_2$), sodium citrate, LiCl, CsCl, sodium acetate, or a combination of one or more of NaCl, KCl, $MgCl_2$, $CaCl_2$, sodium citrate, LiCl, CsCl, and sodium acetate. In certain embodiments, the salt is NaCl. In certain embodiments, one or more of sorbitol, mannitol, xylitol, sucrose, or trehalose can be used in conjunction with ethylene glycol or instead of ethylene glycol.

Without wishing to be bound by theory, degree of elution of AAV is affected by both the amount of ethylene glycol and the conductivity of salt in the third buffer. An amount of at least 55% (w/w) ethylene glycol in the buffer can significantly increase the amount of elution, as compared to 50% (w/w) ethylene glycol. Accordingly, at a given ethylene glycol concentration, increased NaCl concentration can increase the extent and rate of elution. At a given ethylene glycol concentration, replacement of NaCl with a polyvalent salt also can increase the extent and rate of elution.

Without wishing to be bound by theory, if salt is constant, e.g., 750 mM NaCl, then increasing amount of ethylene glycol can increase the elution strength of the buffer. If the ethylene glycol content is constant, e.g., 55%, then increasing amount of salt can increase the elution strength of the buffer. Thus, the elution strength increases from 40% to 45% to 50% to 55% to 60% (w/w) ethylene glycol in 750 mM NaCl.

Increasing the ethylene glycol content of a solution with constant salt content can lower the conductivity. An increased amount of ethylene glycol can lower the amount of solubility of salt in the buffer.

In certain embodiments, the third buffer can comprise from about 30 to about 35 mM; about 35 to about 40 mM; about 40 to about 45 mM; about 45 to about 50 mM; about 50 to about 55 mM; about 55 to about 60 mM; about 60 to about 65 mM; about 65 to about 70 mM; about 70 to about 75 mM; about 75 to about 80 mM; about 80 to about 90 mM; about 90 to about 100 mM; about 100 to about 110 mM; about 110 to about 120 mM; about 120 to about 130 mM; about 130 to about 140 mM; about 140 to about 150 mM; about 150 to about 160 mM; about 160 to about 170 mM; about 170 to about 180 mM; about 180 to about 190 mM; or about 190 to about 200 mM TrisHCl. In certain embodiments, the third buffer can comprise about 50 mM, or 50 mM TrisHCl. In certain embodiments, the third buffer can comprise from about 30 to about 35 vol %; 35 to about 40 vol %; about 40 to about 45 vol %; about 45 to about 50 vol %; about 48 to about 52 vol %; about 50 to about 55 vol %; about 55 to about 60 vol %; about 60 to about 65 vol %; about 65 to about 70 vol %; or about 70 to about 75 vol % ethylene glycol. In certain embodiments, the third buffer can comprise about 50%, or 50% ethylene glycol. In certain embodiments, the pH of the third buffer can be from about 7.5 to about 7.7; about 7.7 to about 7.9; about 7.9 to about 8.1; about 8.1 to about 8.3; about 8.3 to about 8.5; about 8.5 to about 8.7; about 8.7 to about 8.9; or about 8.9 to about 9.2. In certain embodiments, the pH of the third buffer can be about 8.5, or 8.5.

In certain embodiments, the third buffer comprises a chelating agent, e.g., EDTA.

The fourth buffer can comprise from about 10 to about 30 mM TrisHCl and from about 75 to about 250 mM NaCl, with a pH from about 6.5 to about 8.0. In certain embodiments, the fourth buffer can comprise about 10 to about 15 mM; about 15 to about 20 mM; about 20 to about 25 mM; or about 25 to about 30 mM TrisHCl. In certain embodiments, the fourth buffer can comprise about 20 mM, or 20 mM TrisHCl. In certain embodiments, the fourth buffer can comprise from about 75 to about 100 mM; about 100 to about 125 mM; about 125 to about 150 mM; about 150 to about 175 mM; about 175 to about 200 mM; about 200 to about 225 mM NaCl; or about 225 to about 250 mM NaCl. In certain embodiments, the fourth buffer can comprise about 150 mM, or 150 mM NaCl. In certain embodiments, the fourth buffer can have a pH may be from about 6.5 to about 6.9; about 6.8 to about 7.2; about 7.1 to about 7.5; about 7.4 to about 7.9; or about 7.6 to about 8.0. In certain embodiments, the fourth buffer can have a pH of about 7.4, or 7.4.

The fourth buffer can comprise from about 20 to about 100 mM Histidine and from about 75 to about 250 mM NaCl, with a pH from about 7.5 to about 8.8. In certain embodiments, the fourth buffer can comprise from about 20 to about 40 mM; about 40 to about 60 mM; about 60 to about 75 mM; or about 75 to about 100 mM Histidine. In certain embodiments, the fourth buffer can comprise about 20 mM, or 20 mM Histidine. In certain embodiments, the fourth buffer can comprise from about 75 to about 100 mM; about 100 to about 125 mM; about 125 to about 150 mM; about 150 to about 175 mM; about 175 to about 200 mM; about 200 to about 225 mM NaCl; or about 225 to about 250 mM NaCl. In certain embodiments, the fourth buffer can comprise about 150 mM, or 150 mM NaCl. In certain embodiments, the fourth buffer can have a pH may be from about 7.5 to about 7.9; about 7.8 to about 8.2; about 8.1 to about 8.5; about 8.4 to about 8.9; or about 8.6 to about 9.0. In certain embodiments, the fourth buffer can have a pH of about 8.0, or 8.0.

In certain embodiments, the fourth buffer comprises a chelating agent, e.g., EDTA. In certain embodiments, an additional wash can be conducted with a buffer comprising a chelating agent, e.g., EDTA.

Following the wash steps, the AAV particles are eluted using an elution buffer. The elution buffer can comprise from about 30 to about 200 mM buffer, from about 30 to about 75 vol % ethylene glycol, and from about 500 mM to about 2000 mM of a salt, with the elution buffer having a pH from about 7.3 to about 8.8. In some embodiments, the concentration of ethylene glycol is at least 50% (w/w). In some embodiments, the concentration of ethylene glycol is at least 55% (w/w). In some embodiments, the concentration of ethylene glycol is at least 60% (w/w). In some embodiments, the buffer is TrisHCl, Glycine, Citrate, Arginine, Phosphate Glycine-HCl, ammonium sulfate, magnesium chloride, borate, bis-Tris, MOPS, bicine, tricine, TAPS, TAPSO, MES, PIPES, TES (2-[[1,3-dihydroxy-2-(hydroxymethyl) propan-2-yl]amino]ethanesulfonic acid), sodium barbital (Veronal), ADA(N-(2-Acetamido)iminodiacetic acid), ACES(N-(2-Acetamido)-2-aminoethanesulfonic acid), Bis-Tris Propane, BES(N,N-Bis(2-hydroxyethyl)-2-aminoethanesulfonic acid), DIPSO(3-(N,N-Bis[2-hydroxyethyl] amino)-2-hydroxypropanesulfonic acid), Trizma, HEPPSO (4-(2-Hydroxyethyl)piperazine-1-(2-hydroxypropanesulfonic acid)), POPSO(Piperazine-1,4-bis (2-hydroxypropanesulfonic acid) dehydrate), TEA, EPPS (4-(2-Hydroxyethyl)-1-piperazinepropanesulfonic acid), HEPBS(N-(2-Hydroxyethyl)piperazine-N'-(4-butanesulfonic acid), AMPD(2-Amino-2-methyl-1,3-propanediol), AMPSO(N-(1,1-Dimethyl-2-hydroxyethyl)-3-amino-2-hydroxypropanesulfonic acid), single amino acids or any combination of two or more amino acids to ensure pH and elution of AAV, for example glycine, arginine, tryptophan, derivatives of amino acids, e.g., taurine (oxidized cysteine), N-acetyl-tryptophan, and glycylglycine. In some embodiments, the buffer is TrisHCl.

In some embodiments, the salt is NaCl, KCl, $CaCl_2$), CsCl, LiCl, $CaCl_2$), sodium citrate, LiC, CsCl, or a combination of one or more of KCl, $CaCl_2$), CsCl, LiCl, $CaCl_2$), sodium citrate, LiCl, and CsCl. In some embodiments, the salt is NaCl. The concentration of the salt, e.g., NaCl, can be from about 500 to about 2000 mM. In some embodiments, the salt concentration is from about 500 to about 900 mM, about 750 mM NaCl, or 750 mM NaCl. In some embodiments, when a concentration gradient of NaCl is used, the target concentration is 2000 mM.

In certain embodiments, one or more of sorbitol, mannitol, xylitol, sucrose, trehalose, glycerol (1,2,3-Propanetriol), or erythritol (meso-1,2,3,4-butantetrol) can be used in conjunction with ethylene glycol or instead of ethylene glycol. In certain embodiments, the elution buffer can comprise from about 30 to about 35 mM; about 35 to about 40 mM; about 40 to about 45 mM; about 45 to about 50 mM; about 50 to about 55 mM; about 55 to about 60 mM; about 60 to about 65 mM; about 65 to about 70 mM; about 70 to about 75 mM; or about 75 to about 80 mM TrisHCl. In certain embodiments, the elution buffer can comprise about 50 mM, or 50 mM TrisHCl. In certain embodiments, the elution buffer can comprise from about 30 to about 35 vol %; about 35 to about 40 vol %; about 40 to about 45 vol %; about 45 to about 50 vol %; about 48 to about 52 vol %; about 50 to about 55 vol %; about 55 to about 60 vol %; about 60 to about 65 vol % about 65 to about 70 vol %; or about 70 to about 75 vol % ethylene glycol. In certain embodiments, the elution buffer can comprise about 50%, or 50% ethylene glycol. In certain embodiments, the concentration of ethylene glycol is at least 55% (w/w). In certain embodiments, the concentration of ethylene glycol is at least 56% (w/w). In certain embodiments, the concentration of ethylene glycol is at least 57% (w/w). In certain embodiments, the concentration of ethylene glycol is at least 58% (w/w). In certain embodiments, the elution buffer can comprise from about 500 to about 700 mM; about 550 to about 750 mM; about 600 to about 800 mM; about 650 to about 850 mM; about 700 to about 900 mM; about 750 to about 950 mM; about 800 to about 1000 mM NaCl; about 900 to about 1100 mM NaCl; about 1000 to about 1200 mM NaCl; about 1100 to about 1300 mM NaCl; about 1200 to about 1400 mM NaCl; about 1300 to about 1500 mM NaCl; about 1400 to about 1600 mM NaCl; about 1500 to about 1700 mM NaCl; about 1600 to about 1800 mM NaCl; about 1700 to about 1900 mM NaCl; about 1800 to about 2000 mM NaCl. In certain embodiments, the elution buffer can comprise about 750 mM, or 750 mM NaCl. The pH may be from 7.3 to 7.6. The pH may be from 7.5 to 7.8. The pH may be from 7.7 to 8.0. The pH may be from 7.9 to 8.2. The pH may be from 8.1 to 8.4. The pH may be from 8.3 to 8.6. The pH may be from 8.5 to 8.8.

In certain embodiments, elution is undertaken with an elution buffer comprising an organic solvent. For example, the organic solvent can comprise one or more of a polyol (e.g., ethylene glycol, sorbitol, mannitol, xylitol), glycerol, sucrose, trehalose, or a combination of polyols. The buffer can have a pH range between 7.5 to 8.5. Without wishing to be bound by theory, the organic solvent may inactivate lipid-enveloped viruses that can be produced if, for instance, the production of AAV involves Baculovirus transfection of Sf9 insect cells. The affinity eluate can contain an organic solvent (e.g., a polyol such as ethylene glycol) that can be used in an adjustable density gradient in a later ultracentrifugation step.

Any organic solvent in the wash buffers or in elution buffers may be able to disintegrate or inactivate lipid enveloped viruses. Such inactivation may occur by a combination of an on-column inactivation and in liquid state inactivation. In some embodiments, the organic solvent in an elution buffer and or a wash buffer has a concentration about 50% (w/w) to about 80% (w/w) to ensure disintegration or inactivation of lipid enveloped viruses. In some embodiments, the concentration is about 50% (w/w). In some embodiments, the concentration is about 55% (w/w). In certain embodiments, the concentration of ethylene glycol is about 56% (w/w). In certain embodiments, the concentration of ethylene glycol is about 57% (w/w). In certain embodiments, the concentration of ethylene glycol is about 58% (w/w). In certain embodiments, the concentration of ethylene glycol is about 59% (w/w). In some embodiments, the concentration is about 60% (w/w). In some embodiments, the concentration is about 65% (w/w). In some embodiments, the concentration is about 70% (w/w). In some embodiments, the concentration is about 75% (w/w). In some embodiments, the organic solvent in an elution buffer and or a wash buffer has a concentration about 40% (w/w) to ensure disintegration or inactivation of lipid enveloped viruses. In some embodiments, the organic solvent in an elution buffer and or a wash buffer has a concentration about 30% (w/w) to ensure disintegration or inactivation of lipid enveloped viruses. In some embodiments, the organic solvent in an elution buffer or a wash buffer can inactive or disintegrate Baculovirus.

In some embodiments, the first buffer is at a pH from about 5.8 to about 6.2 and comprises from about 90 to about 110 mM sodium acetate and about 0.09 to about 0.11% Polysorbate 80/Tween 80, the second buffer is at a pH from about 8.2 to about 8.8 and comprises from about 45 to about 55 mM TrisHCl and about 110 to about 135 mM NaCl, the third buffer is at a pH from about 8.2 to about 8.8 and comprises from about 45 to about 55 mM TrisHCl and about 45 to about 55% ethylene glycol, the optional fourth buffer is at a pH from about 7.2 to about 7.6 and comprises about 15 to about 25 mM TrisHCl and about 135 to about 165 mM NaCl. In certain embodiments, the elution buffer is at a pH from about 7.8 to about 8.2 and comprises from about 45 to about 55 mM TrisHCl, about 45 to about 55% ethylene glycol and about 650 to about 850 mM NaCl. Various volumes may be used, such as from about 2 column volumes to about 15 column volumes, from about 3 column volumes to about 7 column volumes, from about 4 column volumes to about 8 column volumes, from about 5 column volumes to about 10 column volumes, or from about 7 column volumes to about 12 column volumes. About 5 column volumes, or 5 column volumes, of each of the first, second, third, fourth, and elution buffers may be used. Alternatively, about 10 column volumes, or 10 column volumes, of each of the first, second, third, fourth, and elution buffers may be used. For example, 10 column volumes may be used when the column volume is about 2 ml to about 3 ml. Lengthening the time of wash steps may further be undertaken to improve AAV purity.

In some embodiments, the first buffer is at a pH from about 7.2 to about 7.6 and comprises about 15 to about 25 mM TrisHCl and about 135 to about 165 mM NaCl, the second buffer is at a pH from about 5.8 to about 6.2 and comprises from about 90 to about 110 mM sodium acetate and about 0.09 to about 0.11% polysorbate 80, the third buffer is at a pH from about 8.2 to about 8.8 and comprises from about 45 to about 55 mM TrisHCl and about 110 to about 135 mM NaCl, the fourth buffer is at a pH from about 7.5 to about 8.5 and comprises from about 45 to about 55 mM TrisHCl and about 45 to about 55% ethylene glycol, and the elution buffer is at a pH from about 7.8 to about 8.2 and comprises from about 45 to about 55 mM TrisHCl, about 45 to about 55% ethylene glycol and about 650 to about 850 mM NaCl. About 10 column volumes, or 10 column volumes, of each wash buffer may be used.

In some embodiments, the first buffer is at a pH from about 7.2 to about 7.6 and comprises about 15 to about 25 mM TrisHCl and about 135 to about 165 mM NaCl, the second buffer is at a pH from about 5.8 to about 6.2 and comprises from about 90 to about 110 mM sodium acetate and about 0.09 to about 0.11% polysorbate 80, the third buffer is at a pH from about 8.2 to about 8.8 and comprises from about 45 to about 55 mM TrisHCl and about 110 to about 135 mM NaCl, the fourth buffer is at a pH from about 7.5 to about 8.5 and comprises from about 45 to about 55 mM TrisHCl and about 45 to about 55% ethylene glycol. Elution is conducted with a gradient starting with a first elution buffer at a pH from about 7.8 to about 8.2 and comprises from about 45 to about 55 mM TrisHCl, about 45 to about 55% ethylene glycol and about 650 to about 850 mM NaCl and ending at a second elution buffer at a pH from about 7.8 to about 8.2 and comprising from about 45 to about 55 mM TrisHCl, about 45 to about 55% ethylene glycol and about 1900 to about 2100 mM NaCl. About 10 column volumes, or 10 column volumes, of each wash buffer may be used. Elution may be conducted with 10 column volumes of the gradient.

In certain embodiments, the solution containing the AAV particles undergoes ion exchange chromatography. In certain embodiments, the ion exchange is anion exchange. In certain embodiments, the anion exchange chromatography support can remove not only residual particle contaminants from cell culture but also acidic impurities and virus particles. In certain embodiments, the anion exchange chromatography can remove proteases and/or host cell DNA. In certain embodiments, ion exchange chromatography can be conducted with membrane-based separation, e.g., hybrid membrane-anion exchange chromatography. In certain embodiments, pure AEX chromatography is used, e.g., in flow through mode or bind/elute mode. In certain embodiments, the anion exchange support can be, but is not limited to Mustang® Q, STREAMLINE Q XL™, POROS 50 PI™, Q SEPHAROSE™, Emphase™ AEX Hybrid Purifier, Nuvia Q, POROS 50 HQ, Capto Q, Capto Q impress, Unosphere Q, Q Ceramic HYPERD® F, TOYOPEARL® Q, TOYOPEARL® Super Q, mixed mode AEX resins (e.g., Capto Adhere, Capto adhere impress, and MEP Hypercell), and any DEAE, TMAE, tertiary or quaternary amine, or PEI-based resins. In certain embodiments, the anion exchange support is Mustang® Q.

In certain embodiments, the DNA from HEK293 cells, or any host cell used, is not treated with Benzonase and/or DNase. The anion exchanger and wash steps described herein can be effective to remove such DNA such that there is no need to treat with Benzonase or DNase.

AAV is generally recovered from an anion exchange step in the flow-through fractions (depending on the pH). Alternatively, AAV can be used in the bind/elute method. Either the flow-through method or the bind/elute method should be conducted to exclude host cell impurities which elute at higher conductivity (at constant pH) or lower pH (at constant conductivity) than AAV. When operating in bind/elute mode, the pH and composition of the buffer is effective to trigger elution of the product but not of the acidic host cell impurities. Without wishing to be bound by theory, each binding and elution step can cause forces in the microenvironment such that the flow-through method in non-binding conditions may cause less damage or disintegration of AAV than a bind/elute method.

In various embodiments, the yield of AAV, e.g., AAV8 and AAV9, after the purification steps described herein and as measured by an ITR-qPCR assay as weight/volume, is at least 10%, 15%, 20%, 25%, 30%, 35%, 40%, 45%, 50%, 55%, 60%, or 65% greater than that obtained by a comparative procedure in which no wash steps are performed.

In various embodiments, the yield of AAV, e.g., AAV8 and AAV9, after the purification steps described herein and as measured by an ITR-qPCR assay as weight/weight, is at least 10%, 15%, 20%, 25%, 30%, 35%, 40%, 45%, 50%, 55%, 60%, or 65% greater than that obtained by a comparative procedure in which no wash steps are performed.

In certain embodiments, the methods of producing and purifying AAV described herein reduce the number of protein impurities by about 10%, 15%, 20%, 25%, 30%, 35%, 40%, 45%, 50%, 55%, 60%, 65%, 70%, 75%, 80%, 85%, 90%, 95%, 99% greater than that obtained by a comparative procedure without the same wash protocol. It was surprisingly found that the methods of producing and purifying AAV described herein reduced the number of protein impurities by at least 25%. It was surprisingly found that the methods of producing and purifying AAV described herein reduced the number of protein impurities by at least 75% when the solution of AAV particles were exposed to anion exchange chromatography prior to being loaded onto the affinity matrix. For example, the data in Table 7 of Example 2 shows that the number of protein impurities is reduced from 20 to 14 (without prior anion exchange) and from 20 to 4 (with prior anion exchange).

In certain embodiments, the methods of producing and purifying AAV described herein provide for purity of AAV, e.g., AAV8 and AAV9, that is at least 98.0%, 98.1%, 98.2%, 98.3%, 98.4%, 98.5%, 98.6%, 98.7%, 98.8%, 98.9%, 99.0%, 99.1%, or 99.2% when both anion exchange and affinity purification with wash steps are conducted as provided herein. In certain embodiments, the methods of producing and purifying AAV described herein provide for purity of AAV, e.g., AAV8 and AAV9, that is at least 96.0%, 96.1%, 96.2%, 96.3%, 96.4%, 96.5%, 96.6%, 96.7%, 96.8%, 96.9%, 97.0%, 97.1%, 97.2%, 97.3%, 97.4%, 97.5%, 97.6%, 97.7%, 97.8%, 97.9%, or 98.0% when affinity purification with wash steps is conducted as provided herein.

Advantageously, the methods are scalable to large volumes of starting material, e.g., cell culture. In certain embodiments, the methods provided herein are large-scale methods capable of purifying AAV from volumes of at least or about 500 L, at least or about 600 L, at least or about 700 L, at least or about 800 L, at least or about 900 L, or at least or about 1000 L. In certain embodiments, the methods are scalable to a minimum volume of starting material (e.g., cell culture) of at least or about 1250 L, at least or about 1500 L, at least or about 2000 L, at least or about 2500 L, at least or about 3000 L, at least or about 4000 L, at least or about 5000 L, at least or about 6000 L, at least or about 7000 L, at least or about 8000 L, at least or about 9000 L, at least or about 10,000 L, or more. For example, the methods are carried out with a minimum volume of about 1000 L or about 10,000 L or 25,000 L or more cell culture producing AAV.

The methods of producing and purifying AAV described herein are also advantageous, because the methods result in high titer AAV production. In certain embodiments, an AAV product comprising at least about $10^{10}$ virus particles (vp) is produced from about 1000 L of starting material (e.g., cell culture). In certain embodiments, an AAV product comprising at least about $10^{11}$ virus particles (vp) is produced from about 1000 L of starting material (e.g., cell culture). In certain embodiments, an AAV product comprising at least about $10^{12}$ virus particles (vp) is produced from about 1000 L of starting material (e.g., cell culture). In certain embodiments, an AAV product comprising at least about $10^{13}$ virus particles (vp) is produced from about 1000 L of starting material (e.g., cell culture). In certain embodiments, an AAV product comprising at least about $10^{14}$ virus particles (vp) is produced from about 1000 L of starting material (e.g., cell culture). In certain embodiments, an AAV product comprising at least about $10^{15}$ virus particles (vp) is produced from about 1000 L of starting material (e.g., cell culture). In certain embodiments, an AAV product comprising at least about $10^{16}$ virus particles (vp) is produced from about 1000 L of starting material (e.g., cell culture). In certain embodiments, an AAV product comprising at least about $10^{17}$ virus particles (vp) is produced from about 1000 L of starting material (e.g., cell culture). In certain embodiments, an AAV product comprising at least about $2\times10^{16}$ virus particles (vp) is produced from about 1000 L of starting material (e.g., cell culture). In certain embodiments, an AAV product comprising at least about $5\times10^{17}$ virus particles (vp) is produced from about 1000 L of starting material (e.g., cell culture).

Another advantage of the methods described herein is the methods yield a highly pure AAV product. In certain embodiments, the AAV product produced through the methods of the present disclosure is substantially free of one or more contaminants: host cell proteins, host cell nucleic acids (e.g., free host cell DNA and free plasmid DNA), plasmid DNA, empty viral capsids, heat shock protein 70 (HSP70), lactate dehydrogenase (LDH), proteasomes, contaminant non-AAV viruses (e.g., lipid-enveloped viruses), host cell culture components (e.g., antibiotics), *mycoplasma*, pyrogens, bacterial endotoxins, cell debris (e.g., debris composed of membrane lipids, proteins and other biological polymers), and adventitious agents. One or more, or even all of, the following impurities may be undetectable when AAV is purified according to the methods of producing and purifying AAV described herein: histone H2A type 1, histone H2B type 1-B, histone H4, heat shock 70 kDa protein 1A, pyruvate kinase PKM, elongation factor 2, ATP-citrate synthase, histone H1.4, immunoglobulin heavy constant gamma 1 (immobilized ligand from an acidic elution method), 60S ribosomal protein L27, fructose-bisphosphate aldolase A, heat shock cognate 71 kDa protein, cytoplasmic actin 1, S-formylglutathione hydrolase, asparagine synthetase (glutamine hydrolyzing), L-lactate dehydrogenase B chain, tubulin beta-2A chain, X-chromosome RNA-binding motif protein, 60S ribosomal protein L6, cytoplasmic threonine tRNA ligase, immunoglobulin kappa constant, 60S ribosomal protein L30, WD repeat-containing protein 1, adenosylhomocysteinase, heterogeneous nuclear ribonucleoprotein C, protein Rep68, thimet oligopeptidase, D-3-phosphoglycerate dehydrogenase, ATP-dependent molecular chaperone HSC82. Adding an anion exchange step prior to the wash steps, according to methods of producing and purifying anion AAV described herein, can also render the following undetectable: histone H1.4, 60S ribosomal protein L27, cytoplasmic actin 1, tubulin beta-2A chain, 60S ribosomal protein L6, 60S ribosomal protein L30, heterogeneous nuclear ribonucleoprotein C, protein Rep68, and ATP-dependent molecular chaperone HSC82.

In exemplary embodiments, the methods of the present disclosure provide a purified AAV product where at least or about 50% of the contaminant found in the starting material (e.g., cell culture) is removed. In exemplary embodiments, the methods of the present disclosure provide a purified AAV product where at least or about 60% of the contaminant found in the starting material (e.g., cell culture) is removed. In exemplary embodiments, the methods of the present disclosure provide a purified AAV product where at least or about 70% of the contaminant found in the starting material (e.g., cell culture) is removed. In exemplary embodiments, the methods of the present disclosure provide a purified AAV product where at least or about 80% of the contaminant found in the starting material (e.g., cell culture) is removed. In exemplary embodiments, the methods of the present disclosure provide a purified AAV product where at least or about 90% of the contaminant found in the starting material (e.g., cell culture) is removed.

In certain embodiments, the AAV product produced through the methods of the present disclosure is suitable for administration to a human. In certain embodiments, the AAV is a recombinant AAV (rAAV). In certain embodiments, the AAV product produced through the methods of the present disclosure is sterile and/or of good manufacturing practice (GMP) grade. In certain embodiments, the AAV product produced through the methods of the present disclosure conforms to the requirements set forth in the U.S. Pharmacopeia Chapter 1046 or the European Pharmacopoeia on gene therapy medicinal products or as mandated by the U.S. Food and Drug Administration (USFDA) or the European Medicines Agency (EMA).

Additionally, the AAV product produced from the methods described herein are highly potent. The potency of an AAV product, e.g., an AAV8 or AAV9 product, can be described in terms of (1) in vivo biopotency (e.g., production of active protein in mice) which is given as units (FIX or FVIII) per mL of mouse plasma; or (2) in vitro biopotency. The in vitro biopotency test measures the potential of AAV vectors to infect cells, e.g., HepG2 cells, which express and secrete the protein of interest into the medium, and determine the amount by ELISA techniques and/or enzyme activity. Suitable methods of measuring in vivo and in vitro biopotency are known in the art and also described herein.

In further embodiments, the AAV product produced from the methods described herein demonstrate superior specific activity. The "Specific activity" of the AAV is represented by the ratio of qPCR to µg AAV8. In exemplary embodiments, the AAV product produced from the methods described herein demonstrate a superior ratio of vector genomes per µg of AAV demonstrating that the AAV product has a high amount of "full" virus particles. In certain embodiments, the methods of the present disclosure comprise testing an AAV fraction via an AAV-specific ELISA. In certain embodiments, the AAV-specific ELISA is sufficient to provide a representative reading on potency of the AAV fraction, because the majority of capsids in the AAV fraction are full capsids.

Source of rAAV Particles

With regard to the methods of the present disclosure, the AAV may be of any AAV serotype. In certain embodiments, the AAV purified by the methods described herein are of AAV1 serotype, AAV2 serotype, AAV3 serotype, AAV4 serotype, AAV5 serotype, AAV6 serotype, AAV7 serotype, AAV8 serotype, AAV9 serotype, AAV10 serotype, AAV11 serotype, AAV12 serotype, AAV13 serotype, AAAV serotype, BAAV serotype, AAV (VR-195) serotype, and AAV (VR-355) serotype, or chimeric AAV vectors. In certain embodiments, the AAV is wild type. In certain embodiments, the AAV is modified by genetic engineering and/or is chemically modified. In certain embodiments, the AAV comprises a modified capsid, e.g., a genetically engineered or a chemically-modified AAV capsid. In certain embodiments, the AAV particles purified by the methods described herein are of AAV8 serotype.

With regard to the methods of the invention, the AAV fraction is in exemplary aspects a concentrated AAV fraction. In certain embodiments, the AAV fraction comprises at least $1 \times 10^{10}$, $1 \times 10^{11}$ or $1 \times 10^{12}$ AAV capsids per mL. In certain embodiments, the AAV fraction comprises at least $1 \times 10^{12}$ AAV capsids per mL. The AAV capsids may include empty AAV capsids and full AAV capsids.

In certain embodiments, the AAV fraction represents an AAV fraction produced by transfected host cells. In certain embodiments, the AAV fraction represents a supernatant harvested from a cell culture comprising host cells transfected with a triple plasmid system, where one plasmid of the system comprises a gene or cDNA of interest, one plasmid encodes capsid protein VP1, capsid protein VP2 and/or capsid protein VP3. In certain embodiments, VP1, VP2, and/or VP3 are AAV8 VP1, AAV8 VP2, and/or AAV8 VP3. In certain embodiments, VP1, VP2, and/or VP3 are AAV9 VP1, AAV9 VP2, and/or AAV9 VP3. Triple plasmid transfection for purposes of rAAV production is known in the art. See, e.g., Qu et al., 2015, supra, and Mizukami et al., "A Protocol for AAV vector production and purification." PhD dissertation, Division of Genetic Therapeutics, Center for Molecular Medicine, 1998; and Kotin et al., Hum Mol Genet 20(R1): R2-R6 (2011). In certain embodiments, the transfection may be carried out using inorganic compounds, e.g., calcium phosphate, or organic compounds, polyethyleneimine (PEI), or non-chemical means, e.g., electroporation. In certain embodiments, the host cells are adherent cells. In certain embodiments, the host cells are suspension cells. In certain embodiments, the host cells are HEK293 cells or Sf9 cells. In certain embodiments, the cell culture comprises culture medium which is serum and protein free. In certain embodiments, the medium is chemically defined and is free of animal derived components, e.g., hydrolysates. In certain embodiments, the fraction comprising rAAV particles represents a fraction comprising HEK293 cells transfected with a triple plasmid system. In certain embodiments, the fraction comprising rAAV particles is described in U.S. Provisional Application No. 62/417,775 and International Application No. PCT/US2017/059967.

Additional Steps

The methods of the present disclosure comprise any combination of steps disclosed herein, and may optionally be combined with one or more additional steps. Accordingly, in exemplary aspects, the methods of the present disclosure further comprise the step of transfecting host cells with a triple plasmid system as described herein. In exemplary aspects, the methods of the present disclosure comprise harvesting a supernatant from a cell culture comprising host cells, e.g., HEK293 cells, transfected with a triple plasmid system. In exemplary aspects, the transfection and harvesting step occurs prior to the ultracentrifugation step described herein.

The methods of the present disclosure may comprise yet other additional steps, which may further increase the purity of the AAV and remove other unwanted components and/or concentrate the fraction and/or condition the fraction for a subsequent step. The additional steps may occur before or after the ultracentrifugation step described above.

In exemplary aspects, the method comprises a depth filtration step. In exemplary aspects, the method comprises subjecting a fraction of a transfected HEK293 cell culture supernatant to depth filtration using a filter comprising cellulose and perlites and having a minimum permeability of about 500 L/m$^2$. In exemplary aspects, the method further comprises use of a filter having a minimum pore size of about 0.2 µm. In exemplary aspects, the depth filtration is followed by filtration through the filter having a minimum pore size of about 0.2 µm. In exemplary aspects, one or both of the depth filter and filter having a minimum pore size of about 0.2 µm are washed and the washes are collected. In exemplary aspects, the washes are pooled together and combined with the filtrate obtained upon depth filtration and filtration with the filter having a minimum pore size of about 0.2 µm.

In exemplary aspects, the methods of the present disclosure comprise one or more chromatography steps. In exemplary aspects, the methods comprise a negative chromatography step whereby unwanted components bind to the chromatography resin and the desired AAV does not bind to the chromatography resin. In exemplary aspects, the methods comprise a negative anion exchange (AEX) chromatography step, or an AEX chromatography step in the "non-binding mode". Example 2 describes such a step.

Advantages of "non-binding mode" include relative ease of carrying out the procedure and in conducting subsequent assaying.

Accordingly, in exemplary embodiments, the methods of purifying AAV particles comprise performing negative anion exchange (AEX) chromatography on a fraction comprising AAV particles by applying the fraction to an AEX chromatography column or membrane under conditions that allow for the AAV to flow through the AEX chromatography column or membrane and collecting AAV particles. In exemplary aspects, the fraction is applied to the AEX chromatography column or membrane with a loading buffer comprising about 100 mM to about 150 mM salt, e.g., NaCl, optionally, where the pH of the loading buffer is about 8 to about 9. In exemplary aspects, the loading buffer comprises about 115 mM to about 130 mM salt, e.g., NaCl, optionally, where the loading buffer comprises about 120 mM to about 125 mM salt, e.g., NaCl. In exemplary aspects, the negative AEX step occurs prior to the ultracentrifugation step described herein.

In exemplary aspects, the methods of the present disclosure comprise concentrating an AAV fraction using an ultra/diafiltration system. In exemplary aspects, the methods of the present disclosure comprise one more tangential flow filtration (TFF) steps. In exemplary aspects, the AAV fraction undergoes ultra-/dia-filtration. In exemplary aspects, the AAV fraction is concentrated with the ultra/diafiltration system before a step comprising performing negative AEX chromatography, after a step comprising performing negative AEX chromatography, or before and after comprising performing negative AEX chromatography. In exemplary aspects, the TFF steps occur prior to the ultracentrifugation step described herein.

In exemplary aspects, the methods of the present disclosure comprise filtration of a fraction comprising rAAV particles to remove viruses of greater size than the rAAV particles in the fraction.

In exemplary aspects, the methods of the present disclosure comprise one or more quality control steps, e.g., steps to measure the potency or specific activity of the AAV fractions obtained after one or more steps (e.g., after each step) of the process. In exemplary aspects, the methods of the present disclosure comprise an ELISA specific for AAV. In exemplary aspects, the ELISA is a sandwich ELISA. In exemplary aspects, the sandwich ELISA comprises an antibody specific for an AAV epitope. In exemplary aspects, the AAV epitope is a conformational epitope present on assembled AAV capsids. As discussed herein, the ELISA may replace qPCR as a way to determine potency of an AAV fraction. In exemplary aspects, the methods of the present disclosure comprise testing an AAV fraction via an AAV-specific ELISA and the methods do not include a method of measuring potency via quantitative PCR. In exemplary aspects, the AAV-specific ELISA is sufficient to provide a representative reading on potency of the AAV fraction, because the majority of the capsids in the AAV fraction are full capsids.

In exemplary aspects, the methods of the present disclosure comprise an ELISA specific for AAV after one or more of the steps of the present disclosure. In exemplary aspects, the methods of the present disclosure comprise testing an AAV fraction obtained after depth filtration via an AAV-specific ELISA to determine the specific activity of the AAV in that fraction. In exemplary aspects, the methods of the present disclosure comprise testing an AAV fraction obtained after concentrating an AAV fraction using an ultra-/diafiltration system via an AAV-specific ELISA to determine the specific activity of the AAV in that fraction. In exemplary aspects, the methods of the present disclosure comprise testing an AAV fraction obtained after a tangential flow filtration (TFF) step via an AAV-specific ELISA to determine the specific activity of the AAV in that fraction. In exemplary aspects, the methods of the present disclosure comprise testing an AAV fraction obtained after negative anion exchange (AEX) chromatography via an AAV-specific ELISA to determine the specific activity of the AAV in that fraction. In exemplary aspects, the methods of the present disclosure comprise testing an AAV fraction obtained after a polish step via an AAV-specific ELISA to determine the specific activity of the AAV in that fraction.

An AAV product produced by a method of the present disclosures is further provided herein. In exemplary aspects, the AAV product comprises at least about $10^{12}$ virus particles (vp) produced from about 1000 L of starting material (e.g., cell culture) or at least about $10^{13}$ virus particles (vp) produced from about 1000 L of starting material (e.g., cell culture). In exemplary aspects, the AAV product is an empty capsid, generated by transfecting the rep-cap and Ad helper plasmids without the transgene plasmid. Purified empty plasmids can be used to deplete or remove antibodies specific to AAV antigens from the blood of a patient.

In exemplary aspects, the AAV product of the present disclosures is highly pure, highly potent and suitable for clinical use in humans. In exemplary aspects, the AAV product comprises AAV particles of a homogenous population and high purity. In exemplary aspects, the AAV product comprises full-length vector DNA. In exemplary embodiments, the AAV product is substantially free of unwanted contaminants, including but not limited to, AAV particles containing truncated or incomplete vector DNA, AAV particles with incomplete protein composition and oligomerized structures, or contaminating viruses, e.g., non AAV, lipid enveloped viruses. In exemplary embodiments, the AAV product contains a high amount of encoding cDNA of the protein of interest. In exemplary aspects, the AAV product of the present disclosure is suitable for administration to a human. In exemplary aspects, the AAV product is sterile and/or of good manufacturing practice (GMP) grade. In exemplary aspects, the AAV product conforms to the requirements set forth in the U.S. Pharmacopeia Chapter 1046 or the European Pharmacopoeia on gene therapy medicinal products or as mandated by the U.S. Food and Drug Administration (USFDA) or the European Medicines Agency (EMA). In exemplary aspects, the AAV product is a ready-to-use product for direct administration to a human with little to no processing or handling.

The following examples are given merely to illustrate the present invention and not in any way to limit its scope.

Example 1

The following example describes an exemplary method of transfecting a HEK293 cell line with a triple plasmid system to produce rAAV particles comprising a nucleic acid encoding a protein of interest.

Adherent HEK293 cells were grown in suspension conditions in a commercially-available culture medium that is chemically-defined and free of animal-derived components, protein and serum, for example as described in paragraphs [00146]-[00150] of PCT/US2017/059967. The cells were transfected with three plasmids: (1) a helper plasmid, which provides helper viral functions essential for a productive AAV infection, (2) the repcap-plasmid, which carries all information regarding capsid generation, replication and packaging of the virus, and (3) a plasmid containing the gene of interest (GOI), which is packaged into the resulting rAAV particle. The rAAV particles carrying the gene of interest are in the HEK293 cell line over a period of 3-5 days post-transfection.

The supernatant of a transfected HEK293 cell culture was harvested for example as described in paragraphs [00151]-[00155], Table 1 and Table 2 of PCT/US2017/059967. The harvested supernatant was concentrated and conditioned (diafiltered) for example as described in paragraphs [00156]-[00160], Table 3 and Table 4 of PCT/US2017/059967. Negative chromatography was performed on the diafiltered concentrate for example as described in paragraphs [00161]-[00165] and Table 5 of PCT/US2017/059967.

Example 2

AAV8 production was developed in a HEK293 cell line after transfection with a triple plasmid system containing encoding cDNA of the protein of interest and AAV8-. VP1. -VP2 and -VP3. The clarified cell free culture supernatant was concentrated and diafiltrated with Pall Omega T-Series Cassette 100 kDa. The viral particles were loaded onto a membrane adsorber (MustangQ, Pall Part Number XT140MSTGQP05) at nonbinding conditions, i.e. in a solution comprising 125 mM NaCl and 50 mM TrisHCl at pH 8.5. A pH conditioned LOAD was obtained by adjusting the AAV8 containing flow through to a pH range between 7.4 and 7.8 with 25% HCl.

The following test procedure was undertaken. First, a column containing POROS™ CaptureSelect™ AAV8 Affinity Matrix (Cat. No. 195338010; Thermo Fisher) ID 32 mm, with a bed height of 59 mm and a volume 47.45 ml, was equilibrated with at least five column volumes of 20 mM TrisHCl and 150 mM NaCl at pH 7.4. The pH conditioned LOAD was applied onto the column containing POROS™ CaptureSelect™ AAV8 Affinity Matrix (Cat. No. 195338010; Thermo Fisher). The column was then re-equilibrated with five column volumes of 20 mM TrisHCl and 150 mM NaCl at pH 7.4 (optional fourth buffer).

The column was then washed with five column volumes of Wash 1 (W1): 100 mM Sodium Acetate and 0.1% Tween80 at pH 6.0. The column was then washed with five column volumes of Wash 2 (W2): 50 mM TrisHCl and 125 mM NaCl at pH 8.5. The column was then washed with five column volumes of Wash 3 (W3): 50 mM TrisHCl and 50% ethylene glycol at pH 8.5.

Elution was undertaken by applying five column volumes of the following elution buffer to the column: 50 mM TrisHCl, 50% ethylene glycol and 750 mM NaCl, at pH 8.0. Five column volumes of the following secondary elution buffer was then applied to the column: 50 mM TrisHCl, 50% ethylene glycol, and 2000 mM NaCl.

The linear flow rate for the above steps was 60 cm/h.

The following comparative procedure was undertaken. A column containing POROS™ CaptureSelect™ AAV8 Affinity Matrix (Cat. No. 195338010; Thermo Fisher) ID 10 mm, with a bed height of 2.5 mm and a volume 1.96 ml, was equilibrated with at least 10 column volumes of 20 mM TrisHCl and 150 mM NaCl at pH 7.4. The pH conditioned LOAD was applied onto the column containing POROS™ CaptureSelect™ AAV8 Affinity Matrix (Cat. No. 195338010; Thermo Fisher). The column was then re-equilibrated with 10 column volumes of 20 mM TrisHCl and 150 mM NaCl at pH 7.4.

A wash step was performed by using the following TBS buffer 20 mM TrisHCl 150 mM NaCl pH7.4. Instead elution was conducted with 10 column volumes of 100 mM sodium citrate at pH 3.0.

The above test and comparative procedure are described in more detail in Table 2, with "CV" indicating the number of column volumes of solution added in the step.

TABLE 2

| Step | TEST PROCEDURE | CV | COMPARATIVE PROCEDURE | CV | Flowrate |
|---|---|---|---|---|---|
| 1. | 20 mM TrisHCl 150 mM NaCl pH 7.4 | >5 | 20 mM TrisHCl 150 mM NaCl pH 7.4 | >5 | 30 cm/h |
| 2. | Sample-Load pH 7.4 to 7.8 | | Sample-Load pH 7.4 to 7.8 | — | |
| 3. | 20 mM TrisHCl 150 mM NaCl pH 7.4 | 5 | 20 mM TrisHCl 150 mM NaCl pH 7.4 | 10 | |
| 4. | WASH1 (W1) 100 mM NaAcetate 0.1% Tween80 pH 6.0 | 5 | x | x | |
| 5. | WASH2 (W2) 50 mM TrisHCl 125 mM NaCl pH 8.5 | 5 | x | x | |
| 6. | WASH3 (W3) 50 mM TrisHCl 50% Ethylene glycol pH 8.5 | 5 | x | x | 30 cm/h |
| 7, | ELUTION 50 mM Tris 50% Ethylene glycol 750 mM NaCl pH 8.0 | 5 | ELUTION 100 mM Sodium Citrate pH 3.0 | 10 | |

The following assays were conducted with data shown in weight/volume in Table 3. Density of the elution buffer was measured on an oscillating U-tube density meter DMA 4500M (Anton Paar).

ELISA was used to measure the quantity of AAV8 antigen. ELISA was carried out with an AAV-8 titration ELISA Kit (Art. No. PRAAV8; Progen (Heidelberg, Germany) on a TECAN Roboter system. Briefly, a monoclonal antibody specific for a conformational epitope on assembled AAV8 capsids (ADK8) was coated onto microtiter strips and was used to capture AAV8 particles from the AAV fraction. The capture AAV8 particles were detected by two steps. In a first step, a biotin-conjugated monoclonal antibody specific for the ADK8 antibody was bound to the immune complex (of ADK8 and ADK8 antibody). Streptavidin peroxidase conjugates were added to the immune complexes bound to the biotin-conjugated monoclonal antibody and the streptavidin peroxidase conjugates reacted with the biotin. A peroxidase substrate solution was added and a color reaction which is proportional to the amount of bound AAV particles occurs. The color reaction is measured photometrically at 450 nm.

An ITR-qPCR assay was used to determine the genome copy titer by quantifying the inverted tandem repeats found in the vector encoding for the gene of interest (e.g., human Factor VIII or human Factor IX). HEK-HCP is a measurement of the residual host cell protein by ELISA. LDH was determined by a colorimetric activity assay.

AAV8 Ligand Leakage ELISA (Enzyme Linked Immuno-Sorbent Assay) is designed for the detection of 1 ng/mL AAV8 affinity ligand that may be present in product purified with POROS™ CaptureSelect™ AAV8 affinity media, which contains the AAV8 affinity ligand as capturing agent. The AAV8 Ligand Leakage ELISA can be used as a tool to aid in optimal purification process development and in routine quality control of in-process streams as well as final product.

The quantity "Ligand leakage ELISA/AAV8—Antigen" reflects the ratio of "Ligand leakage ELISA" to "AAV8 Antigen" calculated as nanograms of ligand per microgram of AAV8.

In the in-vitro biopotency assay, the viral vector AAV8 infects a hepatic target cell line, which subsequently secretes functional, measurable encoded protein into the medium. In a first step HepG2 target cells are transduced infected by AAV8. During incubation time, encoded protein is released into cell supernatant. In a second step the activity of the encoded protein into the cell culture supernatant is directly measured by a activity assay. The measurement of an AAV8 sample is given as a percentage relative to a reference material. The method allows a quantitative assessment of the biologic function of the AAV8 gene therapy vector.

TABLE 3

|  | Test Procedure | Comparative Procedure |
| --- | --- | --- |
| DENSITY (Elution buffer) | 1.099 | 1.008 g/ml |
| AAV8 Antigen | 211.6 µg/ml | 187.6 µg/ml |
| ITR-qPCR | 1.87E+13 vg/ml | 0.875 + 13 vg/ml |
| HEK-HCP | <91 ng/ml | <99.2 ng/g |
| LDH (Lactate dehydrogenase) | <24.6 | <26.8 ng/g |
| Ligand leakage ELISA | 27.57 ng/ml | 141.9 ng/ml |
| Ligand leakage ELISA/ AAV8-Antigen | 0.13 ng/µg | 0.76 ng/µg |
| STEP Yield | | |
| AAV8 Antigen | 88.8% | 113.9% |
| ITR-qPCR | 105.3% | 71.2% |
| In vitro Biopotency | 0.45 BPU | 0.33 BPU |

The STEP yield for ITR-qPCR for the test procedure was 105.3% while that of the comparative procedure was 71.2%. The in vitro biopotency for the test procedure was 0.45 while that of the comparative procedure was 0.33.

The assays were also conducted with data shown in weight/weight in Table 4.

TABLE 4

|  | Test Procedure | Comparative Procedure |
| --- | --- | --- |
| AAV8 Antigen | 232.6 µg/g | 189.1 µg/g |
| ITR-qPCR | 2.06E+13 vg/g | 0.88E+13 vg/g |
| HEK-HCP | <100 ng/g | <100 ng/g |
| LDH (Lactate dehydrogenase) | <27 ng/g | <27 ng/g |
| Ligand leakage ELISA | 30.3 ng/g | 143.0 ng/g |
| Ligand leakage ELISA/ AAV8-Antigen | 0.13 ng/µg | 0.76 ng/µg |
| STEP Yield | | |
| AAV8 Antigen | 107.4% | 115.8% |
| ITR-qPCR | 127.4% | 72.4% |

The STEP yield for ITR-qPCR for the test procedure was 127.4% while that of the comparative procedure was 72.4%. The improvement in yield and purity, combined with not having to use extreme conditions that would degrade AAV8 infectivity and biopotency was surprising. Also, it was surprising that the test procedure removed most of impurities without also eluting the product from the affinity ligand, especially under conditions where there was substantially greater non-specific binding and complexes of product with impurities that were present before purification.

SDS-PAGE analysis was performed to determine if there was a reduction in Heat Shock Protein 70 kDa (HSP70) when using the test procedure with the wash steps instead of the comparative procedure. A Western Blot was performed using an Anti-Hsp70 antibody (Abcam, catalog no. ab79852) as the primary antibody at 1:2000 dilution for two hours, and goat anti-rabbit igG (H+L) AP conjugate as the secondary antibody (Sigma, catalog no. A8025) in 1:1000 dilution for one hour. The results are shown in FIG. 1. In comparing lane 4 (test procedure) with lane 6 (comparative procedure), a substantial reduction in HSP70 was observed with the test procedure. Lane 2 shows 20 ng of HSP70 and lane 4 shows 4 ng of HSP70.

Figure 2:
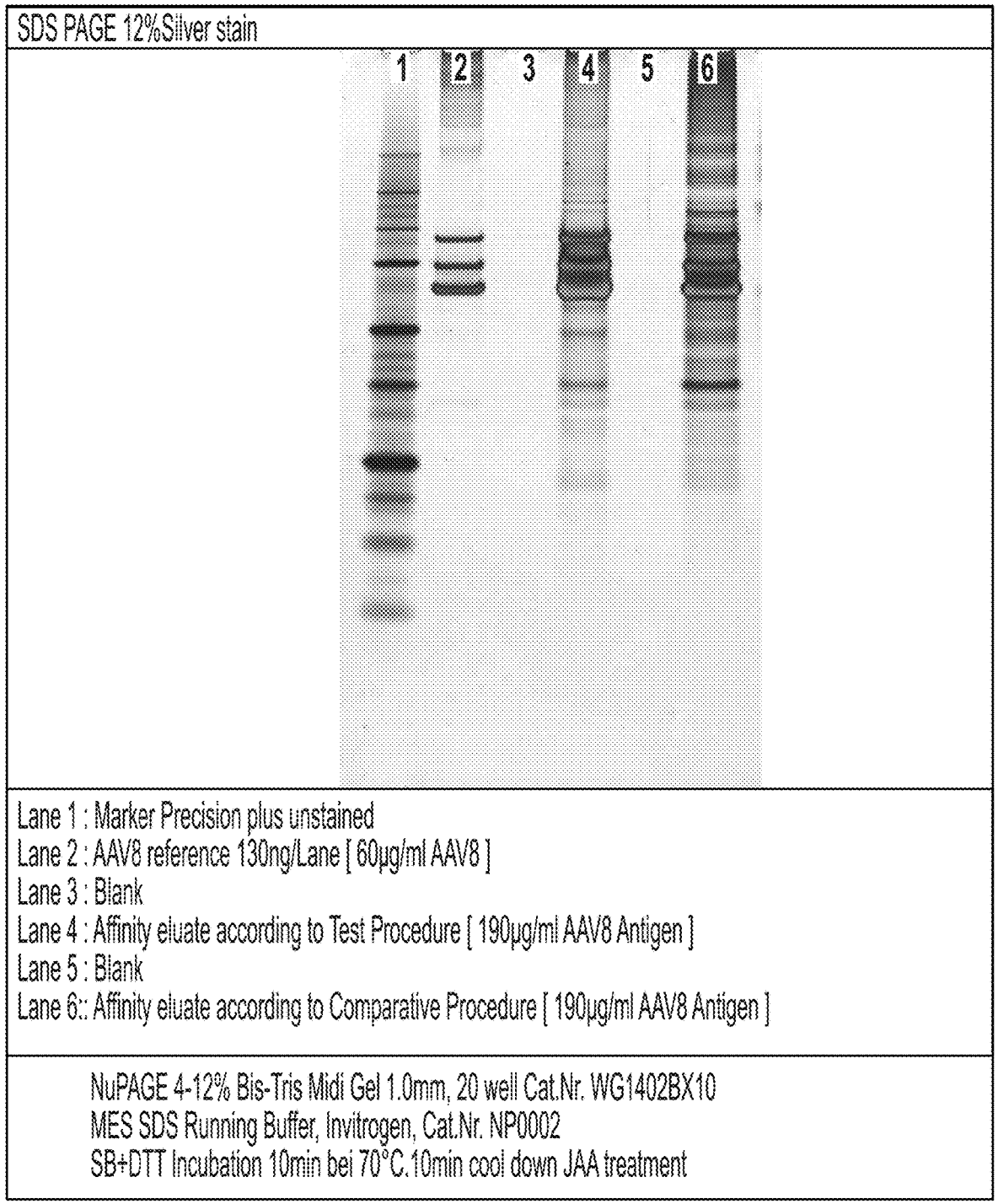
FIG. 2 depicts an SDS-PAGE silver stain gel showing AAV8 proteins in lane 2, the AAV8-containing eluate from the purification protocol with multiple wash steps described herein (lane 4) and a comparative purification protocol without the wash steps (lane 6).

An SDS-PAGE silver stain assay was performed to determine the overall level of impurities present. The results are shown in FIG. 2. Lane 2 represents AAV8 reference and shows three characteristic bands. Eluate (190 µg/ml) was purified according to both the test procedure and the comparative procedure. The results from the test procedure are shown in lane 4. The results of the comparative procedure are shown in lane 6. There are substantially more impurities seen with the comparative procedure than with the test procedure.

A Western Blot with 12% anti-AAV antibody was performed to determine the levels and purity of the AAV8 recovered after purification according to the test and comparative procedures. The Western blot was performed with monoclonal antibodies to VP1, VP2 and VP3 of AAV as the primary antibodies, with goat anti-mouse ALP antibody (Sigma, catalog number A4656) as the secondary antibody. The results are shown in FIG. 3. Lane 2 shows an AAV reference (130 ng, corresponding to 60 µg/ml) with the three bands for each of VP1, VP2 and VP3. Lane 4 shows the eluate according to the test procedure (190 µg/ml AAV8 antigen) and lane 6 shows the eluate according to the comparative procedure. According to the Western blot, the yield is higher with the test procedure versus the comparative procedure.

LC-MS was performed (rp-HPLC-UV-ESI-MS/MS) to determine the identity and amounts of various host cell impurities. The samples were digested using the enzyme trypsin. The resulting peptide mixture was separated on a HPLC system using RP column (ZORBAX 300SB-C18 column, 0.5×150 mm, 3.5 µm), and subsequently, the peptides were analyzed on a Q-Exactive HF mass spectrometer. The data were analyzed using the software Proteome Discoverer to identify the proteins in the sample.

An Agilent HPLC1209 (1200 capHPLC) was used with ChemStation for LC 3D systems (Rev. B.04.03-SP2 (105)). The HPLC method was PEPMAP_CAP_170.M. Eluent A was 0.1% (v/v) HCOOH in deionized water and Eluent B was 0.08% (v/v) HCOOH in Acetonitrile. Details on HPLC are provided in the following Table 5:

TABLE 5

| | |
| --- | --- |
| HPLC-Skid: | HPLC1209: 1200 capHPLC, Agilent |
| Software: | ChemStation for LC 3D systems Rev. B.04.03-SP2 (105) |
| HPLC-Method: | PEPMAP_CAP_170.M |

TABLE 5-continued

| | | | | |
|---|---|---|---|---|
| Column: | ZORBAX 3005B-C18 0.5 × 150 mm, 3.5 µm | | | |
| | Part. No. 5064-8268 Ser. No. USHTC01001 Lot No. WSB1432005 | | | |
| Eluent A: | 0.1% (v/v) HCOOH in deionized water, Lot 140617/01/DF3376/028 | | | |
| Eluent B: | 0.08% (v/v) HCOOH in Acetonitrile, Lot 250117/02/DF3270/015 | | | |
| Pump: | Initial Conditions: | 15 µl/min (micro flow) 100% A | | |
| | Gradient: | 0 min | 100% A | 0% B |
| | | 110 min | 60% A | 40% B |
| | | 125 min | 30% A | 70% B |
| | | 135 min | 0% A | 100% B |
| | | 140 min | 100% A | 0% B |
| | | Stop 170 min | | |
| Autosampler: | Inject volume: | Various injection volumes | | |
| | Temperature: | 4° C. | | |
| | Contact Closure | Initial OPEN | | |
| | | 0.02 min A-CLOSED | | |
| | | 0.5 min A-OPEN | | |
| Column Compartment: | Temperatur: | 40° C. | | |
| DAD-Detektor: | Wavelenghts | 214, 280, 260 nm, Spectrum 190-500 nm | | |
| Needle Wash | Flushport | 55 sec (20% Isopropanol/80% H2O) | | |

Details on the MS are provided in the following Table 6:

TABLE 6

| | | |
|---|---|---|
| Skid: | Q Exactive HF #2 with heated electrospray ionization (HESI), Serial No. 05161L Thermo, Source: HESI-II | |
| Software: | Thermo Xcalibur 3.1.66.10 | |
| Tune Method: | high_parameters.mstune | |
| | Parameter | |
| | Sheath gas flow rate | 7 |
| | Aux gas flow rate | 0 |
| | Sweep gas flow rate | 0 |
| | Spray voltage | 3 kV |
| | Capillary Temperature | 275° C. |
| | S-lens RF | 50 |
| Instrument Method : | 170406_PEPMAP_TOP10_120k_CAP_140.meth | |
| | Parameter | |
| | FULL MS | |
| | Runtime | 140 min |
| | In-source CID | 0.0 eV |
| | Default charge state | 2 |
| | Microscans | 1 |
| | Resolution | 120,000 |
| | AGC target | 3e6 |
| | Maximum IT | 60 |
| | Number of scan ranges | 1 |
| | Scan range | 300-2000 m/z |
| | Spectrum data type | profile |
| | Polarity | positive |
| | dd-MS$^2$ | |
| | Microscans | 1 |
| | Resolution | 30,000 |
| | AGC target | 1e5 |
| | Maximum IT | 100 ms |
| | Loop count | 10 |
| | MSX count | 1 |
| | TopN | 10 |
| | Isolation window | 2.0 m/z |
| | Isolation offset | 0.0 m/z |
| | NCE/stepped | 27 |
| | Spectrum data type | centroid |
| | Underfill ratio | 0.6% |
| | Intensity threshold | 1.0e3 |
| | Apex trigger | OFF |
| | Charge exclusion | unassigned, 1, 7, 8, >8 |
| | Peptide match | preferred |
| | Exclude isotopes | on |
| | Dynamic exclusion | 30 s |
| MS Calibration/Test Resolution: | Calibration solution Pierce LTQ Velos ESI Positive Ion Calibration Solution Order-No. 88323, Lot RF231587 | |
| | Basis parameter | |
| | Tune File: | Calibration_pos_parameters_150818 |
| | Flow Syringe Pump: | 5 µl/ |

TABLE 6-continued

| | |
|---|---|
| TIC Stability: | <10% |
| IT (Injection Time): | <10 ms |
| Ion Mode: | positive |
| Calibration parameter | |
| eFT Parameters (positive) | okay |
| Analyzer Accuracy (positive) | okay |
| Mass calibration (positive) | okay |
| Test-Spectrum/Resolution | |
| 1. Calibration solution | |
| Resolution: | FTMS 120000 (at m/z 200) |
| Mass Range: | m/z 135-1800 |
| AGC Target: | 3e6 |
| Number of scans: | 50 scans |
| Filename: 170621_Calmix.raw | |
| 2. m/z 524 MRFA (Komponente Kalibriermix) | |
| Resolution: | FTMS 120000 (at m/z 200) |
| Mass Range: | m/z 520-530 |
| AGC Target: | 1e5: |
| Number of scans 50 scans | |
| Filename: 170621_MRFA.raw | |
| Resolution (m/z 524) 83281 (80000 Benchmark) | |
| Counts: 1.67 × 10^7 | |

Three different modes of purification were undertaken. One included the comparative procedure of this example, another included the test procedure of this example (that included the anion exchange purification by MustangQ before affinity purification), and a third was conducted according to the test procedure but without the anion exchange purification by MustangQ. Table 7 below summarizes the overall results.

TABLE 7

| | Comparative Procedure | Test Procedure with Prior Anion Exchange Step | Test Procedure without Prior Anion Exchange Step |
|---|---|---|---|
| Purity (AAV8 Capsid proteins) | 95.5% | 99.0% | 96.0% |
| Number of identified protein impurities | 20 | 4 | 14 |

In the above table, the purity reflects the percent area under the curve (AUC) associated with AAV8 capsids relative to the total AUC of all proteins.

The following Tables 8-10 list, for each protein, the AUC value and number of peptides identified by L/MS for the comparative procedure (Table 8), the test procedure with prior anion exchange (Table 9), and test procedure without prior anion exchange (Table 10).

TABLE 8

| Comparative Procedure | | |
|---|---|---|
| Protein | Area [%] | #Peptides |
| Capsid protein AAV8 | 95.5 | 36 |
| Glyceraldehyde-3-phosphate dehydrogenase | 1.4 | 11 |
| Histone H2A type 1 | — | — |
| Histone H2B type 1-B | — | — |
| Histone H4 | — | — |
| Heat shock 70 kDa protein 1A | 0.4 | 14 |
| Acidic leucine-rich nuclear phosphoprotein 32 family member A/B | 0.2 | 2 |

TABLE 8-continued

| Comparative Procedure | | |
|---|---|---|
| Protein | Area [%] | #Peptides |
| Pyruvate kinase PKM | 0.3 | 17 |
| 40S ribosomal protein S7 | — | — |
| Probable ATP-dependent RNA helicase DDX5 | 0.1 | 7 |
| Elongation factor 2 | 0.2 | 13 |
| ATP-citrate synthase | 0.1 | 9 |
| Histone H1.4 | — | — |
| Immunoglobulin heavy constant gamma 1 | 0.1 | 3 |
| 60S ribosomal protein L27 | — | — |
| Fructose-bisphosphate aldolase A | 0.1 | 3 |
| Heat shock cognate 71 kDa protein | 0.1 | 7 |
| Actin, cytoplasmic 1 | — | — |
| S-formylglutathione hydrolase | 0.1 | 6 |
| Asparagine synthetase [glutamine-hydrolyzing] | 0.1 | 6 |
| L-lactate dehydrogenase B chain | 0.1 | 2 |
| Tubulin beta-2A chain | — | — |
| RNA-binding motif protein, X chromosome | 0.1 | 2 |
| 60S ribosomal protein L6 | — | — |
| Threonine--tRNA ligase, cytoplasmic | 0.1 | 6 |
| Immunoglobulin kappa constant | 0.1 | 2 |
| 60S ribosomal protein L30 | — | — |
| WD repeat-containing protein 1 | 0.1 | 4 |
| Adenosylhomocysteinase | 0.1 | 3 |
| Heterogeneous nuclear ribonucleoprotein C | — | — |
| Protein Rep68 | — | — |
| Thimet oligopeptidase | 0.02 | 2 |
| D-3-phosphoglycerate dehydrogenase | 0.02 | 3 |
| ATP-dependent molecular chaperone HSC82 | — | — |
| Other peptides-Score 0 | 0.8 | — |

TABLE 9

Test Procedure with prior Anion Exchange

| Protein | Area [%] | #Peptides |
|---|---|---|
| Capsid protein AAV8 | 99.0 | 36 |
| Glyceraldehyde-3-phosphate dehydrogenase | 0.2 | 5 |
| Histone H2A type 1 | — | — |
| Histone H2B type 1-B | — | — |
| Histone H4 | — | — |
| Heat shock 70 kDa protein 1A | — | — |
| Acidic leucine-rich nuclear phosphoprotein 32 family member A/B | 0.2 | 4 |
| Pyruvate kinase PKM | — | — |
| 40S ribosomal protein S7 | 0.3 | 3 |
| Probable ATP-dependent RNA helicase DDX5 | 0.1 | 3 |
| Elongation factor 2 | — | — |
| ATP-citrate synthase | — | — |
| Histone H1.4 | — | — |
| Immunoglobulin heavy constant gamma 1 | — | — |
| 60S ribosomal protein L27 | — | — |
| Fructose-bisphosphate aldolase A | — | — |
| Heat shock cognate 71 kDa protein | — | — |
| Actin, cytoplasmic 1 | — | — |
| S-formylglutathione hydrolase | — | — |
| Asparagine synthetase [glutamine-hydrolyzing] | — | — |
| L-lactate dehydrogenase B chain | — | — |
| Tubulin beta-2A chain | — | — |
| RNA-binding motif protein, X chromosome | — | — |
| 60S ribosomal protein L6 | — | — |
| Threonine--tRNA ligase, cytoplasmic | — | — |
| Immunoglobulin kappa constant | — | — |
| 60S ribosomal protein L30 | — | — |
| WD repeat-containing protein 1 | — | — |
| Adenosylhomocysteinase | — | — |
| Heterogeneous nuclear ribonucleoprotein C | — | — |
| Protein Rep68 | — | — |
| Thimet oligopeptidase | — | — |
| D-3-phosphoglycerate dehydrogenase | — | — |
| ATP-dependent molecular chaperone HSC82 | — | — |
| Other peptides-Score 0 | 0.3 | — |

TABLE 10

Test Procedure without prior Anion Exchange

| Protein | Area [%] | #Peptides |
|---|---|---|
| Capsid protein AAV8 | 96.0 | 39 |
| Glyceraldehyde-3-phosphate dehydrogenase | 0.1 | 4 |
| Histone H2A type 1 | 1.3 | 2 |
| Histone H2B type 1-B | 0.9 | 3 |
| Histone H4 | 0.8 | 4 |
| Heat shock 70 kDa protein 1A | — | — |
| Acidic leucine-rich nuclear phosphoprotein 32 family member A/B | 0.2 | 7 |
| Pyruvate kinase PKM | — | — |
| 40S ribosomal protein S7 | — | — |
| Probable ATP-dependent RNA helicase DDX5 | — | — |
| Elongation factor 2 | — | — |
| ATP-citrate synthase | — | — |
| Histone H1.4 | 0.1 | 2 |
| Immunoglobulin heavy constant gamma 1 | — | — |
| 60S ribosomal protein L27 | 0.1 | 2 |
| Fructose-bisphosphate aldolase A | — | — |
| Heat shock cognate 71 kDa protein | — | — |
| Actin, cytoplasmic 1 | 0.1 | 5 |
| S-formylglutathione hydrolase | — | — |
| Asparagine synthetase [glutamine-hydrolyzing] | — | — |
| L-lactate dehydrogenase B chain | — | — |
| Tubulin beta-2A chain | 0.1 | 4 |
| RNA-binding motif protein, X chromosome | — | — |
| 60S ribosomal protein L6 | 0.1 | 2 |
| Threonine--tRNA ligase, cytoplasmic | — | — |
| Immunoglobulin kappa constant | — | — |
| 60S ribosomal protein L30 | 0.1 | 2 |
| WD repeat-containing protein 1 | — | — |
| Adenosylhomocysteinase | — | — |
| Heterogeneous nuclear ribonucleoprotein C | 0.03 | 2 |
| Protein Rep68 | 0.03 | 3 |
| Thimet oligopeptidase | — | — |
| D-3-phosphoglycerate dehydrogenase | — | — |
| ATP-dependent molecular chaperone HSC82 | 0.02 | 1 |
| Other peptides-Score 0 | 0.3 | — |

The fewest proteins were detected with the test procedure coupled with prior anion exchange. Without anion exchange the purity is reduced and the number of detected proteins increases. The lowest purity and the greatest number of detected proteins is seen with the comparative procedure.

Example 3

AAV8 production was developed in a HEK293 cell line after transfection with a triple plasmid system containing encoding cDNA of the protein of interest and AAV8-. VP1. -VP2 and -VP3. The clarified cell free culture supernatant was concentrated and diafiltrated with Pall Omega T-Series Cassette 100 kDa. The viral particles were loaded onto a membrane adsorber (MustangQ. Pall Part Number XT140MSTGQP05) at nonbinding conditions. The obtained AAV8 containing flow through was not pH adjusted to a pH range between 7.4 and 7.8 with 25% HCl. Instead, a LOAD was formed by reconstituting the AAV-8 containing flow through in a load buffer comprising 125 mM NaCl and 50 mM TrisHCl at a pH of 8.5.

Besides the advantage inherent in not having to include a pH adjustment step, having pH 8.5 allows for improved robustness in affinity performance and prevention of unspecific binding of impurities to either the product or resin.

Samples from the various wash and elution steps were taken at various points to assay how much AAV8 was present in the sample. The assays indicate how much AAV8 was lost in various wash steps. The following test procedure was undertaken. First, a column containing POROS™ CaptureSelect™ AAV8 Affinity Matrix (Cat. No. 195338010.

Thermo Fisher) ID 10 mm, with a bed height of 25 mm and a volume 1.96 ml, was equilibrated with at least five column volumes of 20 mM TrisHCl and 150 mM NaCl at pH 7.4. The LOAD was applied onto the column containing POROS™ CaptureSelect™ AAV8 Affinity Matrix (Cat. No. 195338010. Thermo Fisher). A portion of the sample loaded onto the column was saved and later assayed by ITR qPCR, ELISA against AAV antigens, and ELISA against HEK293 HCP antigens. The column was then re-equilibrated with 10 column volumes of 20 mM TrisHCl and 150 mM NaCl at pH 7.4. A sample of the flow through was saved and later assayed by ITR qPCR, ELISA against AAV antigens, and ELISA against HEK293 HCP antigens.

The column was then washed with 10 column volumes of Wash 1 (W1): 100 mM Sodium Acetate and 0.1% Tween80 at pH 6.0. The column was then washed with 10 column volumes of Wash 2 (W2): 50 mM TrisHCl and 125 mM NaCl at pH 8.5. The column was then washed with 10 column volumes of Wash 3 (W3): 50 mM TrisHCl and 50% ethylene glycol at pH 8.5. A sample from eluate of each of W1, W2 and W3 was taken and assayed according to ITR qPCR, ELISA against AAV antigens, and ELISA against HEK293 HCP antigens.

Elution was undertaken by applying 10 column volumes of the following elution buffer to the column: 50 mM TrisHCl, 50% ethylene glycol and 750 mM NaCl, at pH 8.0.

The above test procedure is described in more detail in Table 11.

TABLE 11

| Step | High pH LOAD | CV | Flowrate |
|---|---|---|---|
| 1. | 20 mM TrisHCl<br>150 mM NaCl<br>pH 7.4 | >5 | 30 cm/h |
| 2. | Sample-Load<br>pH 8.5 | | |
| 3 | 20 mM TrisHCl<br>150 mM NaCl<br>pH 7.4 | 10 | |
| 4. | 100 mM NaAcetat<br>0.1% Tween80<br>pH 6.0 | 10 | |
| 5. | 50 mM TrisHCl<br>125 mM NaCl<br>pH 8.5 | 10 | |
| 6. | 50 mM TrisHCl<br>50% Ethylene glycol<br>pH 8.5 | 10 | 30 cm/h |
| 7. | ELUTION<br>50 mM TrisHCl<br>50% Ethylene glycol<br>750 mM NaCl<br>pH 8.0 | 10 | |
| 8. | 50 mM TrisHCl<br>50% Ethylene glycol<br>2000 mM NaCl<br>pH 8.0 | 10 | |

The samples taken were assayed by each of ITR qPCR, ELISA against AAV antigens and ELISA against HEK293 HCP to assess yield and whether losses may have occurred in the steps. Table 12 shows the distribution of AAV8 assayed by ITR qPCR in all of the fractions of wash, elution and post-elution steps listed in Table 11.

TABLE 12

| Sample | Volume (g) | ITR qPCR (vg/mL) × $10^{11}$ | ITR qPCR Total(vg) × $10^{11}$ | ITR qPCR Yield (%) |
|---|---|---|---|---|
| Load Sample (see step 2 in Table 11) | 285.67 | 9.76 | 2788.14 | 100.00% |
| Sample from flowthrough of reequilibration (see step 3 in Table 11) | 316.93 | 0.289 | 91.59 | 3.29% |
| Sample from Wash 1 (see step 4 in Table 11) | 16.99 | 0.655 | 11.13 | 0.40% |
| Sample from Wash 2 (step 5 in Table 11) | 19.45 | 1.18 | 22.95 | 0.82% |
| Sample from Wash 3 (step 6 in Table 11) | 20.71 | 0.162 | 3.36 | 0.12% |
| Sample from Elution (step 7 in Table 11) | 20.93 | 155.00 | 3244.15 | 116.36% |
| Sample from Stripping (step 8 in Table 11) | 23.52 | 13.00 | 305.76 | 10.97% |

The following Table 13 shows the distribution of AAV8 assayed by ELISA in all of the fractions of wash, elution and post-elution steps listed in Table 11.

TABLE 13

| Sample | Volume (g) | AAV ELISA (pg/mL) × $10^{11}$ | AAV ELISA Total(µg) | AAV ELISA Yield (%) |
|---|---|---|---|---|
| Load Sample (step 2 in Table 11) | 285.67 | 28.41 | 8115.885 | 100.00% |
| Sample from flowthrough of reequilibration (step 3 in Table 11) | 316.93 | 0.475 | 150.542 | 1.85% |
| Sample from Wash 1 (step 4 in Table 11) | 16.99 | 0.688 | 11.689 | 0.14% |
| Sample from Wash 2 (step 5 in Table 11) | 19.45 | 1.201 | 23.359 | 0.29% |
| Sample from Wash 3 (step 6 in Table 11) | 20.71 | 0.157 | 3.251 | 0.04% |
| Sample from Elution (step 7 in Table 11) | 20.93 | 211.897 | 4435.004 | 54.65% |
| Sample from Stripping (step 8 in Table 11) | 23.52 | 15.014 | 353.13 | 4.35% |

The following Table 14 shows results of assays to determine the amount of HEK 293 HOP present by ELISA in the LOAD and eluate steps only.

TABLE 14

| Sample | Volume (g) | HEK293 HCP ELISA (µg/mL) × $10^{11}$ | HEK293 HCP ELISA Total (µg) | HEK293 HCP ELISA Yield (%) |
|---|---|---|---|---|
| Load Sample (step 2 in Table 11) | 285.67 | 191.06 | 54580.1 | 100.00% |

TABLE 14-continued

| Sample | Volume (g) | HEK293 HCP ELISA (μg/mL) × $10^{11}$ | HEK293 HCP ELISA Total (μg) | HEK293 HCP ELISA Yield (%) |
|---|---|---|---|---|
| Sample from flowthrough of reequilibration (step 3 in Table 11) | 316.93 | — | — | — |
| Sample from Wash 1 (step 4 in Table 11) | 16.99 | — | — | — |
| Sample from Wash 2 (step 5 in Table 11) | 19.45 | — | — | — |
| Sample from Wash 3 (step 6 in Table 11) | 20.71 | — | — | — |
| Sample from Elution (step 7 in Table 11) | 20.93 | <0.10 | <2.09 | <0.004% |
| Sample from Stripping (step 8 in Table 11) | 23.52 | — | — | — |

Figure 6:
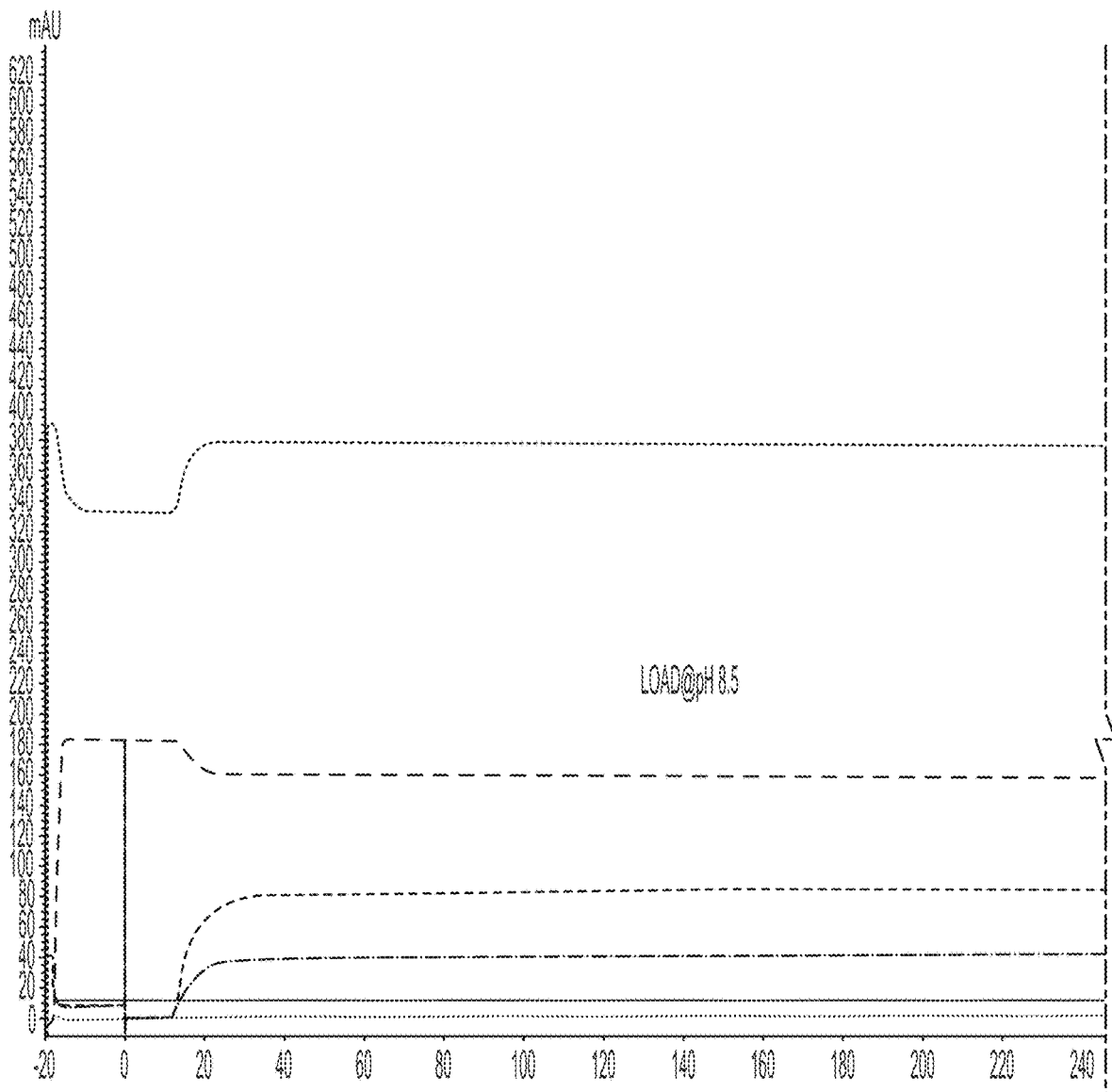
FIG. 6 depicts the chromatogram of the separation procedure according to Example 3.
Figure 6:
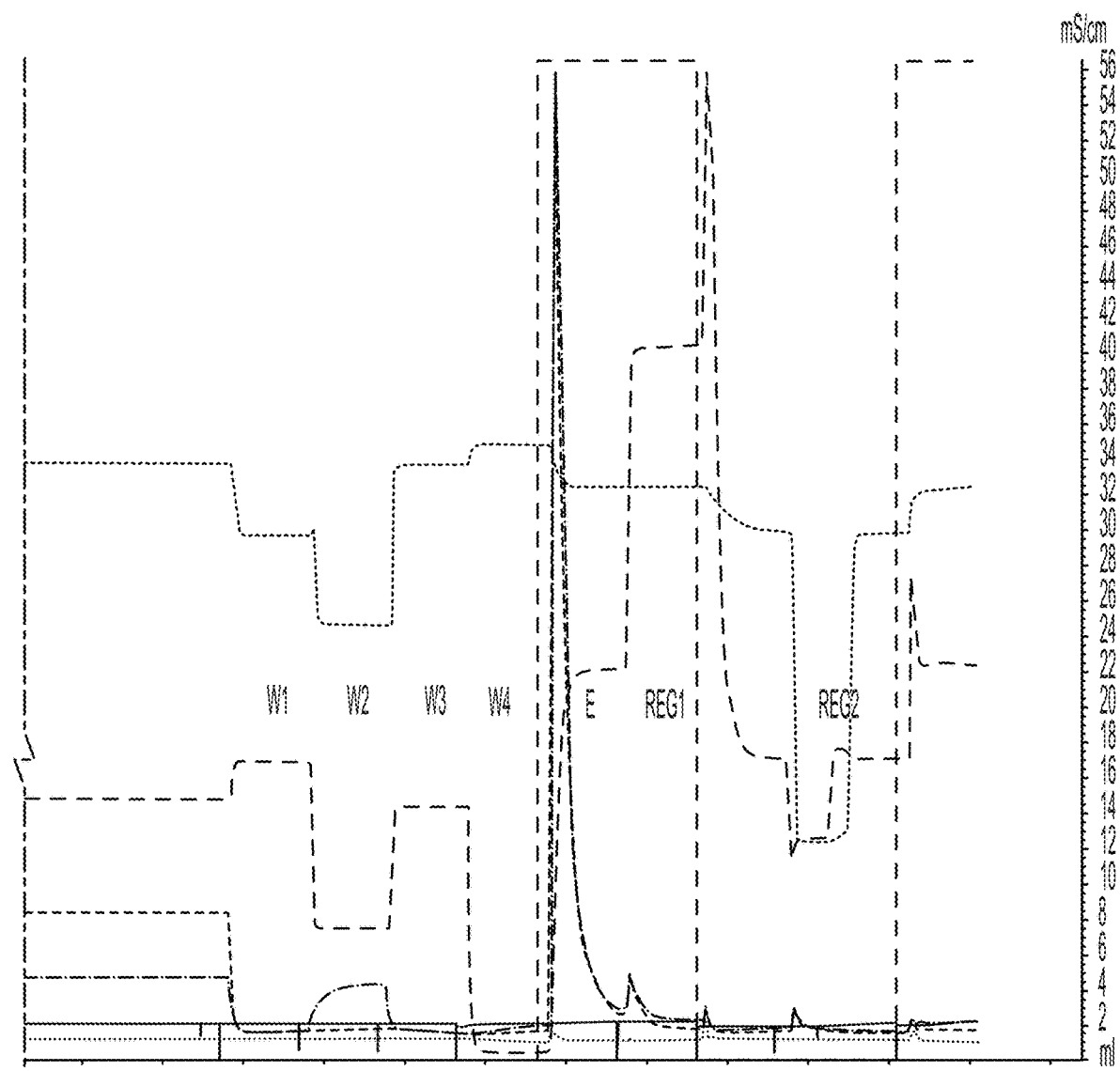

The chromatogram associated with the data in Tables 12-14 is shown in FIG. 6.

Figure 4:
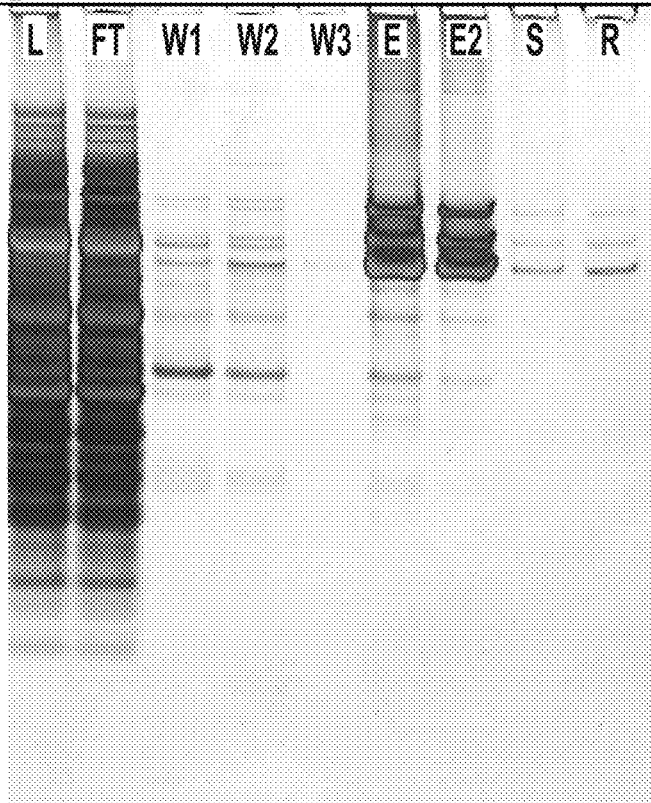
FIG. 4 depicts an SDS-PAGE silver stain gel showing the proteins present in various fractions from (L) initial loading of cell culture media from HEK 293 cells expressing AAV8, to the eluate (E) enriched in AAV8. There was little loss of AAV8 in flowthrough from wash steps (W1, W2, and W3) and little AAV8 eluted from the column during stripping (S).

Samples above were also assayed by SDS-PAGE and 12% silver stain to detect total protein. The results are shown in FIG. 4 with the label for each lane indicated within the figure. The AAV8 bands are clearly visible in the eluate (E) and 50% eluate dilution (E2) lanes. Very little AAV8 is seen in the wash band flow through samples (W1, W2 and W3) and in the stripping (S) flow through samples. Thus, the method efficiently removes AAV8 without substantial losses during washing or having AAV8 remain on the column after elution.

Figure 5:
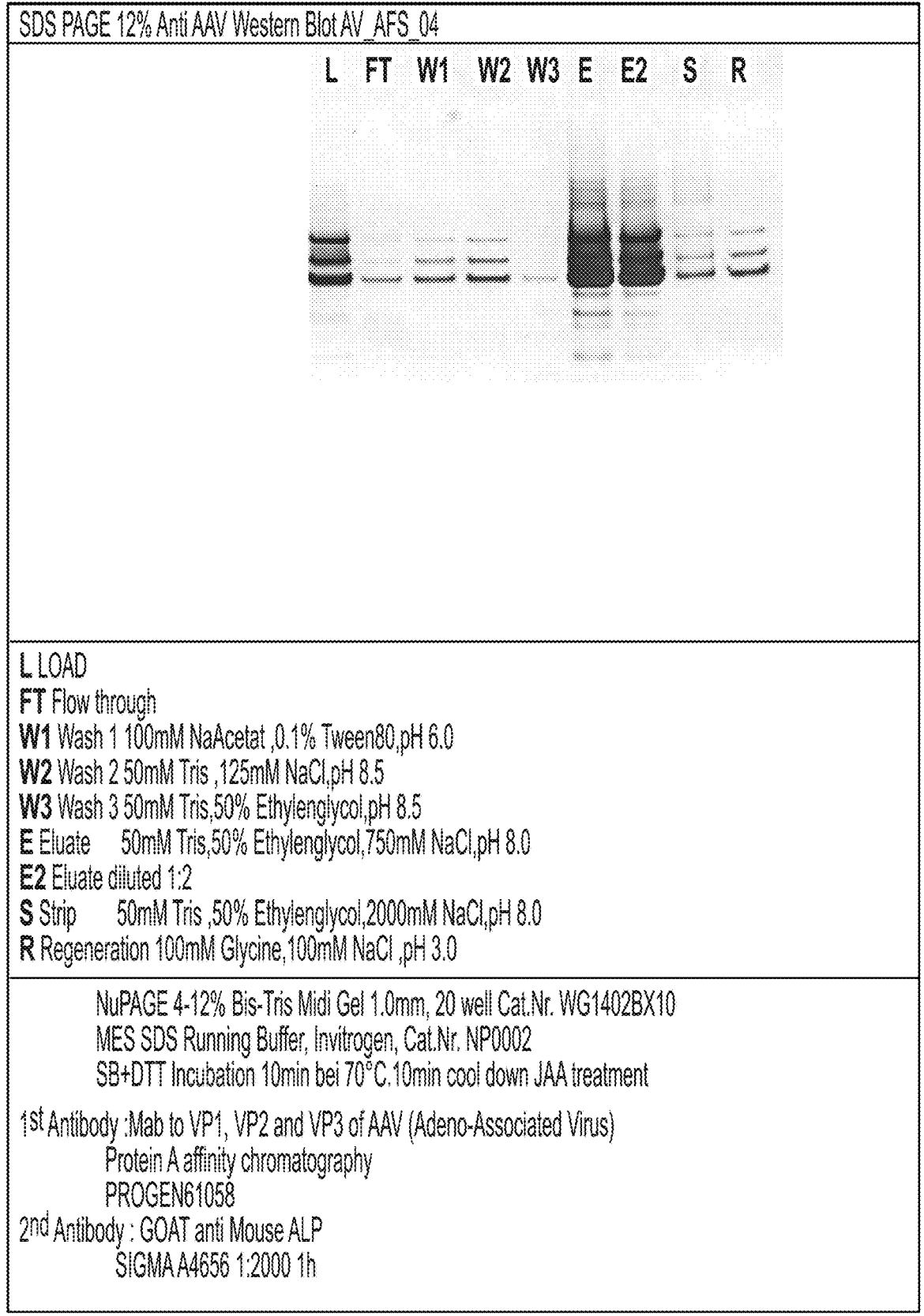
FIG. 5 depicts a Western Blot against AAV8 antigens. AAV8 was expressed in the initial loading of cell culture media from HEK 293 cells expressing AAV8 (L). Substantially less AAV8 was present in the flowthrough from that initial loading (FT) and the subsequent wash steps (W1, W2 and W3). AAV8 was present in the eluate (E, E2). Again, substantially less AAV8 eluted from the column during stripping (S).

Samples were then assayed by SDS-PAGE and a Western blot against AAV antigens. The primary antibodies are monoclonal antibodies against VP1, VP2 and VP3 of AAV while the secondary antibody is a goat anti-mouse coupled with alkaline phosphatase. The results are shown in FIG. 5 with the same labels for each lane used as in FIG. 4. The losses of AAV8 in the washing and stripping steps are minimal.

Example 4

AAV9 production is developed in a HEK293 cell line after transfection with a triple plasmid system containing encoding cDNA of the protein of interest and AAV9-. VP1. -VP2 and -VP3. The clarified cell free culture supernatant is concentrated and diafiltrated with Pall Omega T-Series Cassette 100 kDa. The viral particles are loaded onto a membrane adsorber (MustangQ; Pall Part Number XT140MSTGQP05) at nonbinding conditions, i.e. in a solution comprising 125 mM NaCl and 50 mM TrisHCl at pH 8.5. A pH conditioned LOAD is obtained by adjusting the AAV9 containing flow through to a pH range between 7.4 and 7.8 with 25% HCl.

The following test procedure is undertaken. First, a column containing POROS™ CaptureSelect™ AAV9 Affinity Resin (Cat. No. A27354; Thermo Fisher) ID 32 mm, with a bed height of 59 mm and a volume 47.45 ml, is equilibrated with at least five column volumes of 20 mM TrisHCl and 150 mM NaCl at pH 7.4. The pH conditioned LOAD is applied onto the column containing POROS™ CaptureSelect™ AAV9 Affinity Resin (Cat. No. A27354; Thermo Fisher). The column is then re-equilibrated with five column volumes of 20 mM TrisHCl and 150 mM NaCl at pH 7.4 (optional fourth buffer).

The column is then washed with five column volumes of Wash 1 (W1): 100 mM Sodium Acetate and 0.1% Tween80 at pH 6.0. The column is then washed with five column volumes of Wash 2 (W2): 50 mM TrisHCl and 125 mM NaCl at pH 8.5. The column is then washed with five column volumes of Wash 3 (W3): 50 mM TrisHCl and 50% ethylene glycol at pH 8.5.

Elution is undertaken by applying five column volumes of the following elution buffer to the column: 50 mM TrisHCl, 50% ethylene glycol and 750 mM NaCl, at pH 8.0. Five column volumes of the following secondary elution buffer is then applied to the column: 50 mM TrisHCl, 50% ethylene glycol, and 2000 mM NaCl.

The linear flow rate for the above steps is 60 cm/h.

The following comparative procedure is undertaken. A column containing POROS™ CaptureSelect™ AAV9 Affinity Resin (Cat. No. A27354; Thermo Fisher) ID 10 mm, with a bed height of 2.5 mm and a volume 1.96 ml, is equilibrated with at least 10 column volumes of 20 mM TrisHCl and 150 mM NaCl at pH 7.4. The pH conditioned LOAD is applied onto the column containing POROS™ CaptureSelect™ AAV9 Affinity Resin (Cat. No. A27354; Thermo Fisher). The column is then re-equilibrated with 10 column volumes of 20 mM TrisHCl and 150 mM NaCl at pH 7.4.

A wash step is performed by using the following TBS buffer: 20 mM TrisHCl/150 mM NaCl/pH 7.4. Instead elution is conducted with 10 column volumes of 100 mM sodium citrate at pH 3.0.

The above test and comparative procedure are described in more detail in Table 15, with "CV" indicating the number of column volumes of solution added in the step.

TABLE 15

| Step | TEST PROCEDURE | CV | COMPARATIVE PROCEDURE | CV | Flowrate |
|---|---|---|---|---|---|
| 1. | 20 mM TrisHCl 150 mM NaCl pH 7.4 | >5 | 20 mM TrisHCl 150 mM NaCl pH 7.4 | >5 | 30 cm/h |
| 2. | Sample-Load pH 7.4 to 7.8 | | Sample-Load pH 7.4 to 7.8 | — | |
| 3. | 20 mM TrisHCl 150 mM NaCl pH 7.4 | 5 | 20 mM TrisHCl 150 mM NaCl pH 7.4 | 10 | |
| 4. | WASH1 (W1) 100 mM NaAcetate 0.1% Tween80 pH 6.0 | 5 | x | x | |
| 5. | WASH2 (W2) 50 mM TrisHCl 125 mM NaCl pH 8.5 | 5 | x | x | |
| 6. | WASH3 (W3) 50 mM TrisHCl 50% Ethylene glycol pH 8.5 | 5 | x | x | |
| 7. | ELUTION 50 mM Tris 50% Ethylene glycol 750 mM NaCl pH 8.0 | 5 | ELUTION 100 mM Sodium Citrate pH 3.0 | 10 | 30 cm/h |

50% Ethylene glycol weight/weight in all buffer (w/w)

Density of the elution buffer is measured on an oscillating U-tube density meter DMA 4500M (Anton Paar).

ELISA is used to measure the quantity of AAV9 antigen. ELISA is carried out with an AAV-9 titration ELISA Kit (Art. No. PRAAV9; Progen (Heidelberg, Germany) on a TECAN Roboter system. Briefly, amonoclonal antibody specific for a conformational epitope on assembled AAV9 capsids (ADK9) is coated onto microtiter strips and is used to capture AAV9 particles from the AAV fraction. The capture AAV9 particles are detected by two steps. In a first step, a biotin-conjugated monoclonal antibody specific for the ADK9 antibody is bound to the immune complex (of ADK9 and ADK9 antibody). Streptavidin peroxidase conjugates are added to the immune complexes bound to the biotin-conjugated monoclonal antibody and the streptavidin peroxidase conjugates react with the biotin. A peroxidase substrate solution is added and a color reaction which is proportional to the amount of bound AAV particles occurs. The color reaction is measured photometrically at 450 nm.

An ITR-qPCR assay is used to determine the genome copy titer by quantifying the inverted tandem repeats found in the vector encoding for the gene of interest (e.g., human Factor VIII or human Factor IX). HEK-HCP is a measurement of the residual host cell protein by ELISA. LDH is determined by a colorimetric activity assay.

AAV9 Ligand Leakage ELISA (Enzyme Linked Immuno-Sorbent Assay) can detect 1 ng/mL AAV9 affinity ligand that may be present in product purified with POROS™ CaptureSelect™ AAV9 affinity media, which contains the AAV9 affinity ligand as capturing agent. The AAV9 Ligand Leakage ELISA can be used as a tool to aid in optimal purification process development and in routine quality control of in-process streams as well as final product. The quantity "Ligand leakage ELISA/AAV9—Antigen" reflects the ratio of "Ligand leakage ELISA" to "AAV9 Antigen" calculated as nanograms of ligand per microgram of AAV9.

In the in-vitro biopotency assay, the viral vector AAV9 infects a hepatic target cell line, which subsequently secretes functional, measurable encoded protein into the medium. In a first step HepG2 target cells are transduced infected by AAV9. During incubation time encoded protein is released into cell supernatant. In a second step the activity of the encoded protein into the cell culture supernatant is directly measured by a activity assay. The measurement of an AAV9 sample is given as a percentage relative to a reference material. The method allows a quantitative assessment of the biologic function of the AAV9 gene therapy vector.

SDS-PAGE analysis is performed to determine if there was a reduction in Heat Shock Protein 70 kDa (HSP70) when using the test procedure with the wash steps instead of the comparative procedure. A Western Blot is performed using an Anti-Hsp70 antibody (Abcam, catalog no. ab79852) as the primary antibody at 1:2000 dilution for two hours, and goat anti-rabbit igG (H+L) AP conjugate as the secondary antibody (Sigma, catalog no. A8025) in 1:1000 dilution for one hour.

An SDS-PAGE silver stain assay is performed to determine the overall level of impurities present.

A Western Blot with 12% anti-AAV antibody is performed to determine the levels and purity of the AAV9 recovered after purification according to the test and comparative procedures. The Western blot is performed with monoclonal antibodies to VP1, VP2 and VP3 of AAV9 as the primary antibodies, with goat anti-mouse ALP antibody (Sigma, catalog number A4656) as the secondary antibody.

LC-MS is performed (rp-HPLC-UV-ESI-MS/MS) to determine the identity and amounts of various host cell impurities. The samples are digested using the enzyme trypsin. The resulting peptide mixture is separated on a HPLC system using RP column (ZORBAX 300SB-C18 column, 0.5×150 mm, 3.5 µm), and subsequently, the peptides are analyzed on a Q-Exactive HF mass spectrometer. The data are analyzed using the software Proteome Discoverer to identify the proteins in the sample.

An Agilent HPLC1209 (1200 capHPLC) is used with ChemStation for LC 3D systems (Rev. B.04.03-SP2 (105)). The HPLC method is PEPMAP_CAP_170.M. Eluent A is 0.1% (v/v) HCOOH in deionized water and Eluent B is 0.08% (v/v) HCOOH in Acetonitrile. Details on HPLC are provided in the following Table 16:

TABLE 16

| HPLC-Skid: | HPLC1209: 1200 capHPLC, Agilent | | |
|---|---|---|---|
| Software: | ChemStation for LC 3D systems Rev. B.04.03-5P2 (105) | | |
| HPLC-Method: | PEPMAP_CAP_170.M | | |
| Column: | ZORBAX 3005B-C18 0.5 × 150 mm, 3.5 µm | | |
| | Part. No. 5064-8268 Ser. No. USHTC01001 Lot No. WSB1432005 | | |
| Eluent A: | 0.1% (v/v) HCOOH in deionized water, Lot 140617/01/DF3376/028 | | |
| Eluent B: | 0.08% (v/v) HCOOH in Acetonitrile, Lot 250117/02/ DF3270/015 | | |
| Pump: | Initial Conditions: | 15/min (micro flow) 100% A | |
| | Gradient: | 0 min 100% A | 0% B |
| | | 110 min 60% A | 40% B |
| | | 125 min 30% A | 70% B |
| | | 135 min 0% A | 100% B |
| | | 140 min 100% A | 0% B |
| | | Stop 170 min | |
| Autosampler: | Inject volume: | Various injection volumes | |
| | Temperature: | 4° C. | |
| | Contact Closure | Initial OPEN | |
| | | 0.02 min A—CLOSED | |
| | | 0.5 min A—OPEN | |
| Column Compartment: | Temperature: | 40° C. | |
| DAD-Detektor: | Wavelenghts | 214, 280, 260 nm, Spectrum 190-500 nm | |
| Needle Wash | Flushport | 5 sec (20% Isopropanol/80% H2O) | |

Details on the MS are provided in the following Table 17:

TABLE 17

| Skid: | Q Exactive HF #2 with heated electrospray ionization (HESI), |
|---|---|
| | Serial No. 05161L Thermo, |
| | Source: HESI-II |

TABLE 17-continued

| | | |
|---|---|---|
| Software: | Thermo Xcalibur 3.1.66.10 | |
| Tune Method: | high_parameters.mstune | |
| | Parameter | |
| | Sheath gas flow rate | 7 |
| | Aux gas flow rate | 0 |
| | Sweep gas flow rate | 0 |
| | Spray voltage | 3 kV |
| | Capillary Temperature | 275° C. |
| | S-lens RF | 50 |
| Instrument Method: | 170406_PEPMAP_TOP10_120k_CAP_140.meth | |
| | Parameter | |
| | FULL MS | |
| | Runtime | 140 min |
| | In-source CID | 0.0 eV |
| | Default charge state | 2 |
| | Microscans | 1 |
| | Resolution | 120,000 |
| | AGC target | 3e6 |
| | Maximum IT | 60 |
| | Number of scan ranges 1 | |
| | Scan range | 300-2000 m/z |
| | Spectrum data type | profile |
| | Polarity | positive |
| | dd-MS$^2$ | |
| | Microscans | 1 |
| | Resolution | 30,000 |
| | AGC target | 1e5 |
| | Maximum IT | 100 ms |
| | Loop count | 10 |
| | MSX count | 1 |
| | TopN | 10 |
| | Isolation window | 2.0 m/z |
| | Isolation offset | 0.0 m/z |
| | NCE/stepped | 27 |
| | Spectrum data type | centroid |
| | Underfill ratio | 0.6% |
| | Intensity threshold | 1.0e3 |
| | Apex trigger | OFF |
| | Charge exclusion | unassigned, 1, 7, 8, >8 |
| | Peptide match | preferred |
| | Exclude isotopes | on |
| | Dynamic exclusion | 30 s |
| MS Calibration/ Test Resolution: | Calibration solution Pierce LTQ Velos ESI Positive Ion Calibration Solution Order-No. 88323, Lot RF231587 Basis parameter | |
| | Tune File: | Calibration_pos_parameters 150818 |
| | Flow Syringe Pump: | 5 μl/ |
| | TIC Stability: | ≤10% |
| | IT (Injection Time): | ≤10 ms |
| | Ion Mode: | positive |
| | Calibration parameter | |
| | eFT Parameters (positive) | okay |
| | Analyzer Accuracy (positive) | okay |
| | Mass calibration (positive) | okay |
| | Test-Spectrum/Resolution | |
| | 1. Calibration solution | |
| | Resolution: | FTMS 120000 (at m/z 200) |
| | Mass Range: | m/z 135-1800 |
| | AGC Target: | 3e6 |
| | Number of scans: | 50 scans |
| | Filename: 170621_Calmix.raw | |
| | 2. m/z 524 MRFA (Komponente Kalibriermix) | |
| | Resolution: | FTMS 120000 (at m/z 200) |
| | Mass Range: | m/z 520-530 |
| | AGC Target: | 1e5: |
| | Number of scans 50 scans | |
| | Filename: 170621_MRFA.raw | |
| | Resolution (m/z 524) 83281 (80000 Benchmark) | |
| | Counts: 1.67 × 10$^7$ | |

Three different modes of purification are performed. One includes the comparative procedure of this example, another includes the test procedure of this example (that includes the anion exchange purification by MustangQ before affinity purification), and a third is conducted according to the test procedure but without the anion exchange purification by MustangQ.

Example 5

AAV9 production is developed in a HEK293 cell line after transfection with a triple plasmid system containing encoding cDNA of the protein of interest and AAV9-. VP1. -VP2 and -VP3. The clarified cell free culture supernatant is concentrated and diafiltrated with Pall Omega T-Series Cassette 100 kDa. The viral particles are loaded onto a membrane adsorber (MustangQ. Pall Part Number XT140MSTGQP05) at nonbinding conditions. The obtained AAV9 containing flow through is not pH adjusted to a pH range between 7.4 and 7.8 with 25% HCl. Instead, a LOAD is formed by reconstituting the AAV-8 containing flow through in a load buffer comprising 125 mM NaCl and 50 mM TrisHCl at a pH of 8.5.

Besides the advantage inherent in not having to include a pH adjustment step, having pH 8.5 can allow for improved robustness in affinity performance and prevention of unspecific binding of impurities to either the product or resin.

Samples from the various wash and elution steps are taken at various points to assay how much AAV9 is present in the sample. The assays indicate how much AAV9 is lost in various wash steps. The following test procedure is undertaken. First, a column containing POROS™ CaptureSelect™ AAV9 Affinity Resin (Cat. No. A27354; Thermo Fisher) ID 10 mm, with a bed height of 25 mm and a volume 1.96 ml, is equilibrated with at least five column volumes of 20 mM TrisHCl and 150 mM NaCl at pH 7.4. The LOAD is applied onto the column containing POROS™ CaptureSelect™ AAV9 Affinity Resin (Cat. No. A27354; Thermo Fisher). A portion of the sample loaded onto the column is saved and later assayed by ITR qPCR, ELISA against AAV antigens, and ELISA against HEK293 HCP antigens. The column is then re-equilibrated with 10 column volumes of 20 mM TrisHCl and 150 mM NaCl at pH 7.4. A sample of the flow through is saved and later assayed by ITR qPCR, ELISA against AAV antigens, and ELISA against HEK293 HCP antigens.

The column is then washed with 10 column volumes of Wash 1 (W1): 100 mM Sodium Acetate and 0.1% Tween80 at pH 6.0. The column is then washed with 10 column volumes of Wash 2 (W2): 50 mM TrisHCl and 125 mM NaCl at pH 8.5. The column is then washed with 10 column volumes of Wash 3 (W3): 50 mM TrisHCl and 50% ethylene glycol at pH 8.5. A sample from eluate of each of W1, W2 and W3 is taken and assayed according to ITR qPCR, ELISA against AAV antigens, and ELISA against HEK293 HCP antigens.

Elution is undertaken by applying 10 column volumes of the following elution buffer to the column: 50 mM TrisHCl, 50% ethylene glycol and 750 mM NaCl, at pH 8.0.

The above test procedure is described in more detail in Table 18.

TABLE 18

| Step | High pH LOAD | CV | Flowrate |
|---|---|---|---|
| 1. | 20 mM TrisHCl<br>150 mM NaCl<br>pH 7.4 | >5 | 30 cm/h |
| 2. | Sample-Load<br>pH 8.5 | | |
| 3. | 20 mM TrisHCl<br>150 mM NaCl<br>pH 7.4 | 10 | |
| 4. | 100 mM NaAcetat<br>0.1% Tween80<br>pH 6.0 | 10 | |
| 5. | 50 mM TrisHCl<br>125 mM NaCl<br>pH 8.5 | 10 | |
| 6. | 50 mM TrisHCl<br>50% Ethylene glycol<br>pH 8.5 | 10 | 30 cm/h |
| 7. | ELUTION<br>50 mM TrisHCl<br>50% Ethylene glycol<br>750 mM NaCl<br>pH 8.0 | 10 | |
| 8. | 50 mM TrisHCl<br>50% Ethylene glycol<br>2000 mM NaCl<br>pH 8.0 | 10 | |

The samples taken are assayed by each of ITR qPCR, ELISA against AAV antigens and ELISA against HEK293 HCP to assess yield and whether losses may have occurred in the steps.

Samples above are also assayed by SDS-PAGE and 12% silver stain to detect total protein.

Samples are then assayed by SDS-PAGE and a Western blot against AAV9 antigens. The primary antibodies are monoclonal antibodies against VP1, VP2 and VP3 of AAV9 while the secondary antibody is a goat anti-mouse coupled with phosphatase.

Example 6

AAV9 production is developed in a HEK293 cell line after transfection with a triple plasmid system containing encoding cDNA of the protein of interest and AAV9-. VP1. -VP2 and -VP3. The clarified cell free culture supernatant is concentrated and diafiltrated with Pall Omega T-Series Cassette 100 kDa. The viral particles are loaded onto a membrane adsorber (MustangQ, Pall Part Number XT140MSTGQP05) at nonbinding conditions, i.e. in a solution comprising 125 mM NaCl and 50 mM TrisHCl at pH 8.5. A pH conditioned LOAD is obtained by adjusting the AAV9 containing flow through to a pH range between 7.4 and 7.8 with 25% HCl.

The following test procedure is undertaken. First, a column containing anti-intact AAV8/9 antibody (Cat. No. 03-651161, American Research Products, Inc., Waltham, MA) immobilized on resin ("ADK8/9 affinity resin") ID 32 mm, with a bed height of 59 mm and a volume 47.45 ml, is equilibrated with at least five column volumes of 20 mM TrisHCl and 150 mM NaCl at pH 7.4. The pH conditioned LOAD is applied onto the column containing ADK8/9 affinity resin. The column is then re-equilibrated with five column volumes of 20 mM TrisHCl and 150 mM NaCl at pH 7.4 (optional fourth buffer).

The column is then washed with five column volumes of Wash 1 (W1): 100 mM Sodium Acetate and 0.1% Tween80 at pH 6.0. The column is then washed with five column volumes of Wash 2 (W2): 50 mM TrisHCl and 125 mM NaCl at pH 8.5. The column is then washed with five column volumes of Wash 3 (W3): 50 mM TrisHCl and 50% ethylene glycol at pH 8.5.

Elution is undertaken by applying five column volumes of the following elution buffer to the column: 50 mM TrisHCl, 50% ethylene glycol and 750 mM NaCl, at pH 8.0. Five column volumes of the following secondary elution buffer is then applied to the column: 50 mM TrisHCl, 50% ethylene glycol, and 2000 mM NaCl.

The linear flow rate for the above steps is 60 cm/h.

The following comparative procedure is undertaken. A column containing ADK8/9 affinity resin, ID 10 mm, with a bed height of 2.5 mm and a volume 1.96 ml, is equilibrated with at least 10 column volumes of 20 mM TrisHCl and 150 mM NaCl at pH 7.4. The pH conditioned LOAD is applied onto the column containing ADK8/9 affinity resin. The column is then re-equilibrated with 10 column volumes of 20 mM TrisHCl and 150 mM NaCl at pH 7.4.

A wash step is performed by using the following TBS buffer: 20 mM TrisHCl/150 mM NaCl/pH 7.4. Instead elution is conducted with 10 column volumes of 100 mM sodium citrate at pH 3.0.

The above test and comparative procedure are described in more detail in Table 1, with "CV" indicating the number of column volumes of solution added in the step.

Density of the elution buffer is measured on an oscillating U-tube density meter DMA 4500M (Anton Paar).

ELISA is used to measure the quantity of AAV9 antigen. ELISA is carried out with an AAV-9 titration ELISA Kit (Art. No. PRAAV9; Progen (Heidelberg, Germany) on a TECAN Roboter system. Briefly, a monoclonal antibody specific for AAV9 capsids (AAV8/9 antibody ("ADK8/9 antibody", Cat. No. 03-651161, American Research Products, Inc., Waltham, MA)) is coated onto microtiter strips and is used to capture AAV9 particles from the AAV fraction. The capture AAV9 particles are detected by two steps. In a first step, a biotin-conjugated monoclonal antibody specific for the ADK8/9 antibody is bound to the immune complex (of ADK8/9 and ADK8/9 antibody). Streptavidin peroxidase conjugates are added to the immune complexes bound to the biotin-conjugated monoclonal antibody and the streptavidin peroxidase conjugates react with the biotin. A peroxidase substrate solution is added and a color reaction which is proportional to the amount of bound AAV particles occurs. The color reaction is measured photometrically at 450 nm.

An ITR-qPCR assay is used to determine the genome copy titer by quantifying the inverted tandem repeats found in the vector encoding for the gene of interest (e.g., human Factor VIII or human Factor IX). HEK-HCP is a measurement of the residual host cell protein by ELISA. LDH is determined by a colorimetric activity assay.

AAV8/9 Ligand Leakage ELISA (Enzyme Linked Immuno-Sorbent Assay) can detect an affinity ligand that may be present in product purified with ADK8/9 affinity resin.

In the in-vitro biopotency assay, the viral vector AAV9 infects a hepatic target cell line, which subsequently secretes functional, measurable encoded protein into the medium. In a first step HepG2 target cells are transduced infected by AAV9. During incubation time encoded protein is released into cell supernatant. In a second step the activity of the encoded protein into the cell culture supernatant is directly measured by an activity assay. The measurement of an AAV9 sample is given as a percentage relative to a reference material. The method allows a quantitative assessment of the biologic function of the AAV9 gene therapy vector.

SDS-PAGE analysis is performed to determine if there was a reduction in Heat Shock Protein 70 kDa (HSP70) when using the test procedure with the wash steps instead of the comparative procedure. A Western Blot is performed using an Anti-Hsp70 antibody (Abcam, catalog no. ab79852) as the primary antibody at 1:2000 dilution for two hours, and goat anti-rabbit igG (H+L) AP conjugate as the secondary antibody (Sigma, catalog no. A8025) in 1:1000 dilution for one hour.

An SDS-PAGE silver stain assay is performed to determine the overall level of impurities present.

A Western Blot with 12% anti-AAV antibody is performed to determine the levels and purity of the AAV9 recovered after purification according to the test and comparative procedures. The Western blot is performed with monoclonal antibodies to VP1, VP2 and VP3 of AAV9 as the primary antibodies, with goat anti-mouse ALP antibody (Sigma, catalog number A4656) as the secondary antibody.

L-MS is performed (rp-HPLC-UV-ESI-MS/MS) to determine the identity and amounts of various host cell impurities. The samples are digested using the enzyme trypsin. The resulting peptide mixture is separated on a HPLC system using RP column (ZORBAX 300SB-C18 column, 0.5×150 mm, 3.5 µm), and subsequently, the peptides are analyzed on a Q-Exactive HF mass spectrometer. The data are analyzed using the software Proteome Discoverer to identify the proteins in the sample.

An Agilent HPLC1209 (1200 capHPLC) is used with ChemStation for LC 3D systems (Rev. B.04.03-SP2 (105)). The HPLC method is PEPMAP_AP_170.M. Eluent A is 0.1% (v/v) HCOOH in deionized water and Eluent B is 0.08% (v/v) HCOOH in Acetonitrile. Details on HPLC are provided in the following Table 19:

TABLE 19

| HPLC-Skid: | HPLC1209: 1200 capHPLC, Agilent | | |
|---|---|---|---|
| Software: | ChemStation for LC 3D systems Rev. B.04.03-SP2 (105) | | |
| HPLC-Method: | PEPMAP_CAP_170.M | | |
| Column: | ZORBAX 300SB-C18 0.5 × 150 mm, 3.5 µm Part. No. 5064-8268 Ser. No. USHTC01001 Lot No. WSB1432005 | | |
| Eluent A: | 0.1% (v/v) HCOOH in deionized water, Lot 140617/01/DF3376/028 | | |
| Eluent B: | 0.08% (v/v) HCOOH in Acetonitrile, Lot 250117/02/DF3270/015 | | |
| Pump: | Initial Conditions: | 15 µl/min (micro flow) 100% A | |
| | Gradient: | 0 min | 100% A 0% B |
| | | 110 min | 60% A 40% B |
| | | 125 min | 30% A 70% B |
| | | 135 min | 0% A 100% B |
| | | 140 min | 100% A 0% B |
| | | Stop 170 min | |
| Autosampler: | Inject volume: | Various injection volumes | |
| | Temperature: | 4° C. | |
| | Contact Closure | Initial OPEN 0.02 min A—CLOSED 0.5 min A—OPEN | |
| Column Compartment: | Temperature: | 40° C. | |
| DAD-Detektor: | Wavelenghts | 214, 280, 260 nm, Spectrum 190-500 nm | |
| Needle Wash | Flushport | 5 sec (20% Isopropanol/ 80% H2O) | |

Details on the MS are provided in the following Table 20:

TABLE 20

| Skid: | Q Exactive HF #2 with heated electrospray ionization (HESI), Serial No. 05161L Thermo, Source: HESI-II |
|---|---|
| Software: | Thermo Xcalibur 3.1.66.10 |
| Tune Method: | high_parameters.mstune |
| Parameter | |
| Sheath gas flow rate | 7 |
| Aux gas flow rate | 0 |
| Sweep gas flow rate | 0 |
| Spray voltage | 3 kV |
| Capillary Temperature | 275° C. |
| S-lens RF | 50 |
| Instrument Method: | 170406_PEPMAP_TOP10_120k_CAP_140.meth |
| Parameter | |
| FULL MS | |
| Runtime | 140 min |
| In-source CID | 0.0eV |
| Default charge state | 2 |
| Microscans | 1 |
| Resolution | 120,000 |
| AGC target | 3e6 |
| Maximum IT | 60 |
| Number of scan ranges | 1 |
| Scan range | 300-2000 m/z |
| Spectrum data type | profile |
| Polarity | positive |
| dd-MS$^2$ | |
| Microscans | 1 |
| Resolution | 30,000 |
| AGC target | 1e5 |
| Maximum IT | 100 ms |
| Loop count | 10 |
| MSX count | 1 |
| TopN | 10 |
| Isolation window | 2.0 m/z |
| Isolation offset | 0.0 m/z |
| NCE/stepped | 27 |
| Spectrum data type | centroid |
| Underfill ratio | 0.6% |
| Intensity threshold | 1.0e3 |
| Apex trigger | OFF |
| Charge exclusion | unassigned, 1, 7, 8, >8 |
| Peptide match | preferred |
| Exclude isotopes | on |
| Dynamic exclusion | 30 s |
| MS Calibration/ Test Resolution: | Calibration solution Pierce LTQ Velos ESI Positive Ion Calibration Solution Order-No. 88323, Lot RF231587 Basis parameter |
| Tune File: | Calibration_pos_ parameters_150818 |
| Flow Syringe Pump: | 5 µl/ |
| TIC Stability: | ≤10% |
| IT (Injection Time): | ≤10 ms |
| Ion Mode: | positive |
| Calibration parameter | |
| eFT Parameters (positive) | okay |
| Analyzer Accuracy (positive | okay |
| Mass calibration (positive) | okay |
| Test-Spectrum/Resolution | |
| 1. Calibration solution | |
| Resolution: | FTMS 120000 (at m/z 200) |
| Mass Range: | m/z 135-1800 |
| AGC Target: | 3e6 |
| Number of scans: | 50 scans |
| Filename: 170621_Calmix.raw | |
| 2. m/z 524 MRFA | |

TABLE 20-continued (Komponente Kalibriermix)

| Resolution: | FTMS 120000 (at m/z 200) |
|---|---|
| Mass Range: | m/z 520-530 |
| AGC Target: | 1e5: |
| Number of scans 50 scans | |
| Filename: 170621_MRFA.raw | |
| Resolution (m/z 524) 83281 (80000 Benchmark) | |
| Counts: 1.67 × 10^7 | |

Three different modes of purification are performed. One includes the comparative procedure of this example, another includes the test procedure of this example (that includes the anion exchange purification by MustangQ before affinity purification), and a third is conducted according to the test procedure but without the anion exchange purification by MustangQ.

Example 7

AAV9 production is developed in a HEK293 cell line after transfection with a triple plasmid system containing encoding cDNA of the protein of interest and AAV9-. VP1. -VP2 and -VP3. The clarified cell free culture supernatant is concentrated and diafiltrated with Pall Omega T-Series Cassette 100 kDa. The viral particles are loaded onto a membrane adsorber (MustangQ. Pall Part Number XT140MSTGQP05) at nonbinding conditions. The obtained AAV9 containing flow through is not pH adjusted to a pH range between 7.4 and 7.8 with 25% HCl. Instead, a LOAD is formed by reconstituting the AAV9-containing flow through in a load buffer comprising 125 mM NaCl and 50 mM TrisHCl at a pH of 8.5.

Besides the advantage inherent in not having to include a pH adjustment step, having pH 8.5 can allow for improved robustness in affinity performance and prevention of unspecific binding of impurities to either the product or resin.

Samples from the various wash and elution steps are taken at various points to assay how much AAV9 is present in the sample. The assays indicate how much AAV9 is lost in various wash steps. The following test procedure is undertaken. First, a column containing ADK8/9 affinity resin ID 10 mm, with a bed height of 25 mm and a volume 1.96 ml, is equilibrated with at least five column volumes of 20 mM TrisHCl and 150 mM NaCl at pH 7.4. The LOAD is applied onto the column containing ADK8/9 affinity resin. A portion of the sample loaded onto the column is saved and later assayed by ITR qPCR, ELISA against AAV antigens, and ELISA against HEK293 HCP antigens. The column is then re-equilibrated with 10 column volumes of 20 mM TrisHCl and 150 mM NaCl at pH 7.4. A sample of the flow through is saved and later assayed by ITR qPCR, ELISA against AAV antigens, and ELISA against HEK293 HCP antigens.

The column is then washed with 10 column volumes of Wash 1 (W1): 100 mM Sodium Acetate and 0.1% Tween80 at pH 6.0. The column is then washed with 10 column volumes of Wash 2 (W2): 50 mM TrisHCl and 125 mM NaCl at pH 8.5. The column is then washed with 10 column volumes of Wash 3 (W3): 50 mM TrisHCl and 50% ethylene glycol at pH 8.5. A sample from eluate of each of W1, W2 and W3 is taken and assayed according to ITR qPCR, ELISA against AAV antigens, and ELISA against HEK293 HCP antigens.

Elution is undertaken by applying 10 column volumes of the following elution buffer to the column: 50 mM TrisHCl, 50% ethylene glycol and 750 mM NaCl, at pH 8.0.

The above test procedure is described in more detail in Table 21.

TABLE 21

| Step | High pH LOAD | CV | Flow rate |
|---|---|---|---|
| 1. | 20 mM TrisHCl 150 mM NaCl pH 7.4 | >5 | 30 cm/h |
| 2. | Sample-Load pH 8.5 | | |
| 3. | 20 mM TrisHCl 150 mM NaCl pH 7.4 | 10 | |
| 4. | 100 mM NaAcetat 0.1% Tween80 pH 6.0 | 10 | |
| 5. | 50 mM TrisHCl 125 mM NaCl pH 8.5 | 10 | |
| 6. | 50 mM TrisHCl 50% Ethylene glycol pH 8.5 | 10 | 30 cm/h |
| 7. | ELUTION 50 mM TrisHCl 50% Ethylene glycol 750 mM NaCl pH 8.0 | 10 | |
| 8. | 50 mM TrisHCl 50% Ethylene glycol 2000 mM NaCl pH 8.0 | 10 | |

The samples taken are assayed by each of ITR qPCR, ELISA against AAV antigens and ELISA against HEK293 HCP to assess yield and whether losses may have occurred in the steps.

Samples above are also assayed by SDS-PAGE and 12% silver stain to detect total protein.

Samples are then assayed by SDS-PAGE and a Western blot against AAV9 antigens. The primary antibodies are monoclonal antibodies against VP1, VP2 and VP3 of AAV9 while the secondary antibody is a goat anti-mouse coupled with phosphatase.

Example 8

AAV8 ELISA was carried out with an AAV-8 titration ELISA Kit (Art. No. PRAAV8; Progen (Heidelberg, Germany) on a TECAN Roboter system. A monoclonal antibody specific for a conformational epitope on assembled AAV8 capsids (ADK8) was coated onto microtiter strips and was used to capture AAV8 particles from the AAV fraction. The capture AAV8 particles were detected by two steps. In a first step, a biotin-conjugated monoclonal antibody specific for the ADK8 antibody was bound to the immune complex. Streptavidin peroxidase conjugates were added to the immune complexes bound to the biotin-conjugated monoclonal antibody and the streptavidin peroxidase conjugates reacted with the biotin. A peroxidase substrate solution was added and a color reaction which is proportional to the amount of bound AAV particles occurs. The color reaction was measured photometrically at 450 nm.

Example 9

For the ITR-qPCR assays carried out in the Examples, the following procedure was undertaken. The vector genome titer (vg) per milliliter (ml) was determined using a TaqMan based qPCR with primers and a fluorescently labeled probe detecting a sequence within the ITR sequences of the vector genome. For detecting the ITR-specific sequence in the AAV particle the samples underwent different treatments. Samples were treated with DNAse I and subsequently with Proteinase K such that the scAAV genome was released from the capsid. Then, a restriction enzyme digest with was performed to resolve AAV ITR T-shape structures.

The plasmid used as reference material was linearized with a single cutter restriction enzyme und further purified from an agarose Gel. The UV A260 absorbance of gel-extracted DNA was measured thrice in a UV spectrophotometer, with the mean value of DNA concentration calculated in μg per ml.

To determine the copy numbers per ml for the linearized standard plasmid, the molecular weight of ds DNA was calculated in grams per mol considering the exact mass for each individual nucleotide of the underlying sequence.

The vector genome titer in the test article (in vector genomes per mL) was calculated via plasmid standard curve fitting with linear regression.

Example 10

AAV8 production was developed in a HEK293 cell line after transfection with a triple plasmid system containing encoding cDNA of the protein of interest and AAV8-. VP1. -VP2 and -VP3. The clarified cell free culture supernatant was concentrated and diafiltrated with Pall Omega T-Series Cassette 300 kDa. The viral particles were loaded onto a membrane adsorber (MustangQ. Pall Part Number XT140MSTGQP05) at nonbinding conditions for AAV8. The obtained AAV8 containing flow through was diluted with a dilution buffer comprising 100 mM arginine, 200 mM NaCl at pH 8.0 to prepare a load for the AAV8-Affinity matrix. The arginine-containing load was applied onto a column containing POROS™ CaptureSelect™ AAV8 affinity matrix (Thermo Fisher, Catalog No. A30793).

Samples from the various wash and elution steps were taken at various points to assay how much AAV8 is present in the sample. The assays indicate how much AAV8 was lost in various wash steps. The following test procedure was undertaken. First, a column containing ADK8/9 affinity resin ID 10 mm, with a bed height of 25 mm and a volume 2.04 ml, was equilibrated with at least ten column volumes of 20 mM TrisHCl and 125 mM NaCl at pH 8.5. The load was applied onto the column containing ADK8/9 affinity resin. A portion of the sample loaded onto the column was saved and later assayed by ITR qPCR, ELISA against AAV antigens, and ELISA against HEK293 HCP antigens. The column was then re-equilibrated (Wash 1, W1) with 10 column volumes of 50 mM TrisHCl and 125 mM NaCl at pH 8.5. A sample of the flow through was saved and later assayed by ITR qPCR, ELISA against AAV antigens, and ELISA against HEK293 HCP antigens.

The column was then washed with 10 column volumes of Wash 2 (W2): 100 mM Sodium Acetate and 0.1% Tween80 at pH 6.0. The column was then washed with 10 column volumes of Wash 3 (W3): 50 mM TrisHCl and 125 mM NaCl at pH 8.5. The column was then washed with 10 column volumes of Wash 4 (W4): 50 mM TrisHCl and 50% ethylene glycol at pH 8.5. A sample from eluate of each of W2, W3 and W4 was taken and assayed according to ITR qPCR, ELISA against AAV antigens, and ELISA against HEK293 HCP antigens.

Elution was undertaken by first applying 10 column volumes of the following elution buffer to the column: 50 mM TrisHCl, 60% (w/w) ethylene glycol and 750 mM NaCl, at pH 8.0. No wash step was subsequently performed.

Elution was continued by next applying 10 column volumes of the following elution buffer to the column: 50 mM TrisHCl, 60% (w/w) ethylene glycol and 1000 mM NaCl, at pH 8.0. The column was then washed with 20 mM Tris HCl at pH 7.4. The column was then regenerated by applying to the column 10 column volumes of a solution comprising 100 mM glycine and 200 mM NaCl, at pH 2.5.

The above test procedure is described in more detail in Table 22.

TABLE 22

| STEP | |
|---|---|
| Equilibration | 50 mM Tris HCl |
| | 125 mM NaCl |
| | pH 8.5 |
| LOAD | MUQ-FT |
| Wash 1 | 50 mM Tris HCl |
| (Re-equilibration) | 125 mM NaCl |
| | pH 8.5 |
| Wash 2 | 100 mM Na-Acetate |
| | 0.1% Tween 80 |
| | pH 6.0 |
| Wash 3 | 50 mM Tris HCl |
| | 125 mM NaCl |
| | pH 8.5 |
| Wash 4 | 50 mM Tris HCl |
| | 50% (w/w) Ethylene glycol |
| | pH 8.5 |
| ELUTION 1 | 50 mM Tris HCl |
| | 60% (w/w) Ethylene glycol |
| | 750 mM NaCl |
| | pH 8.0 |
| ELUTION 2 | 50 mM Tris HCl |
| | 60% (w/w) Ethylene glycol |
| | 1000 mM NaCl |
| | pH 8.0 |
| Wash 6 | 20 mM Tris HCl |
| | pH 7.4 |
| Regeneration | 100 mM Glycine |
| | 200 mM NaCl |
| | pH 2.5 |

Example 11

AAV8 production was developed in a HEK293 cell line after transfection with a triple plasmid system containing encoding cDNA of the protein of interest and AAV8-. VP1. -VP2 and -VP3. From a 30 L Harvest aliquot the cells were disrupted by using a Megatron MT3000(Pall), followed by filtration of the AAV8 containing solution on a) depth filter PDP8 Area 0.5 m² b) depth filter V100 Area: 0.5 m² and c) Kleenpak Capsule 0.2 μm Area 0.15 m². The clarified cell free culture supernatant was concentrated and diafiltrated with Pall Omega T-Series Cassette 300 kDa. The viral particles were loaded onto a membrane adsorber (MustangQ. Pall Part Number XT140MSTGQP05) at nonbinding conditions for AAV8. The obtained AAV8 containing flow through was diluted 1:2 with a dilution buffer comprising 100 mM arginine, 200 mM NaCl at pH 8.0 to prepare a load for the AAV8-Affinity matrix. The arginine-containing load was applied onto a column containing POROS™ CaptureSelect™ AAV8 affinity matrix (Thermo Fisher, Catalog No. A30793; ID 10 mm, Bed height 26 mm, volume 2.04 ml).

Samples from the various wash and elution steps were taken at various points to assay how much AAV8 is present in the sample. The assays indicate how much AAV8 was lost in various wash steps. The following test procedure was undertaken. First, a column containing ADK8/9 affinity resin ID 10 mm, with a bed height of 25 mm and a volume 2.04 ml, was equilibrated with at least ten column volumes of 50 mM Arginine-HCl and 100 mM NaCl at pH 8.0. The load was applied onto the column containing ADK8/9 affinity resin. A portion of the sample loaded onto the column was saved and later assayed by ITR qPCR, ELISA against AAV antigens, and ELISA against HEK293 HCP antigens. The column was then re-equilibrated (Wash 1, W1) with 10 column volumes of 50 mM Arginine-HCl and 100 mM NaCl at pH 8.0. A sample of the flow through was saved and later assayed by ITR qPCR, ELISA against AAV antigens, and ELISA against HEK293 HCP antigens.

The column was then washed with 10 column volumes of Wash 2 (W2): 100 mM MES-Natrium, 10 mM EDTA, and 11.2 g/kg S/D II Solution (18.0 g Tween 80, 3.4 g DMSO, and 3.6 g TnBP) at pH 6.0. The column was then washed with 10 column volumes of Wash 3 (W3): 50 mM Arginine-HCl and 100 mM NaCl at pH 8.0. The column was then washed with 10 column volumes of Wash 4 (W4): 50 mM Arginine-HCl and 50% sucrose at pH 8.5. A sample from eluate of each of W2, W3 and W4 was taken and assayed according to ITR qPCR, ELISA against AAV antigens, and ELISA against HEK293 HCP antigens.

Elution was undertaken by first applying 10 column volumes of the following elution buffer to the column: 50 mM Arginine-HCl, 55% (w/w) sucrose, 2 mM $MgCl_2$, and 800 mM NaCl, at pH 8.0. The column was then washed with 10 column volumes of a Wash 5 (W5): 50 mM Arginine-HCl and 100 mM NaCl at pH 8.0. Elution was continued by next applying 10 column volumes of the following elution buffer to the column: 50 mM Arginine-HCl, 50% (v/v) glycerol, and 800 mM NaCl, at pH 8.0. The column was then washed with 50 mM Arginine-HCl and 100 mM NaCl at pH 8.0. The column was then regenerated by applying to the column 10 column volumes of a solution comprising 100 mM glycine and 200 mM NaCl, at pH 2.7.

The above test procedure is described in more detail in Table 23. A linear flow rate of 39 cm/h was applied in all steps.

TABLE 23

| STEP | |
|---|---|
| Equilibration | 50 mM Arginine-HCl<br>100 mM NaCl<br>pH 8.0 |
| LOAD | MUQ-FT dil 1:2 |
| Wash 1<br>(Re-equilibration) | 50 mM Arginine-HCl<br>100 mM NaCl<br>pH 8.0 |
| Wash 2 | 100 mM MES-Natrium<br>10 mM EDTA<br>pH 6.0<br>11.2 g/kg S/D II solution<br>(18.0 g Tween 80, 3.4 g DMSO, 3.6 g TnBP) |
| Wash 3 | 50 mM Arginine-HCl<br>100 mM NaCl<br>pH 8.0 |
| Wash 4 | 50 mM Arginine-HCl<br>50% (w/w) Sucrose<br>pH 8.5 |
| ELUTION 1 | 50 mM Arginine-HCl<br>55 (w/w) % Sucrose<br>2 mM MgCl2 +<br>800 mM NaCl<br>pH 8.0 |
| Wash 5 | 50 mM Arginine-HCl<br>100 mM NaCl<br>pH 8.0 |

TABLE 23-continued

| ELUTION 2 | 50 mM Arginine-HCl<br>50% (v/v) Glycerol +<br>800 mM NaCl<br>pH 8.0 |
|---|---|
| Wash 6 | 50 mM Arginine-HCl<br>100 mM NaCl<br>pH 8.0 |
| Regeneration | 100 mM Glycine<br>200 mM NaCl<br>pH 2.7 |

In the Load step above, the 1:2 dilution in the Mustang Q column was made to adjust the load to conditions close to the matrix of the equilibration buffer. This step was done to investigate the influence of the buffer substances in terms of binding of AAV8 to the ligand. Any new introduced compound can have potential competitive properties and/or it potentially can trigger elution.

Figure 7:
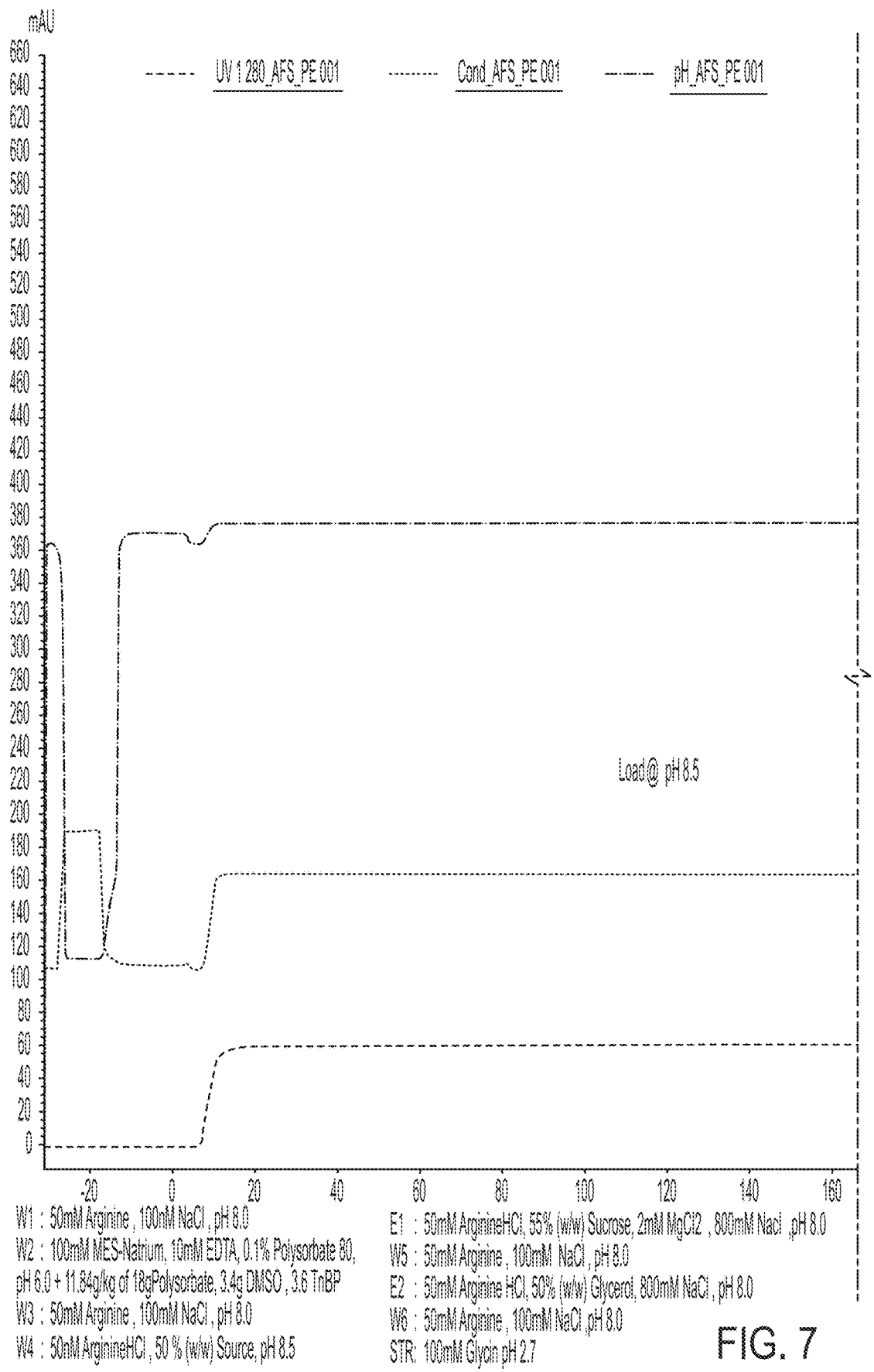
FIG. 7 depicts the chromatogram of the separation procedure according to Example 11.
Figure 7:
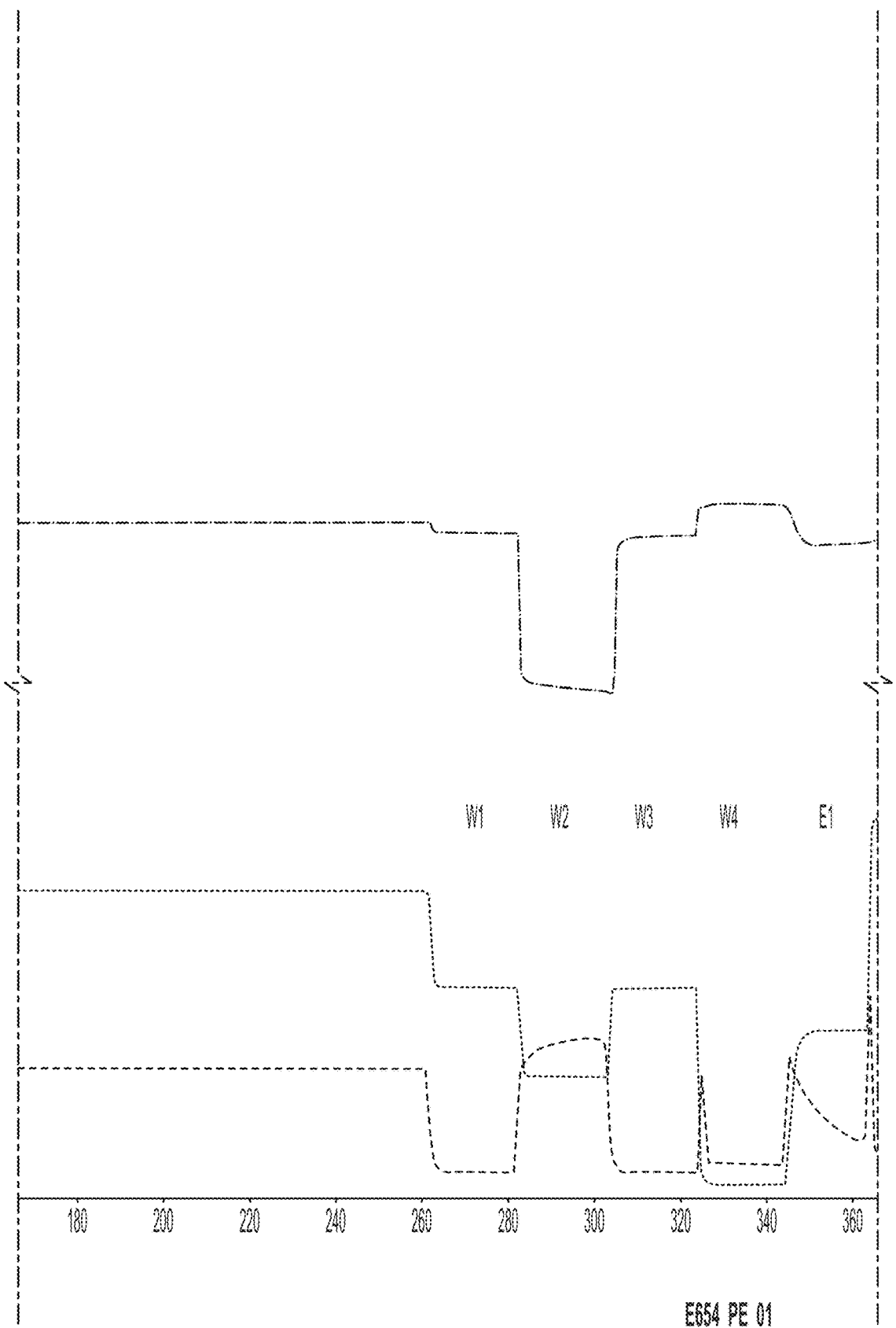
Figure 7:
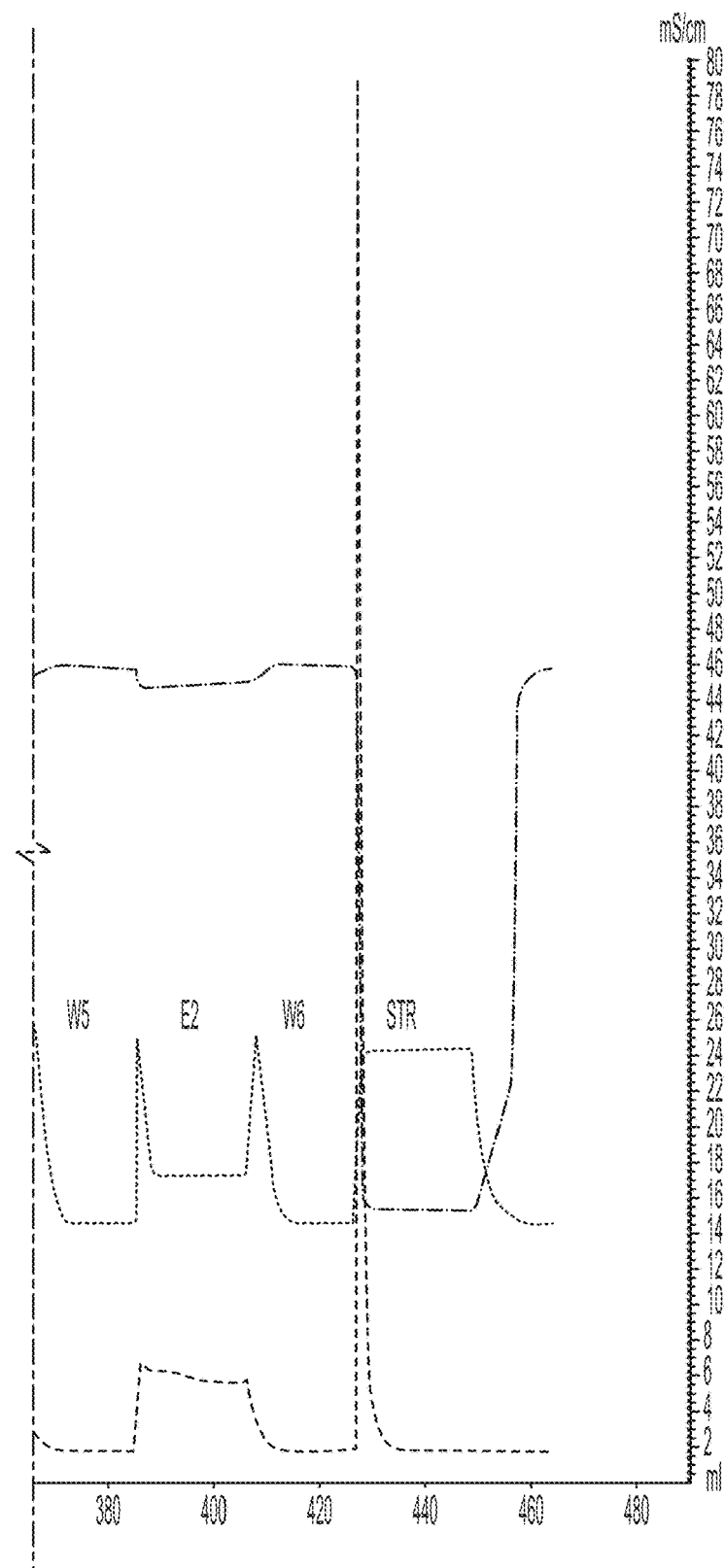

The samples taken were assayed by each of ITR qPCR, ELISA against AAV antigens and ELISA against HEK293 HCP to assess yield and whether losses may have occurred in the steps. The chromatogram associated with the above example is shown in FIG. 7. The following Table 24 shows the samples taken at each of the above steps, with the yield of each component shown in Table 25.

TABLE 24

| Step | Buffer | Flowrate | CV | Fraction |
|---|---|---|---|---|
| Resin activation | 100 mM Glycine pH 2.7 | 39 cm/h | 10 | Waste |
| Equilibration | 50 mM Arginine, 100 mM NaCl, pH 8.0 | | 10 | Waste |
| Sample application | MUQ_FT diluted 1:2 | | X | FT/Wash 1 |
| WASH 1 Re-equilibration | 50 mM Arginine, 100 mM NaCl, pH 8.0 | | 10 | FT/Wash 1 |
| WASH 2 | 100 mM MES-Natrium, 10 mM EDTA, pH 6.0+ 9.09 g/kg Polysorbate 80, 1.53 g/kg DMSO, 1.62 g/kg TnBP | | 10 | Wash 2 |
| WASH 3 | 50 mM Arginine, 100 mM NaCl, pH 8.0 | | 10 | Wash 3 |
| WASH4 | 50 mM Arginine-HCl, 50% (w/w) Sucrose, pH 8.5 | | 10 | Wash 4 |
| Elution1 | 50 mM Arginine-HCl, 55 (w/w) % Sucrose, 2 mM MgCl2, 800 mM NaCl, pH 8.0 | | 10 | Elution1 |
| WASH5 | 50 mM Arginine, 100 mM NaCl, pH 8.0 | | 10 | Wash 5 |
| Elution2 | 50 mM Arginine-HCl, 50% (w/w)Glycerol 800 mM NaCl, pH 8.0 | | 10 | Elution1 |
| WASH6 | 50 mM Arginine, 100 mM NaCl, pH 8.0 | | 10 | Wash 6 |
| STRIP | 100 mM Glycine pH 2.7 | | 10 | Str/Ntr |

The "Wash 5" step reduced fronting effects in elution.

TABLE 25

| Step | Amount | AAV8 Antigen | Total AAV8 Antigen | % AAV8 Antigen | ITR-qPCR | Total ITR-qPCR | % ITR-qPCR |
|---|---|---|---|---|---|---|---|
| LOAD | 273.18 | 14.1 | 3851.838 | 100.00% | 18.2 | 4970 | 100.0% |
| FT/WASH 1 | 279.53 | 0.1 | 27.953 | 0.73% | n.d | n.d | n.d |
| WASH 2 | 20.56 | 0.062 | 1.275 | 0.03% | n.d | n.d | n.d |
| WASH 3 | 20.55 | 0.065 | 1.336 | 0.03% | n.d | n.d | n.d |
| WASH4 | 24.33 | 6.35 | 154.496 | 4.01% | n.d | n.d | n.d |
| Elution1 | 25.76 | 50.92 | 1311.699 | 34.05% | 29.8 | 768 | 15.44% |
| WASH5 | 21.44 | 10.53 | 225.763 | 5.86% | n.d | n.d | n.d |
| Elution2 | 23.07 | 19.79 | 456.555 | 11.85% | 14.9 | 344E | 6.91% |
| WASH6 | 21.31 | 3.84 | 81.830 | 2.12% | n.d | n.d | n.d |
| STRIP | 22.68 | 57.2 | 1297.296 | 33.68% | 70.6 | 1600 | 32.21% |

Figure 8:
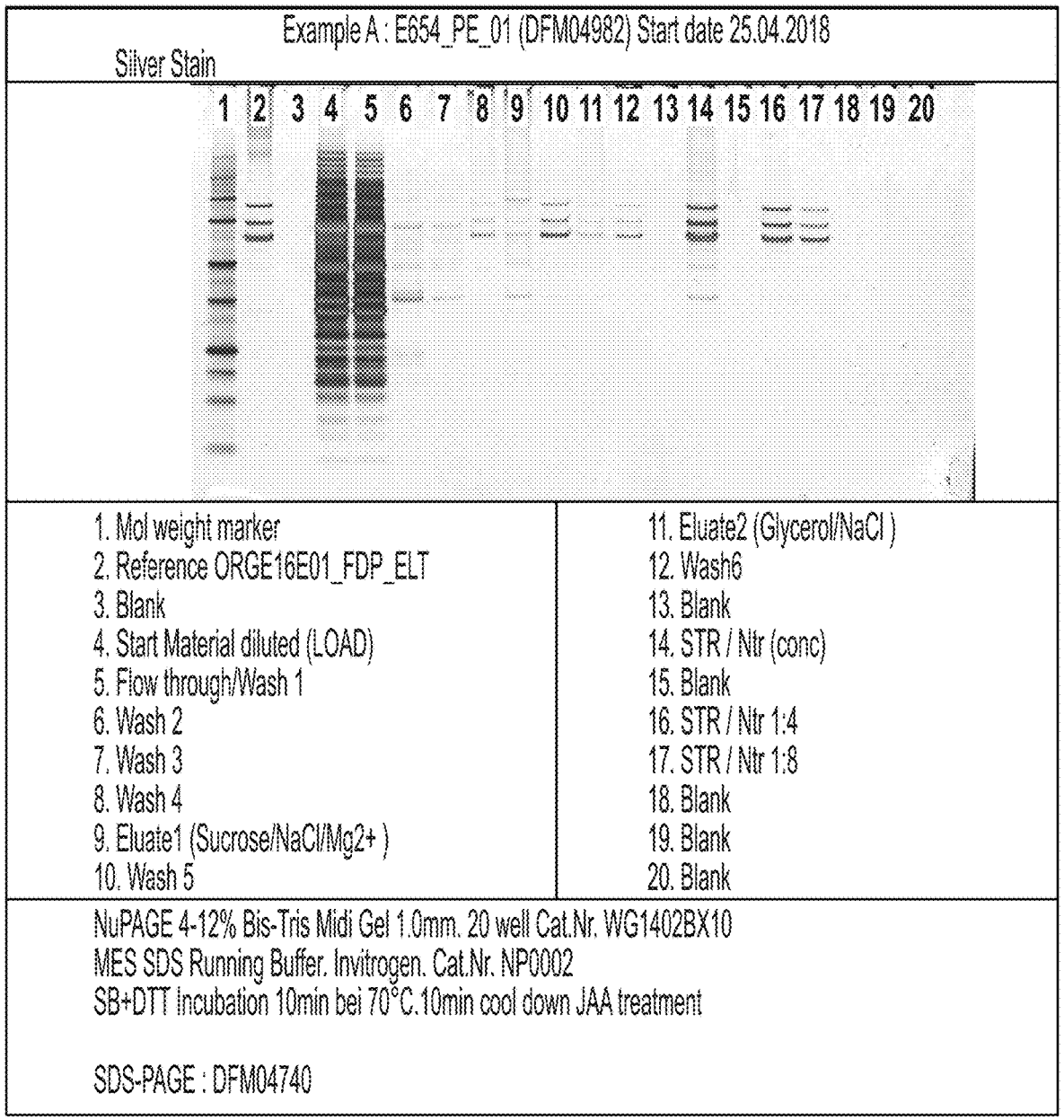
FIG. 8 depicts an SDS-PAGE silver stain gel showing the proteins present in various fractions from various wash steps and eluates according to Example 11.

Samples above were also assayed by SDS-PAGE and 12% silver stain to detect total protein. The SDS-PAGE assay results shown in FIG. 8.

Example 12

AAV8 production was developed in a HEK293 cell line after transfection with a triple plasmid system containing encoding cDNA of the protein of interest and AAV8-.VP1. -VP2 and -VP3. From a 30 L Harvest aliquot the cells were disrupted by using a Megatron MT3000(Pall), followed by filtration of the AAV8 containing solution on a) depth filter PDP8 Area 0.5 m$^2$ b) depth filter V100 Area: 0.5 m$^2$ and c) Kleenpak Capsule 0.2 µm Area 0.15 m$^2$. The clarified cell free culture supernatant was concentrated and diafiltrated with Pall Omega T-Series Cassette 300 kDa. The viral particles were loaded onto a membrane adsorber (MustangQ. Pall Part Number XT140MSTGQP05) at nonbinding conditions for AAV8. The load was applied onto a column containing POROS™ CaptureSelect™ AAV8 affinity matrix (Thermo Fisher, Catalog No. A30793; ID 10 mm, Bed height 26 mm, volume 2.04 ml).

Samples from the various wash and elution steps were taken at various points to assay how much AAV8 is present in the sample. The assays indicate how much AAV8 was lost in various wash steps. The following test procedure was undertaken. First, a column containing ADK8/9 affinity resin ID 10 mm, with a bed height of 25 mm and a volume 2.04 ml, was equilibrated with at least ten column volumes of 50 mM TrisHCl and 125 mM NaCl at pH 8.5. The load was applied onto the column containing ADK8/9 affinity resin. A portion of the sample loaded onto the column was saved and later assayed by ITR qPCR, ELISA against AAV antigens, and ELISA against HEK293 HCP antigens. The column was then re-equilibrated (Wash 1, W1) with 10 column volumes of 50 mM TrisHCl and 125 mM NaCl at pH 8.5. A sample of the flow through was saved and later assayed by ITR qPCR, ELISA against AAV antigens, and ELISA against HEK293 HCP antigens.

The column was then washed with 10 column volumes of Wash 2 (W2): 100 mM Taurine, 125 mM NaCl, at pH 8.5. The column was then washed with 10 column volumes of Wash 3 (W3): 100 mM Glycine at pH 8.5. The column was then washed with 10 column volumes of Wash 4 (W4): 50 mM Taurine, 50% (w/w) ethylene glycol, 0.1% octylglycopyranoside, at pH 8.5. A sample from eluate of each of W2, W3 and W4 was taken and assayed according to ITR qPCR, ELISA against AAV antigens, and ELISA against HEK293 HCP antigens.

Elution was undertaken by first applying 10 column volumes of the following elution buffer to the column: 50 mM Taurine, 60% (w/w) ethylene glycol, 750 mM NaCl, 0.1% octylglycopyranoside, at pH 8.0. The column was then washed with 10 column volumes of a Wash 5 (W5): 50 mM TrisHCl and 125 mM NaCl at pH 8.5. Elution was continued by next applying 10 column volumes of the following elution buffer to the column: 1 M $(NH_4)_2SO_4$, 50 mM TrisHCl and 50% (v/v) ethylene glycol, at pH 7.0. The column was then washed with 50 mM TrisHCl and 125 mM NaCl at pH 8.5. The column was then regenerated by applying to the column 10 column volumes of a solution comprising 100 mM glycine and 200 mM NaCl, at pH 2.7.

The above test procedure is described in more detail in Table 26. A linear flow rate of 39 cm/h was applied in all steps.

TABLE 26

| STEP | |
|---|---|
| Equilibration | 100 mM Glycine |
| | 200 mM NaCl |
| | pH 2.7 |
| LOAD | MUQ-FT |
| Wash 1 | 50 mM Tris HCl |
| (Re-equilibration) | 125 mM NaCl |
| | pH 8.5 |
| Wash 2 | 100 mM Taurine |
| | 0.5% PEG 6000 |
| | pH 6.0 |
| Wash 3 | 100 mM Glycine |
| | pH 8.5 |
| Wash 4 | 50 mM Taurine |
| | 50% (w/w) Ethylene glycol |
| | 0.1% Octylglycopyranoside |
| | pH 8.5 |
| ELUTION 1 | 50 mM Taurine |
| | 60% (w/w) Ethylene glycol |
| | 750 mM NaCl |
| | 0.1% Octylglycopyranoside |
| | pH 8.0 |
| Wash 5 | 50 mM Tris HCl |
| | 125 mM NaCl |
| | pH 8.5 |
| ELUTION 2 | 1M (NH4)2SO4 |
| | 50 mM Tris HCl |
| | 50% (v/v) Ethylene glycol |
| | pH 7.0 |
| Wash 6 | 50 mM Tris HCl |
| | 125 mM NaCl |
| | pH 8.5 |
| Regeneration | 100 mM Glycine |
| | 200 mM NaCl |
| | pH 2.7 |

Figure 9:
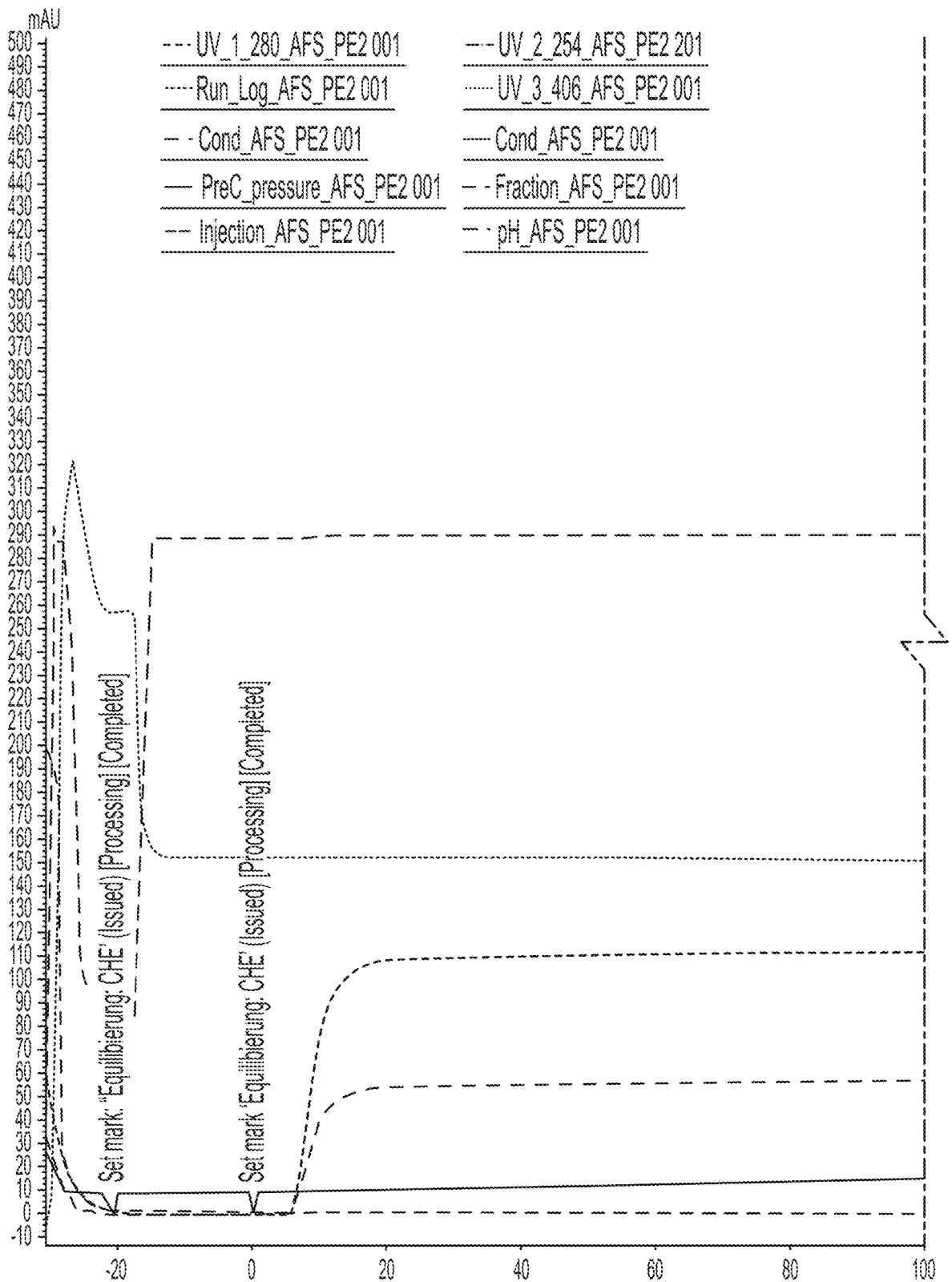
FIG. 9 depicts the chromatogram of the separation procedure according to Example 12.
Figure 9:
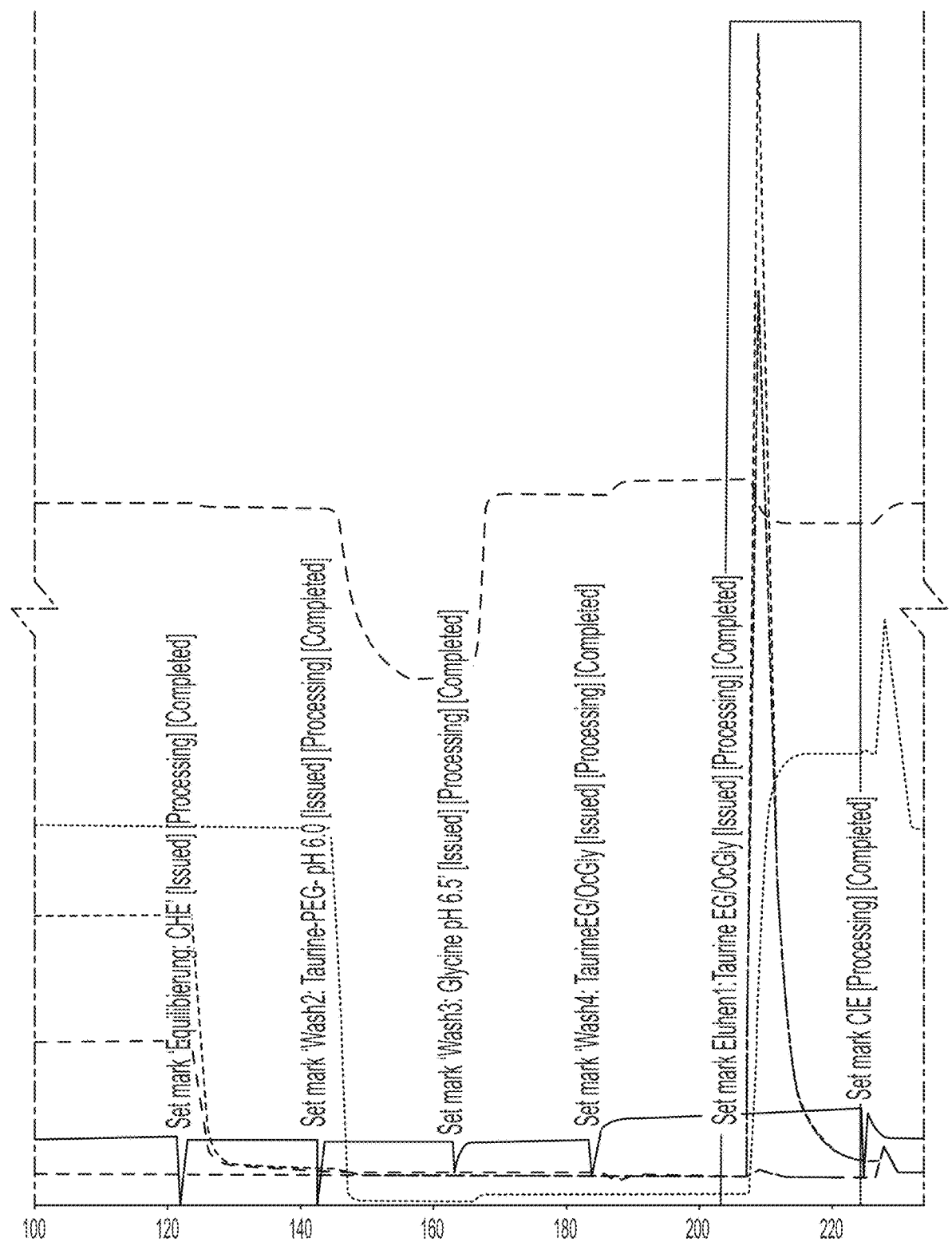
Figure 9:
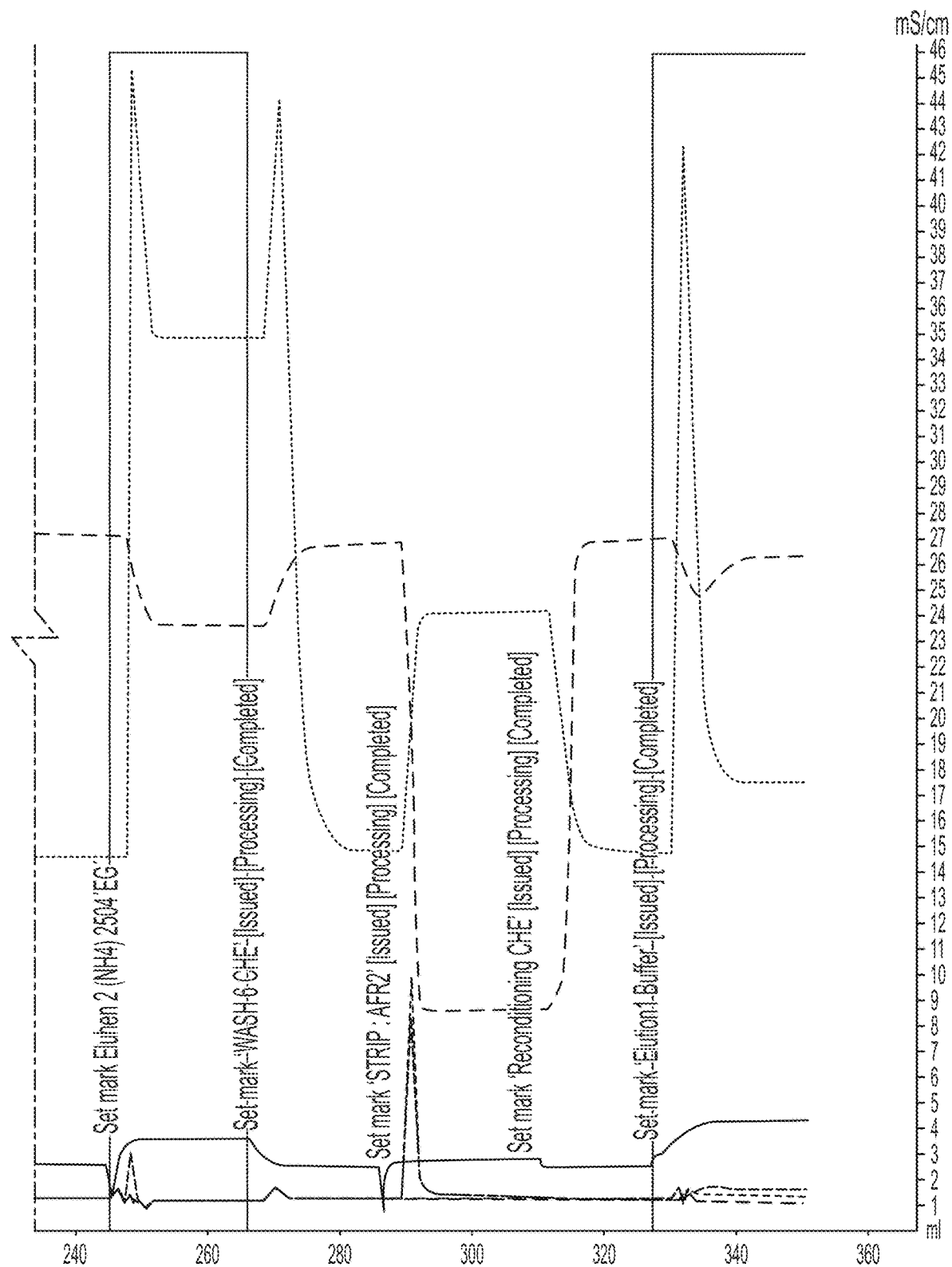

The samples taken were assayed by each of ITR qPCR and ELISA (as described in Example 8 above) against AAV antigens and ELISA against HEK293 HCP to assess yield and whether losses may have occurred in the steps. The chromatogram associated with the above example is shown in FIG. 9. The following Table 27 shows the samples taken at each of the above steps, with the yield of each component shown in Table 28.

TABLE 27

| Step | Buffer | Flowrate | CV | Fraction |
|---|---|---|---|---|
| Resin activation | 100 mM Glycine pH 2.7 | 39 cm/h | 10 | Waste |
| Equilibration | 50 mM TrisHCl, 125 mM NaCl, pH 8.5 | | 10 | Waste |
| Sample application | MUQ_FT (undiluted) | | X | FT/Wash 1 |
| WASH 1 Re-equilibration | 50 mM TrisHCl, 125 mM NaCl, pH 8.5 | | 10 | FT/Wash 1 |
| WASH 2 | 100 mM Taurine, 0.5% PEG 6000, pH 6.0 | | 10 | Wash 2 |
| WASH 3 | 100 mM Glycine, pH 8.5 | | 10 | Wash 3 |
| WASH4 | 50% Ethylene glycol (w/w), 50 mM Taurine, 0.1% Octylglycopyranoside, pH 8.5 | | 10 | Wash 4 |
| Elution1 | 50% Ethylene glycol (w/w), 50 mM Taurine, 0.1% Octylglycopyranoside, pH 8.0 + 750 mM NaCl | | 10 | Elution1 |
| WASH5 | 50 mM TrisHCl, 125 mM NaCl, pH 8.5 | | 10 | Wash 5 |
| Elution2 | 1M Ammonsulfate, 50% Ethylene glycol, 50 mM TrisHCl, pH 7.0 | | 10 | Elution1 |
| WASH6 | 50 mM TrisHCl, 125 mM NaCl, pH 8.5 | | 10 | Wash 6 |
| STRIP | 100 mM Glycine pH 2.7 | | 10 | Str/Ntr |

The "Wash 5" step reduced fronting effects in elution.

TABLE 28

| Step | Amount | AAV8 Antigen | Total AAV8 Antigen | % AAV8 Antigen | ITR-qPCR | Total ITR-qPCR | % ITR-qPCR |
|---|---|---|---|---|---|---|---|
| LOAD | 118.33 | 34.8 | 4111.968 | 100.00% | 30.4 | 4111.97 | 100.0 |
| FT/WASH 1 | 142.21 | 0.045 | 6.399 | 0.16% | n.d | n.d | n.d |
| WASH 2 | 20.47 | 0.0325 | 0.665 | 0.02% | n.d | n.d | n.d |
| WASH 3 | 20.44 | 0.0319 | 0.652 | 0.02% | n.d | n.d | n.d |
| WASH4 | 21.45 | 0.0159 | 0.341 | 0.01% | n.d | n.d | n.d |
| Elution1 | 22.14 | 177.95 | 3939.813 | 95.81% | 177.95 | 3939.81 | 95.81 |
| WASH5 | 20.82 | 1.02 | 21.236 | 0.52% | n.d | n.d | n.d |
| Elution2 | 22.31 | 0.55 | 12.271 | 0.30% | n.d | n.d | n.d |
| WASH6 | 21.11 | 0.0778 | 1.642 | 0.04% | n.d | n.d | n.d |
| STRIP | 22.69 | 6.349 | 144.059 | 3.50% | n.d | n.d | n.d |

Figure 10:
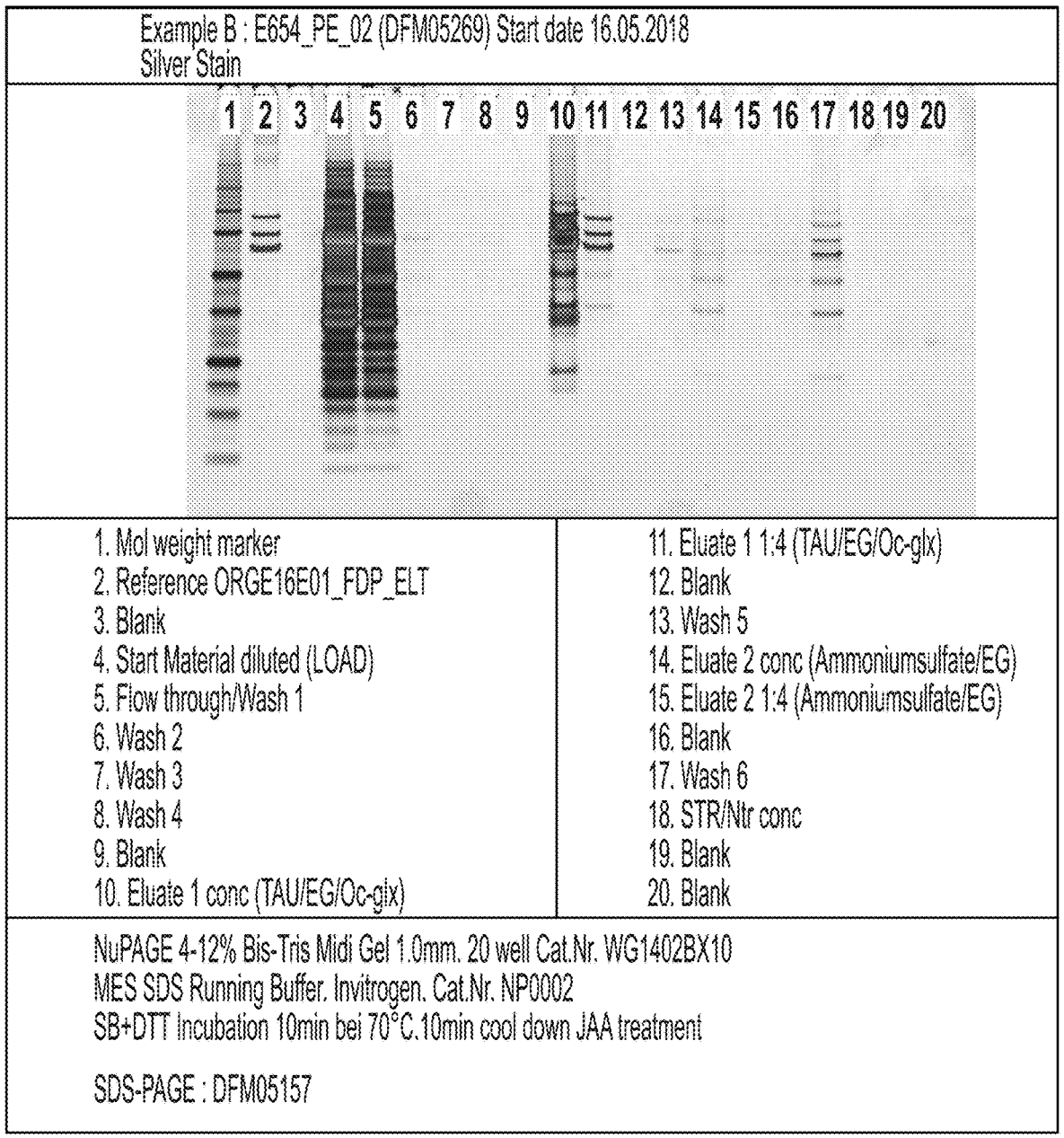
FIG. 10 depicts an SDS-PAGE silver stain gel showing the proteins present in various fractions from various wash steps and eluates according to Example 12.

Samples above were also assayed by SDS-PAGE and 12% silver stain to detect total protein. The SDS-PAGE assay results are shown in FIG. 10.

Example 13

AAV8 production was developed in a HEK293 cell line after transfection with a triple plasmid system containing encoding cDNA of the protein of interest and AAV8-. VP1. -VP2 and -VP3. From a 30 L Harvest aliquot the cells were disrupted by using a Megatron MT3000(Pall), followed by filtration of the AAV8 containing solution on a) depth filter PDP8 Area 0.5 m² b) depth filter V100 Area: 0.5 m² and c) Kleenpak Capsule 0.2 µm Area 0.15 m². The clarified cell free culture supernatant was concentrated and diafiltrated with Pall Omega T-Series Cassette 300 kDa. The viral particles were loaded onto a membrane adsorber (MustangQ. Pall Part Number XT140MSTGQP05) at nonbinding conditions for AAV8. The obtained AAV8 containing flow through was diluted 1:2 with a dilution buffer [100 mM Histidine, 200 mM NaCl, pH 8.5] additional 4 g of Polysorbate 80/kg was added to prepare a load for the AAV8-Affinity. The Histidine-containing Load was applied onto a column containing POROS™ CaptureSelect™ AAV8 Affinity Matrix (Cat. No. A30793, Thermo Fisher; ID 10 mm, Bed height 26 mm, volume 2.04 ml).

Samples from the various wash and elution steps were taken at various points to assay how much AAV8 is present in the sample. The assays indicate how much AAV8 was lost in various wash steps. The following test procedure was undertaken. First, a column containing ADK8/9 affinity resin ID 10 mm, with a bed height of 26 mm and a volume 2.04 ml, was equilibrated with at least ten column volumes of 50 mM TrisHCl and 125 mM NaCl at pH 8.5. The load was applied onto the column containing ADK8/9 affinity resin. A portion of the sample loaded onto the column was saved and later assayed by ITR qPCR and ELISA against AAV antigens (as described in Example 9 above), and ELISA against HEK293 HCP antigens (as described in Example 8 above). The column was then re-equilibrated (Wash 1, W1) with 10 column volumes of 50 mM Histidine and 100 mM NaCl at pH 8.5. A sample of the flow through was saved and later assayed by ITR qPCR and ELISA (as described in Examples 8 and 9 above) against AAV antigens, and ELISA against HEK293 HCP antigens.

The column was then washed with 10 column volumes of Wash 2 (W2): 200 mM Bis-Tris, 16.6 g S/D solution (Triton X-100; polysorbate 80; TNBP=10.87; 3.31:3.01 (by weight), at pH 6.0. The column was then washed with 10 column volumes of Wash 3 (W3): 10 mM Na-Citrate at pH 8.5. The column was then washed with 10 column volumes of Wash 4 (W4):100 mM Arginine-HCl, 100 mM Lysine-HCl, 100 mM Histidine-HCl, 2 mM N-Acetyl-D,L-tryptophan, at pH 8.5, with 20% (w/w) polysorbate 80. A sample from eluate of each of W2, W3 and W4 was taken and assayed according to ITR qPCR, ELISA against AAV antigens, and ELISA against HEK293 HCP antigens (as described in Examples 8 and 9 above).

Elution was undertaken by first applying 10 column volumes of the following elution buffer to the column: 20% (w/w) sucrose, 10% (w/w) sorbitol, 5% (w/w) mannitol (sucrose), 15% (w/w) glycerol, 50 mM Histidine, 800 mM NaCl, at pH 8.0. The column was then washed with 10 column volumes of a Wash 5 (W5): 50 mM Histidine and 100 mM NaCl at pH 8.5. Elution was continued by next applying 10 column volumes of the following elution buffer to the column: 50 mM TrisHCl, 750 mM NaCl, and 50% (w/w) DMSO, at pH 8.0. The column was then washed with 50 mM Histidine and 100 mM NaCl at pH 8.5. The column was then regenerated by applying to the column 10 column volumes of a solution comprising 100 mM glycine and 200 mM NaCl, at pH 2.7.

The above test procedure is described in more detail in Table 29. A linear flow rate of 39 cm/h was applied in all steps.

TABLE 29

| STEP | |
| --- | --- |
| Equilibration | 100 mM Glycine |
| | 200 mM NaCl |
| | pH 2.7 |
| LOAD | MUQ-FT dil 1:2 |
| Wash 1 | 50 mM Histidine |
| (Re-equilibration) | 100 mM NaCl |
| | pH 8.5 |
| Wash 2 | 200 mM Bis-Tris |
| | 16.6 g S/D solution |
| | (Triton X100:Polysorbate 80:TNBP = |
| | 10.87:3.31:3.01 (by weight) |
| | pH 6.0 |
| Wash 3 | 10 mmol Na-Citrate |
| | pH 8.5 |
| Wash 4 | 100 mM Arginine-HCl |
| | 100 mM Lysine-HCl |
| | 100 mM Histidine-HCl |
| | 2 mM N-Acetyl-D,L-Tryptophan |
| | pH 8.5 |
| | 20% (w/w) Polysorbate 80 |
| | (Elution / Wash + SD) |
| ELUTION 1 | 20% (w/w) Sucrose |
| | 10% (w/w) Sorbitol |
| | 5% (w/w) Mannitol (Sucrose) |
| | 15% (w/w) Glycerol |
| | 50 mM Histidine |
| | 800 mM NaCl |
| | pH 8.0 |
| Wash 5 | 50 mM Histidine |
| | 100 mM NaCl |
| | pH 8.5 |
| ELUTION 2 | 50 mM Tris HCl |
| | 750 mM NaCl |
| | 50% (w/w) DMSO |
| | pH 8.0 |
| Wash 6 | 50 mM Histidine |
| | 100 mM NaCl |
| | pH 8.5 |
| Regeneration | 100 mM Glycine |
| | 200 mM NaCl |
| | pH 2.7 |

The "Wash 5" step reduced fronting effects in elution. No elution of AAV8 was seen in the second elution step (Elution 2). For AAV8, DMSO could still be suitable as a wash buffer and/or as a buffer to potentially inactivate or disintegrate lipid-enveloped viruses.

Figure 11:
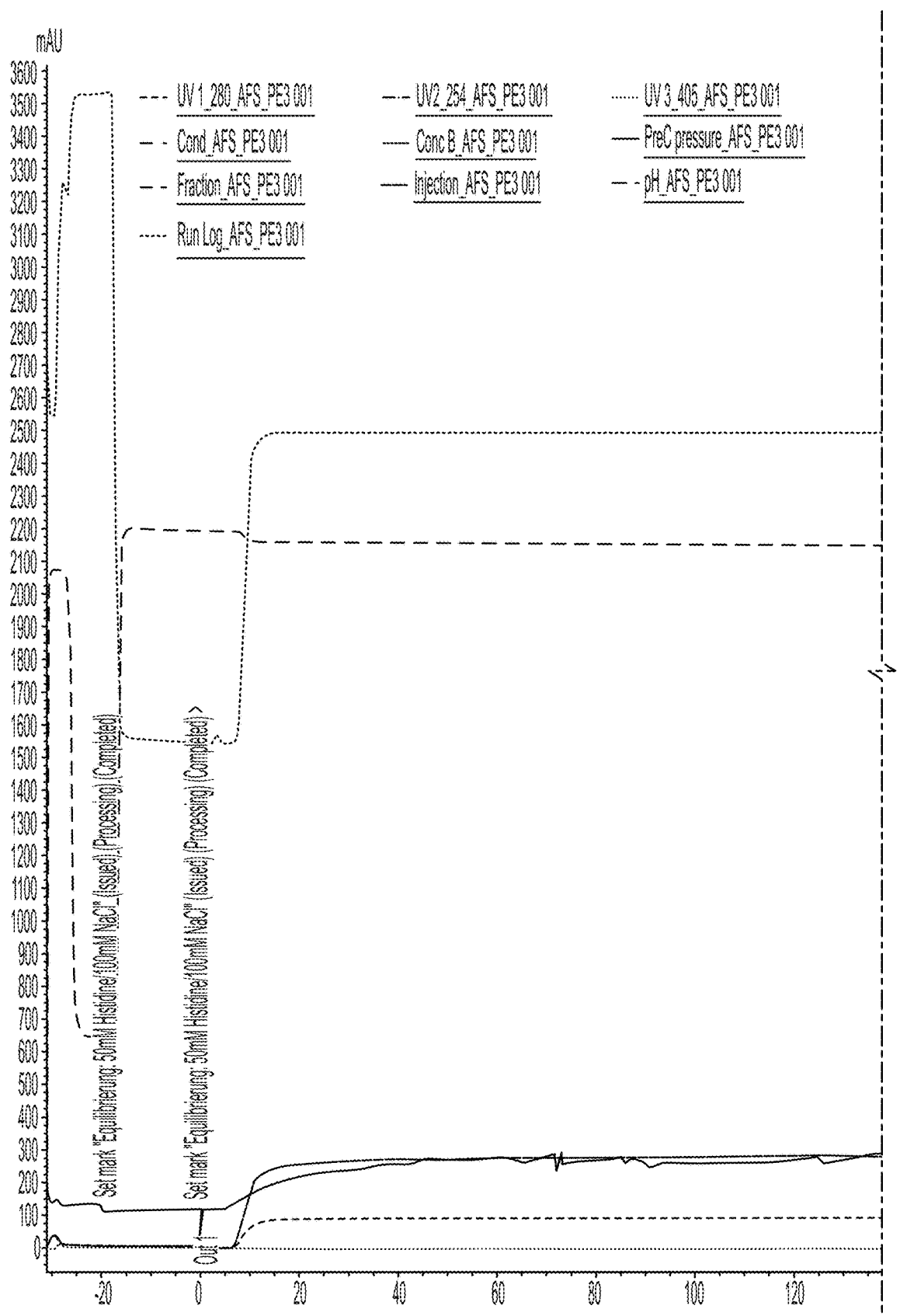
FIG. 11 depicts the chromatogram of the separation procedure according to Example 13.
Figure 11:
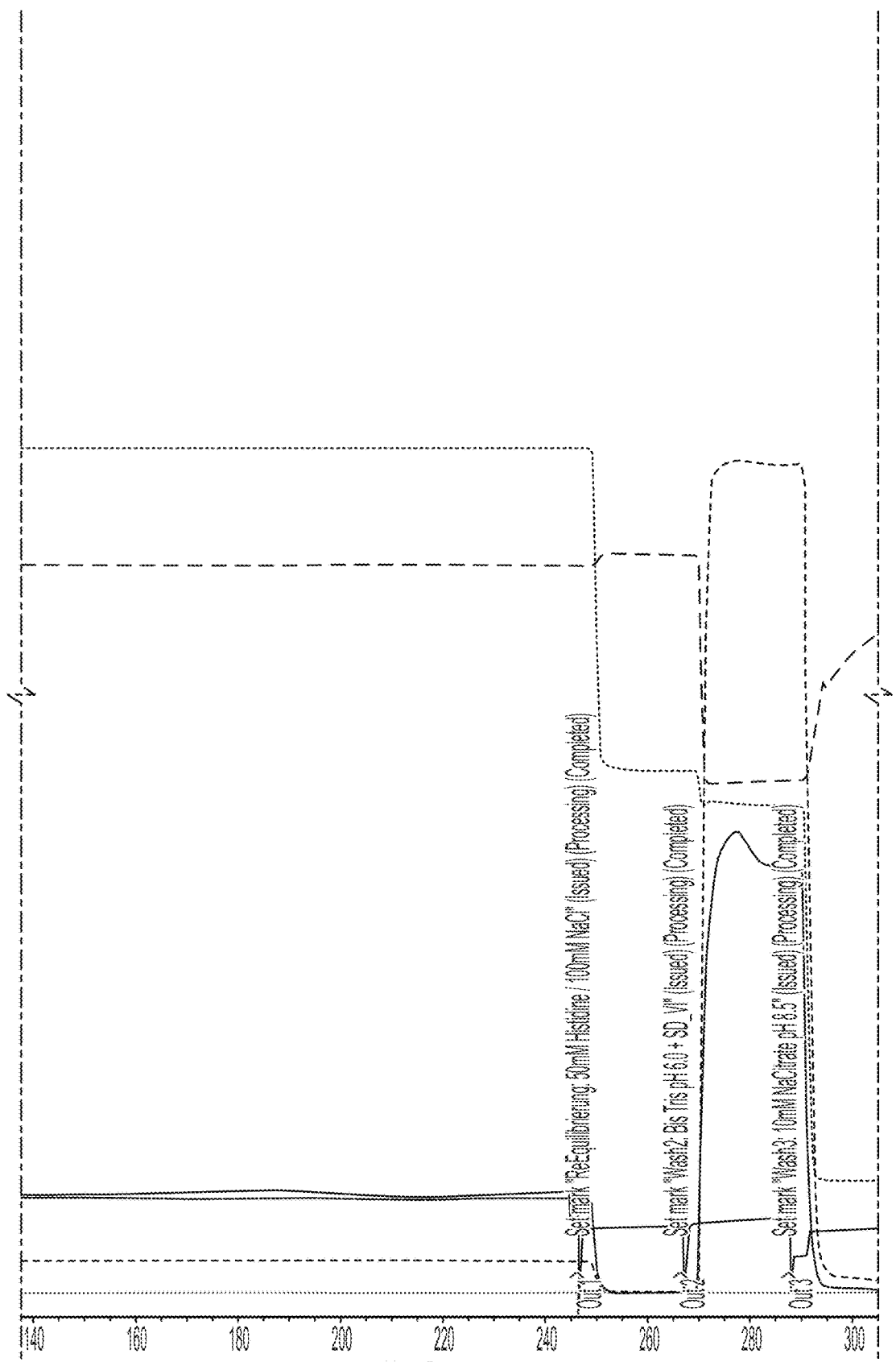
Figure 11:
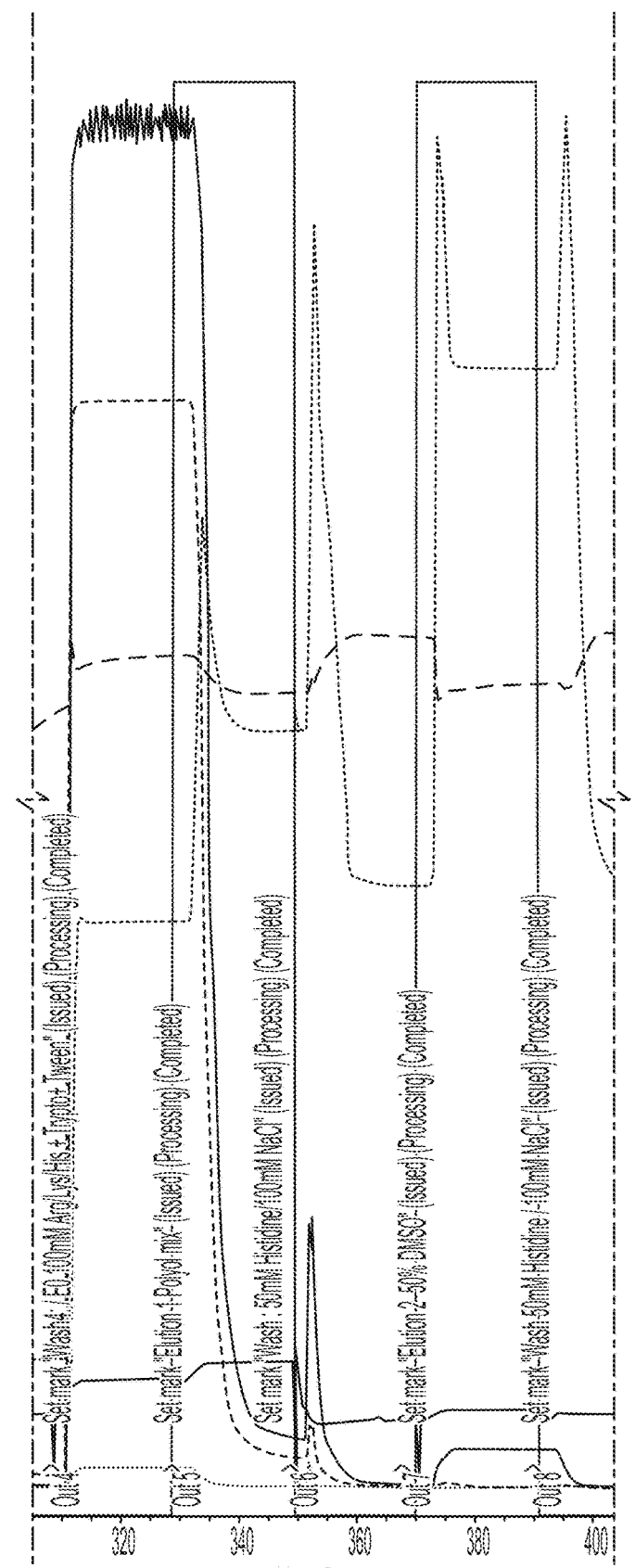
Figure 11:
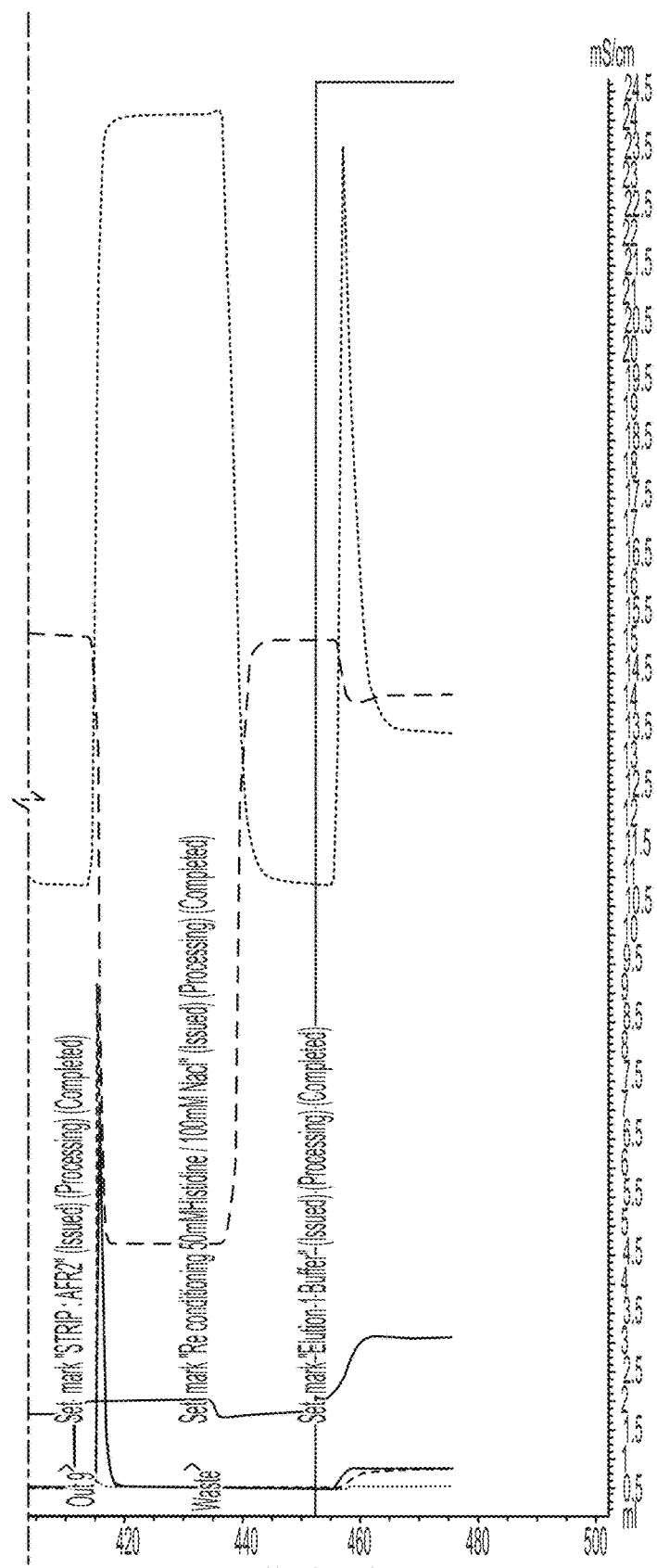

The samples taken were assayed by each of ITR qPCR, ELISA against AAV antigens and ELISA against HEK293 HCP (as described in Examples 8 and 9 above) to assess yield and whether losses may have occurred in the steps. The chromatogram associated with the above example is shown in FIG. 11. The following Table 30 shows the samples taken at each of the above steps, with the yield of each component shown in Table 31.

It is unexpected that elution of AAV8 from Capture Select AAV8 resin occurs at near to neutral conditions in presence of polyols and a certain amount of salt. The resin manufacturer proposed that elution would require acidic conditions below pH of 3.5. It was also surprising that elution could be triggered with sugars, sugar alcohols and/or a mixture of sugars and sugar alcohols. Also, it was unexpected that DMSO as a polar solvent could not elute AAV8 from Capture Select AAV8 resin.

TABLE 30

| Step | Buffer | Flowrate | CV | Fraction |
| --- | --- | --- | --- | --- |
| Resin activation | 100 mM Glycine pH 2.7 | 39 cm/h | 10 | Waste |
| Equilibration | 50 mM Histidine, 100 mM NaCl, pH 8.5 | | 10 | Waste |
| Sample application | MUQ_FT 1:2 | | X | FT/Wash 1 |
| WASH 1 Re-equilibration | 50 mM Histidine, 100 mM NaCl, pH 8.5 | | 10 | FT/Wash 1 |
| WASH 2 | 200 mM Bis-Tris + 16.6 g/kg S/D solution | | 10 | Wash 2 |
| WASH 3 | 10 mmol Na-Citrate, pH 8.5 | | 10 | Wash 3 |
| WASH4 | 100 mM Arginine, 100 mM Lysine, 100 mM Histidine 2 mM N-Acetyl-D,L-Tryptophan, 20% (w/w) Polysorbate 80, pH 8.5 | | 10 | Wash 4 |
| Elution1 | 20% Sucrose, 10% (w/w) Sorbitol, 5% (w/w) Mannitol, 15% (w/w) Glycerol 50 mM Histidine, 800 mM NaCl, pH 8.0 | | 10 | Elution1 |
| WASH5 | 50 mM Histidine, 100 mM NaCl, pH 8.5 | | 10 | Wash 5 |
| Elution2 | 50 mM Tris HCl, 750 mM NaCl, 50% (w/w) DMSO, pH 8.0 | | 10 | Elution2 |
| WASH6 | 50 mM Histidine, 100 mM NaCl, pH 8.5 | | 10 | Wash 6 |
| STRIP | 100 mM Glycine pH 2.7 | | 10 | Str/Ntr |

The "Wash 5" step reduced fronting effects in elution. No elution of AAV8 was seen in the second elution step (Elution 2).

TABLE 31

| Step | Amount | AAV8 Antigen | Total AAV8 Antigen | % AAV8 Antigen | ITR-qPCR | Total ITR-qPCR | % ITR-qPCR |
| --- | --- | --- | --- | --- | --- | --- | --- |
| LOAD | 244.41 | 17.2 | 4191.632 | 100.00% | 3.63 | 4191.6 | 100 |
| FT/WASH 1 | 368.03 | 0.037 | 13.617 | 0.32% | n.d | n.d | n.d |
| WASH 2 | 21.24 | 0.0755 | 1.604 | 0.04% | n.d | n.d | n.d |
| WASH 3 | 20.61 | 0.031 | 0.639 | 0.02% | n.d | n.d | n.d |
| WASH4 | 21.09 | 0.016 | 0.337 | 0.01% | n.d | n.d | n.d |
| Elution1 | 23.68 | 47.35 | 1121.248 | 26.75% | 126 | 2980 | 33.63 |
| WASH5 | 21.45 | 6.1 | 130.845 | 3.12% | n.d | n.d | n.d |

TABLE 31-continued

| Step | Amount | AAV8 Antigen | Total AAV8 Antigen | % AAV8 Antigen | ITR-qPCR | Total ITR-qPCR | % ITR-qPCR |
|---|---|---|---|---|---|---|---|
| Elution2 | 22.22 | 0.016 | 0.356 | 0.01% | n.d | n.d | n.d |
| WASH6 | 21.72 | 0.031 | 0.673 | 0.02% | n.d | n.d | n.d |
| STRIP | 23.47 | 113.4 | 2661.5 | 63.5% | 8.27 | 194 | 2.19 |

Figure 12:
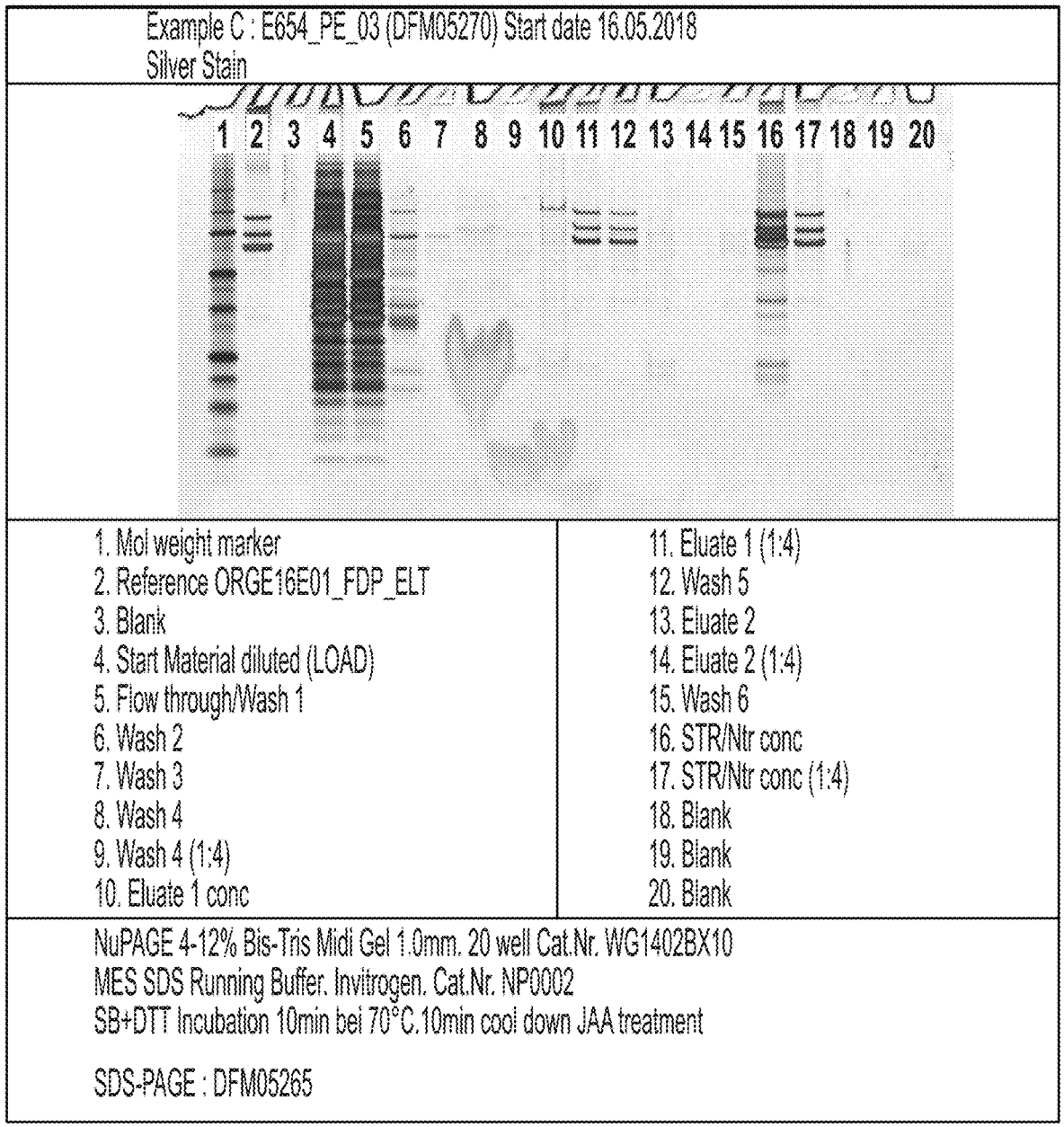
FIG. 12 depicts an SDS-PAGE silver stain gel showing the proteins present in various fractions from various wash steps and eluates according to Example 13.

Samples above were also assayed by SDS-PAGE and 12% silver stain to detect total protein. The SDS-PAGE assay results are shown in FIG. 12.

Example 14

AAV2 production was developed in a HEK293 cell line after transfection with a triple plasmid system containing encoding cDNA of the protein of interest and AAV2-. VP1. -VP2 and -VP3. The AAV2 sample was diluted with 150 mM NaCl, 20 mM TrisHCl, pH 7.4 to provide a Load. The Load was applied onto a column containing POROS™ CaptureSelect™ AAVX Affinity Matrix (Cat. No.: A36739, Thermo Fisher; ID 10 mm, Bed height 25 mm, volume 1.96 ml).

Samples from the various wash and elution steps were taken at various points to assay how much AAV2 is present in the sample. The assays indicate how much AAV2 was lost in various wash steps. The following test procedure was undertaken. First, a column containing ADK8/9 affinity resin ID 10 mm, with a bed height of 25 mm and a volume 1.96 ml, was equilibrated with at least ten column volumes of 20 mM TrisHCl, 150 mM NaCl at pH 7.4. The load was applied onto the column containing ADK8/9 affinity resin. A portion of the sample loaded onto the column was saved and later assayed by ITR qPCR, ELISA against AAV antigens, and ELISA against HEK293 HCP antigens (as described in Examples 8 and 9 above). The column was then re-equilibrated (Wash 1, W1) with 10 column volumes of 20 mM TrisHCl, 150 mM NaCl at pH 7.4. A sample of the flow through was saved and later assayed by ITR qPCR, ELISA against AAV antigens, and ELISA against HEK293 HCP antigens (as described in Examples 8 and 9 above).

The column was then washed with 10 column volumes of Wash 2 (W2): 100 mM NaAcetate, 0.1% Polysorbate 80 at pH 6.0. The column was then washed with 10 column volumes of Wash 3 (W3): 50 mM TrisHCl, 125 mM NaCl at pH 8.5. The column was then washed with 10 column volumes of Wash 4 (W4): 50 mM TrisHCl, 50% (w/w) Ethylene glycol at pH 8.5. The column was then washed with 10 column volumes of Wash 5 (W5): 50 mM TrisHCl, 60% (w/w) Ethylene glycol+750 mM NaCl pH 8.0. The column was then washed with 10 column volumes of Wash 6 (W6): 20 mM TrisHCl, 150 mM NaCl, pH 7.4. A sample from eluate of each of W2, W3 and W4 was taken and assayed according to ITR qPCR, ELISA against AAV antigens, and ELISA against HEK293 HCP antigens (as described in Examples 8 and 9 above).

Elution was undertaken by first applying 10 column volumes of the following elution buffer to the column: 100 mM Glycine-HCl, 200 mM NaCl, pH 2.5. The column was then washed with 10 column volumes of a Wash 7 (W7): 20 mM TrisHCl, 150 mM NaCl at pH 7.4. The column was stripped with 10 column volumes of 50 mM phosphoric acid pH 2.0, washed with 10 column volumes of a Wash 8 (W8): 20 mM TrisHCl, 150 mM NaCl at pH 7.4, and then stripped with 10 column volumes 50 mM phosphoric acid pH 2.0.

The above test procedure is described in more detail in Table 32. A linear flow rate of 39 cm/h was applied in all steps.

TABLE 32

| STEP | |
|---|---|
| Equilibration | 20 mM TrisHCl, 150 mM NaCl, pH 7.4 |
| Wash 1 (Re-equilibration) | 20 mM TrisHCl, 150 mM NaCl, pH 7.4 |
| Wash 2 | 100 mM NaAcetate, 0.1% Polysorbate80, pH 6.0 |
| Wash 3 | 50mM TrisHCl, 125 mM NaCl, pH 8.5 |
| Wash 4 | 50 mM TrisHCl, 50% (w/w) Ethylenglyocl, pH 8.5 |
| Wash 5 | 50 mM TrisHCl, 60% (w/w) Ethylene glycol + 750 mM NaCl pH 8.0 |
| Wash 6 | 20 mM TrisHCl, 150 mM NaCl, pH 7.4 |
| ELUTION 1 | 100 mM GlycineHCl, 200 mM NaCl, pH 2.5 |
| Wash 7 | 20 mM TrisHCl, 150 mM NaCl, pH 7.4 |
| STRIP- first | 50 mM Phosphoric acid pH 2.0 |
| Wash 8 | 20 mM TrisHCl, 150 mM NaCl, pH 7.4 |
| STRIP- second | 50 mM Phosphoric acid pH 2.0 |

Figure 13:
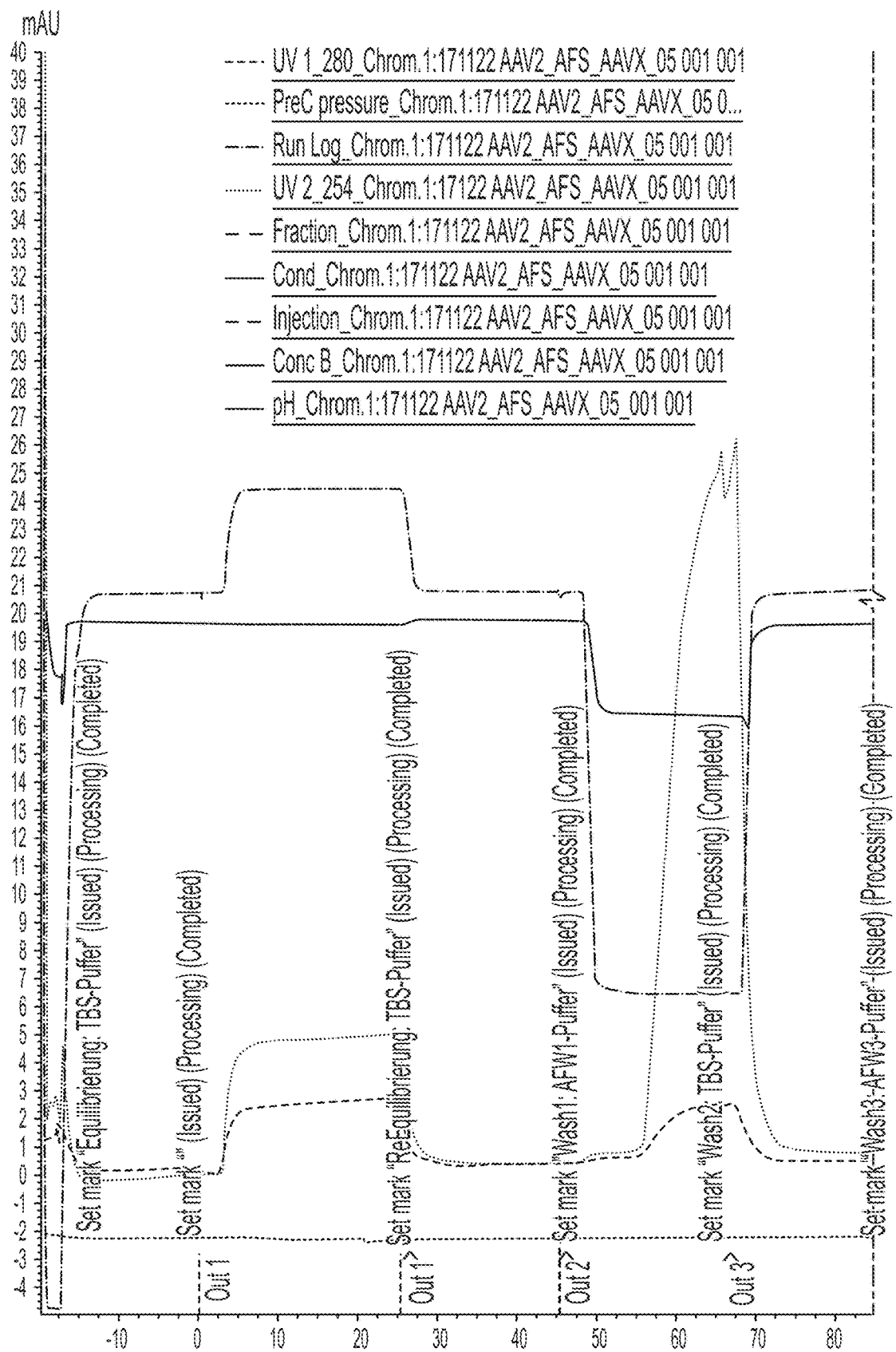
FIG. 13 depicts the chromatogram of the separation procedure according to Example 14.
Figure 13:
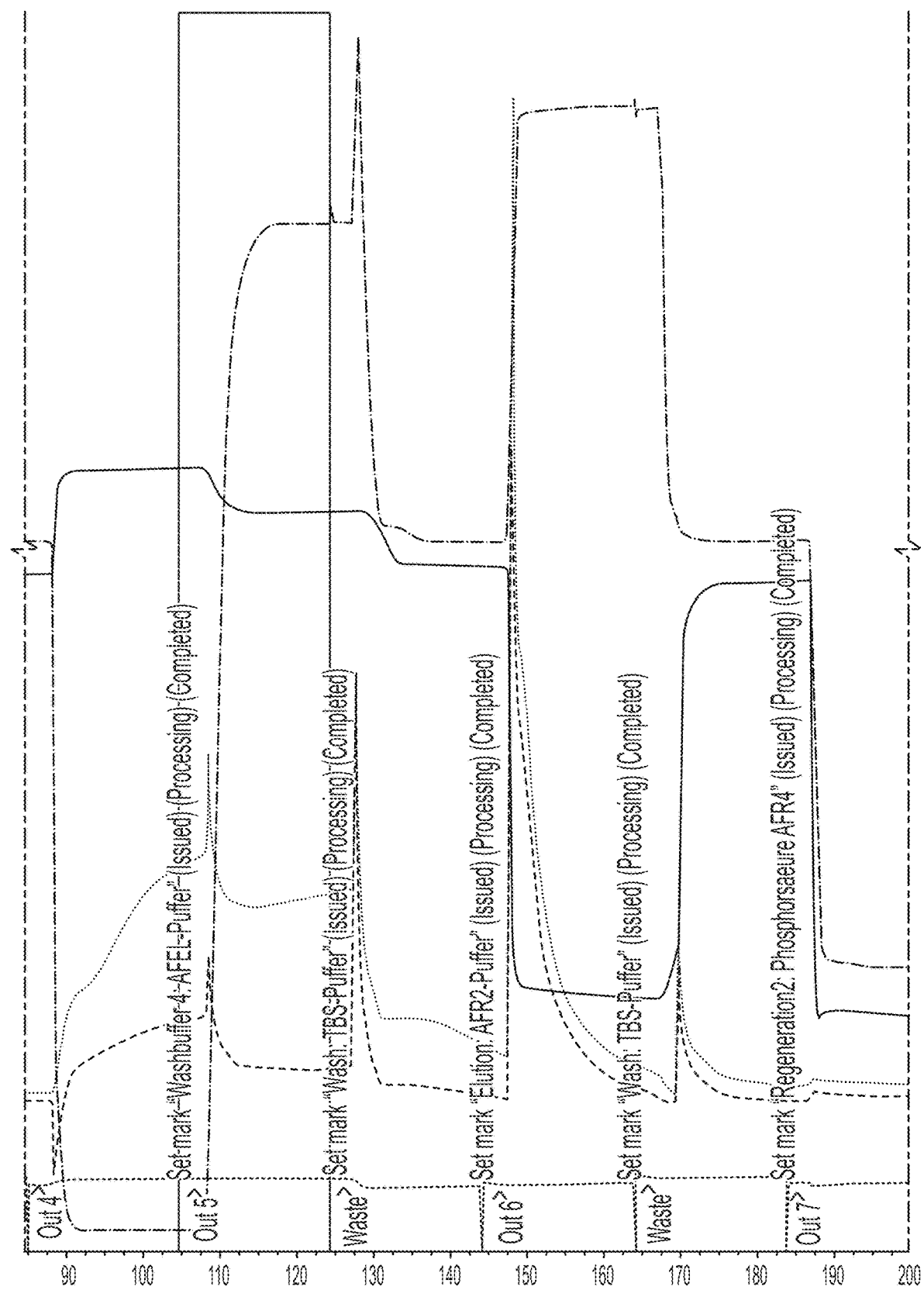
Figure 13:
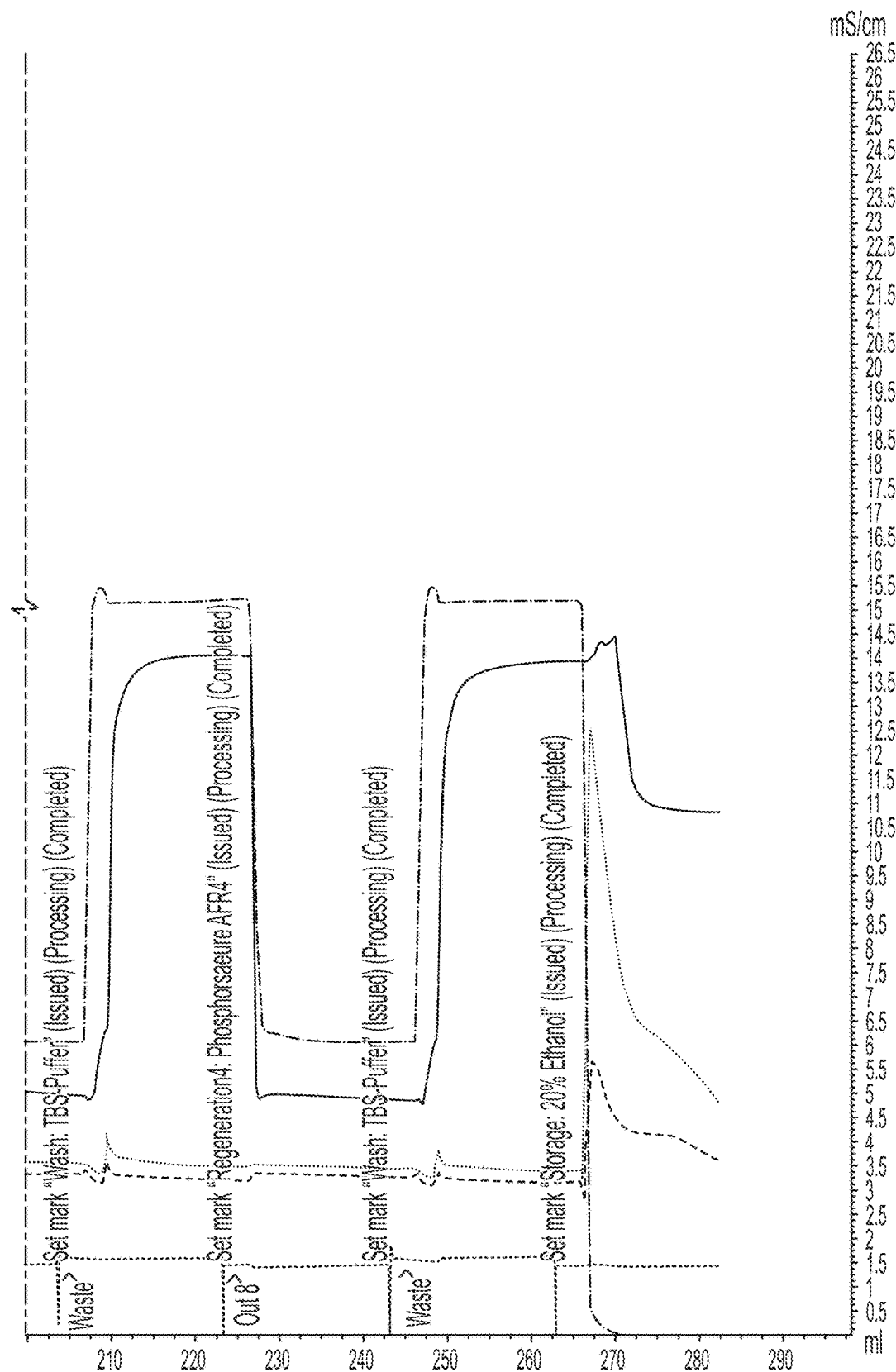

The samples taken were assayed by each of ITR qPCR, ELISA against AAV antigens and ELISA against HEK293 HCP (as described in Examples 8 and 9 above) to assess yield and whether losses may have occurred in the steps. The chromatogram associated with the above example is shown in FIG. 13. The following Table 33 shows the samples taken at each of the above steps, with the yield of each component shown in Table 34.

TABLE 33

| Step | Buffer | Flowrate | CV | Fraction |
|---|---|---|---|---|
| Resin activation | — | 39 cm/h | 10 | Waste |
| Equilibration | 20 mM TrisHCl, 150 mM NaCl, pH 7.4 | | 10 | Waste |
| Sample application | 2x Flow through from TMAE | | X | FT/Wash1 |
| WASH 1 Re-equilibration | 20 mM TrisHCl, 150 mM NaCl, pH 7.4 | | 10 | FT/Wash1 |
| WASH 2 | 100 mM NaAcetate, 0.1% Polysorbate80, pH 6.0 | | 10 | Wash 2 |
| WASH 3 | 50 mM TrisHCl, 125 mM NaCl, pH 8.5 | | 10 | Wash 3 |
| WASH 4 | 50 mM TrisHCl, 50% (w/w) Ethylenglyocl, pH 8.5 | | 10 | Wash 4 |
| WASH 5 | 50 mM TrisHCl, 60% (w/w) Ethylene glycol + 750 mM NaCl pH 8.0 | | 10 | Wash 5 |
| WASH 6 | 20 mM TrisHCl, 150 mM NaCl, pH 7.4 | | 10 | Wash 6 |
| ELUTION 1 | 100 mM GlycineHCl, 200 mM NaCl, pH 2.5 | | 10 | Elution |
| WASH 7 | 20 mM TrisHCl, 150 mM NaCl, pH 7.4 | | | Wash 7 |
| STRIP | 50 mM Phosphoric acid pH 2.0 | | 10 | Strip 1 |
| WASH 8 | 20 mM TrisHCl, 150 mM NaCl, pH 7.4 | | 10 | Wash 8 |
| STRIP 2 | 50 mM Phosphoric acid pH 2.0 | | 10 | Strip 2 |

TABLE 34

| Step | Amount [ml] | ITR-qPCR E + 11 vg/ml | Total ITR-qPCR E + 11 vg | % ITR-qPCR |
|---|---|---|---|---|
| LOAD | 22.57 | 12.6 | 284.38 | 100.0% |
| Elution 1 | 19.97 | 14.0 | 279.58 | 98.3% |

Figure 14:
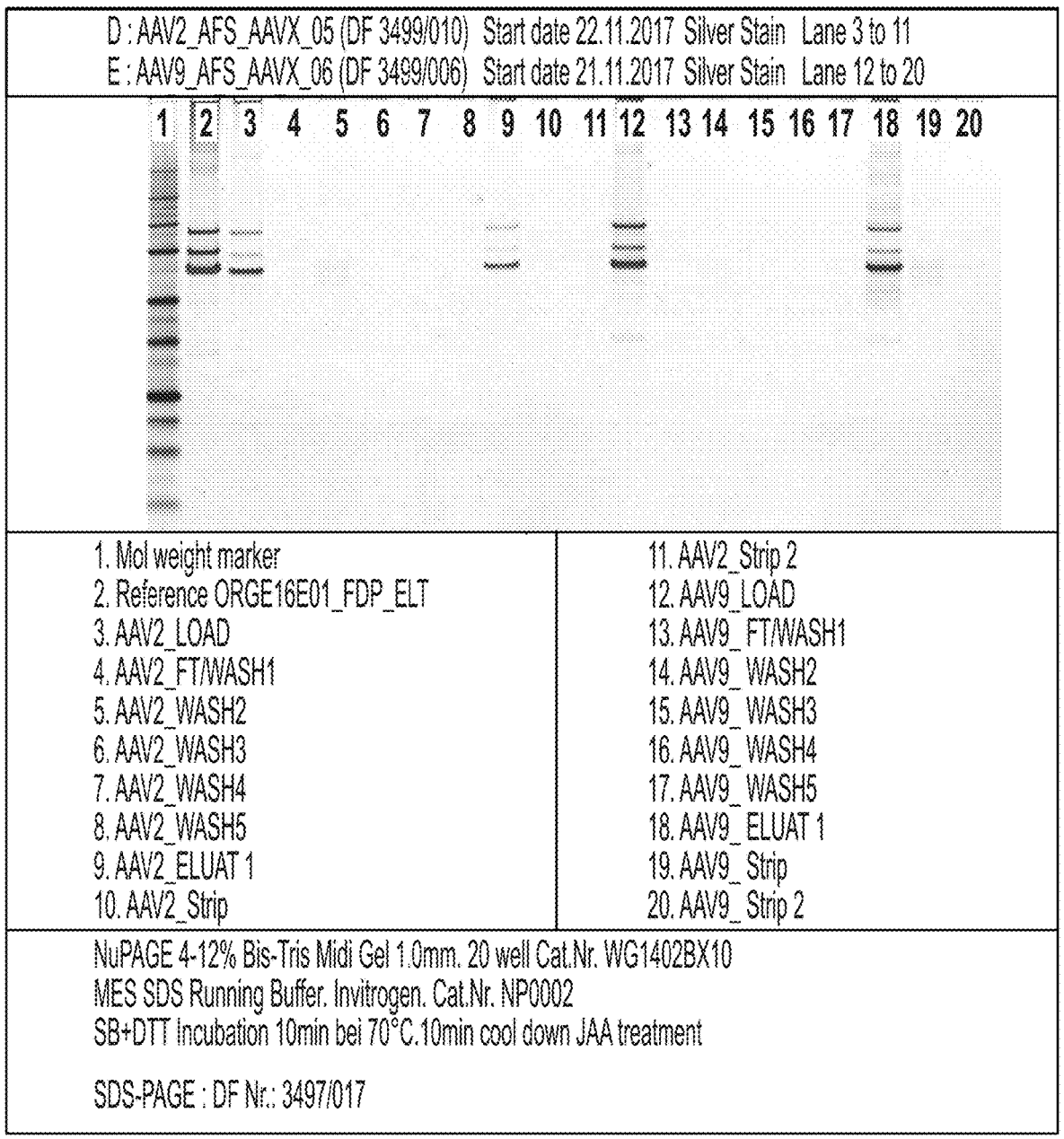
FIG. 14 depicts an SDS-PAGE silver stain gel showing the proteins present in various fractions taken from wash steps and eluates as described in Example 14.

Samples above were also assayed by SDS-PAGE and 12% silver stain to detect total protein. The results of the SDS-PAGE assay are shown in FIG. 14 (see lanes 2-11).

Figure 15:
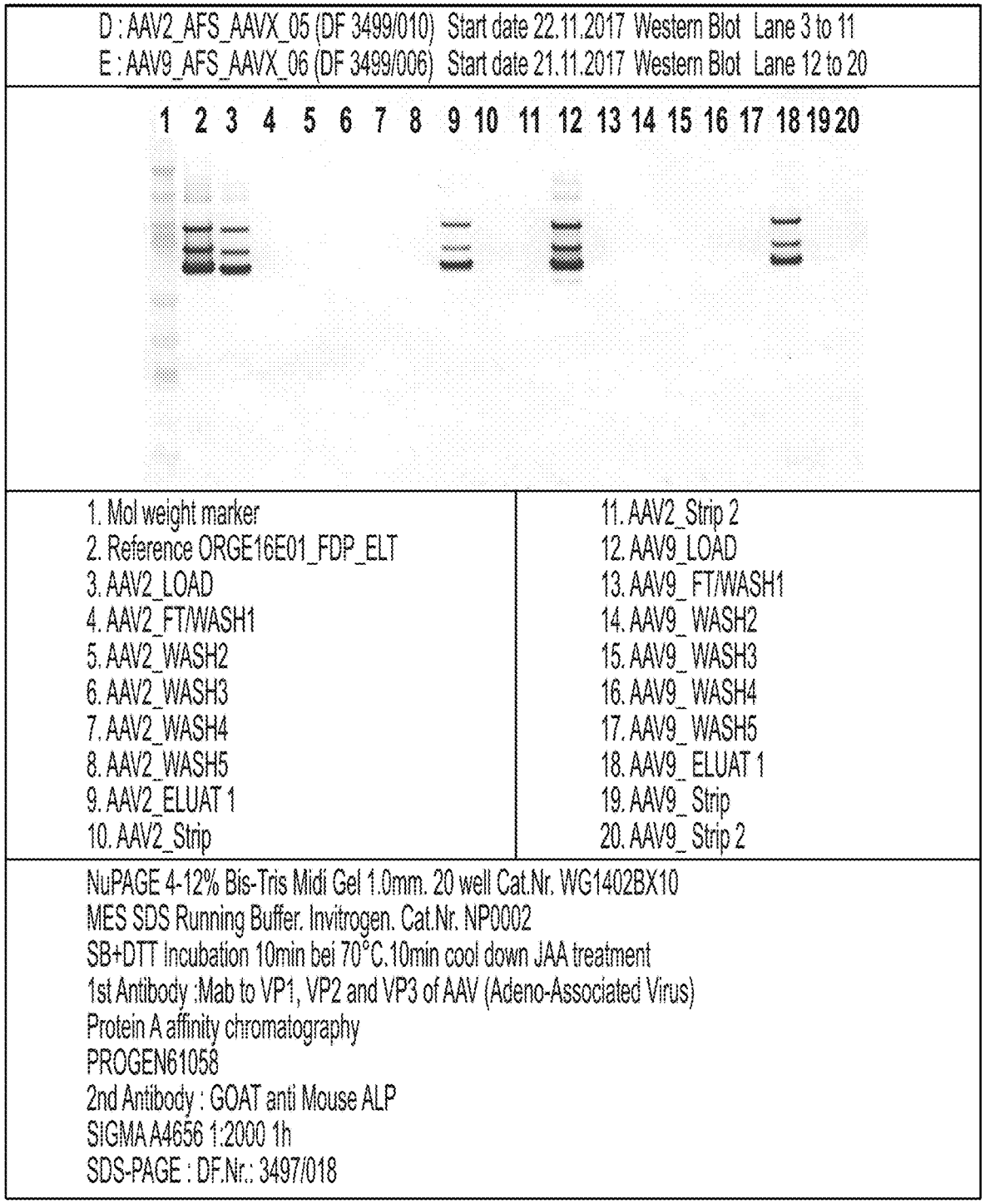
FIG. 15 depicts a Western Blot against AAV antigens from the various fractions taken from wash steps and eluates as described in Example 14.

Samples were then assayed by SDS-PAGE and a Western blot against AAV antigens. The primary antibodies are monoclonal antibodies against VP1, VP2 and VP3 of AAV while the secondary antibody is a goat anti-mouse coupled with alkaline phosphatase. The results of an Western blot assay are shown in FIG. 15 (see lanes 2-11).

Example 15

AAV9 production was developed in a HEK293 cell line after transfection with a triple plasmid system containing encoding cDNA of the protein of interest and AAV9-, VP1, -VP2 and -VP3. The AAV9 sample was diluted with 150 mM NaCl, 20 mM TrisHCl, pH 7.4 to provide a Load. The Load was applied onto a column containing POROS™ CaptureSelect™ AAVX Affinity Matrix (Cat. No.: A36739, Thermo Fisher; ID 10 mm, Bed height 25 mm, volume 1.96 ml).

Samples from the various wash and elution steps were taken at various points to assay how much AAV9 is present in the sample. The assays indicate how much AAV9 was lost in various wash steps. The following test procedure was undertaken. First, a column containing ADK8/9 affinity resin ID 10 mm, with a bed height of 25 mm and a volume 1.96 ml, was equilibrated with at least ten column volumes of 20 mM TrisHCl, 150 mM NaCl at pH 7.4. The load was applied onto the column containing ADK8/9 affinity resin. A portion of the sample loaded onto the column was saved and later assayed by ITR qPCR, ELISA against AAV antigens, and ELISA against HEK293 HCP antigens (as described in Examples 8 and 9 above). The column was then re-equilibrated (Wash 1, W1) with 10 column volumes of 20 mM TrisHCl, 150 mM NaC at pH 7.4. A sample of the flow through was saved and later assayed by ITR qPCR, ELISA against AAV antigens, and ELISA against HEK293 HCP antigens (as described in Examples 8 and 9 above).

The column was then washed with 10 column volumes of Wash 2 (W2): 100 mM NaAcetate, 0.1% Polysorbate 80 at pH 6.0. The column was then washed with 10 column volumes of Wash 3 (W3): 50 mM TrisHCl, 125 mM NaCl, at pH 8.5. The column was then washed with 10 column volumes of Wash 4 (W4): 50 mM TrisHCl, 50% (w/w) Ethylene glycol, at pH 8.5. The column was then washed with 10 column volumes of Wash 5 (W5): 50 mM TrisHCl, 60% (w/w) Ethylene glycol+750 mM NaCl pH 8.0. The column was then washed with 10 column volumes of Wash 6 (W6): 20 mM TrisHCl, 150 mM NaCl, pH 7.4. A sample from eluate of each of W2, W3 and W4 was taken and assayed according to ITR qPCR, ELISA against AAV antigens, and ELISA against HEK293 HCP antigens (as described in Examples 8 and 9 above).

Elution was undertaken by first applying 10 column volumes of the following elution buffer to the column: 100 mM Glycine HCl, 200 mM NaCl, pH 2.5. The column was then washed with 10 column volumes of a Wash 7 (W7): 20 mM TrisHCl, 150 mM NaCl at pH 7.4. The column was stripped with 10 column volumes of 50 mM phosphoric acid pH 2.0, washed with 10 column volumes of a Wash 8 (W8): 20 mM TrisHCl, 150 mM NaCl at pH 7.4, and then stripped with 10 column volumes 50 mM phosphoric acid pH 2.0.

The above test procedure is described in more detail in Table 35. A linear flow rate of 39 cm/h was applied in all steps.

TABLE 35

| STEP | |
|---|---|
| Equilibration | 20 mM TrisHCl, 150 mM NaCl, pH 7.4 |
| Sample Application | 2x flow through from TMAE |
| Wash 1 (Re-equilibration) | 20 mM TrisHCl, 150 mM NaCl, pH 7.4 |
| Wash 2 | 100 mM NaAcetate, 0.1% Polysorbate 80, pH 6.0 |
| Wash 3 | 50 mM TrisHCl, 125 mM NaCl, pH 8.5 |
| Wash 4 | 50 mM TrisHCl, 50% (w/w) Ethylene glycol, pH 8.5 |
| Wash 5 | 50 mM TrisHCl, 60% (w/w) Ethylene glycol +750mM NaCl pH 8.0 |
| Wash 6 | 20 mM TrisHCl, 150 mM NaCl, pH 7.4 |
| ELUTION 1 | 100 mM Glycine HCl, 200 mM NaCl, pH 2.5 |
| Wash 7 | 20 mM TrisHCl, 150 mM NaCl, pH 7.4 |
| STRIP- first | 50 mM Phosphoric acid pH 2.0 |
| Wash 8 | 20 mM TrisHCl, 150 mM NaCl, pH 7.4 |
| STRIP- second | 50 mM Phosphoric acid pH 2.0 |

Figure 16:
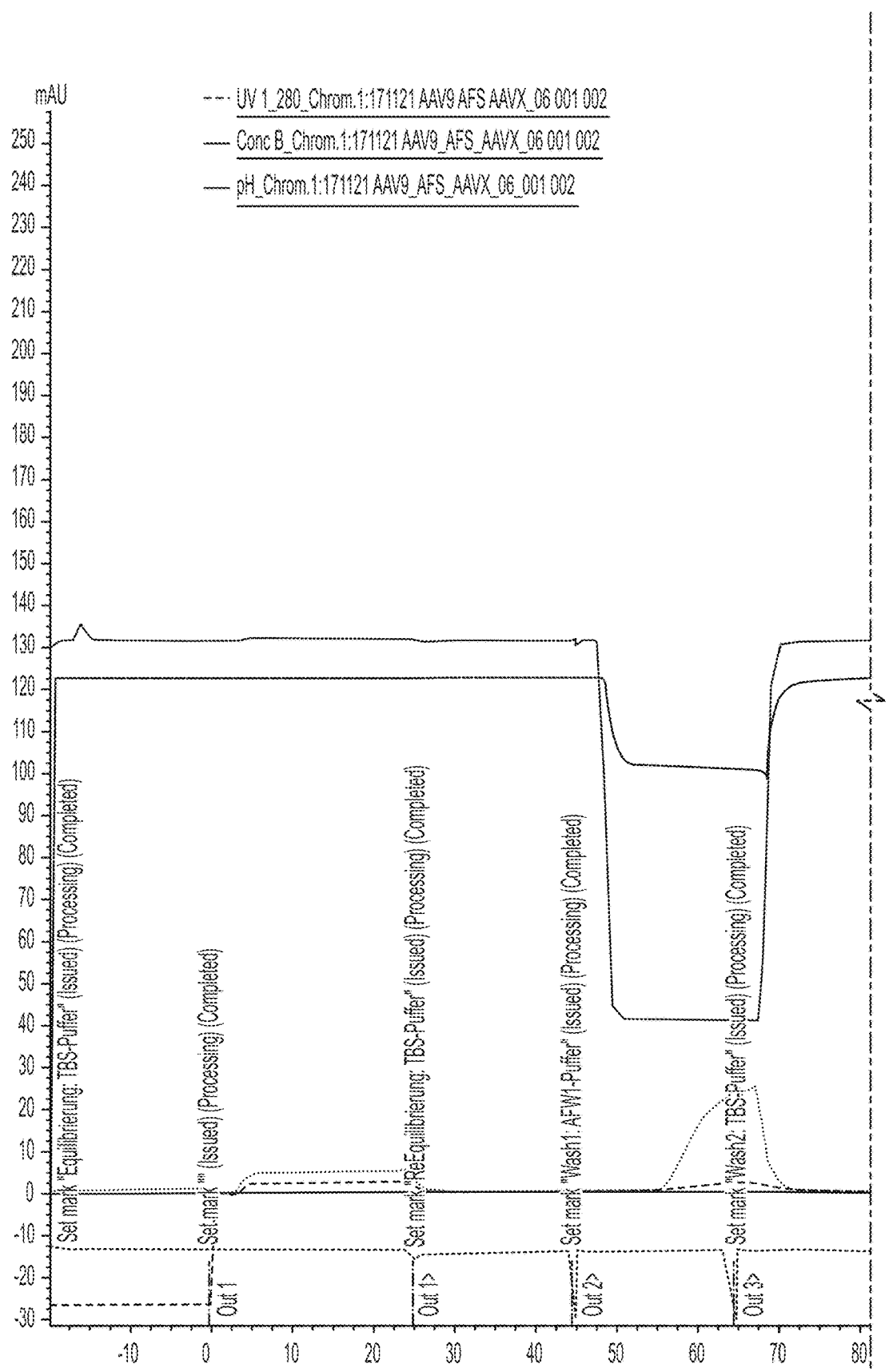
FIG. 16 depicts the chromatogram of the separation procedure according to Example 15.
Figure 16:
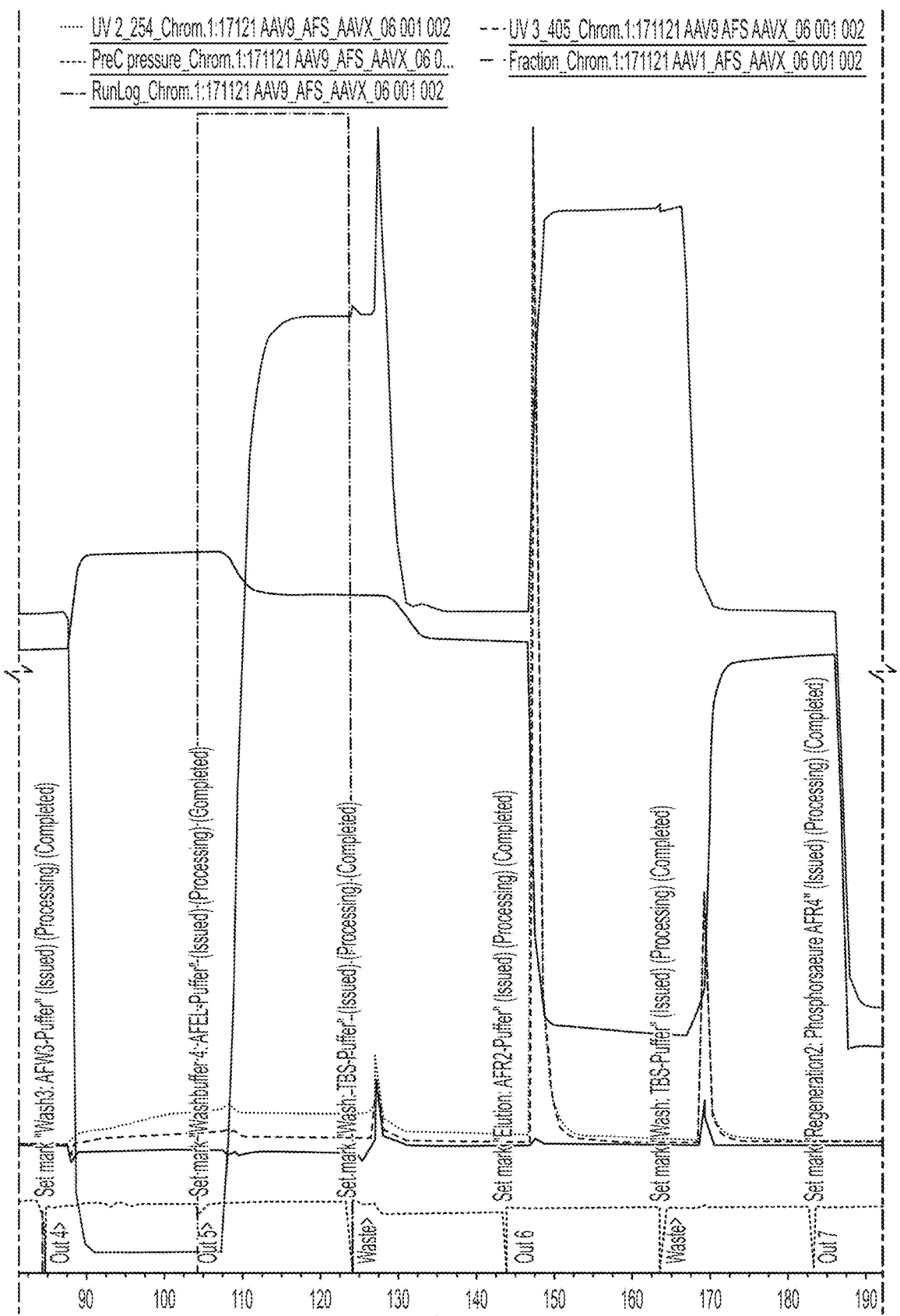
Figure 16:
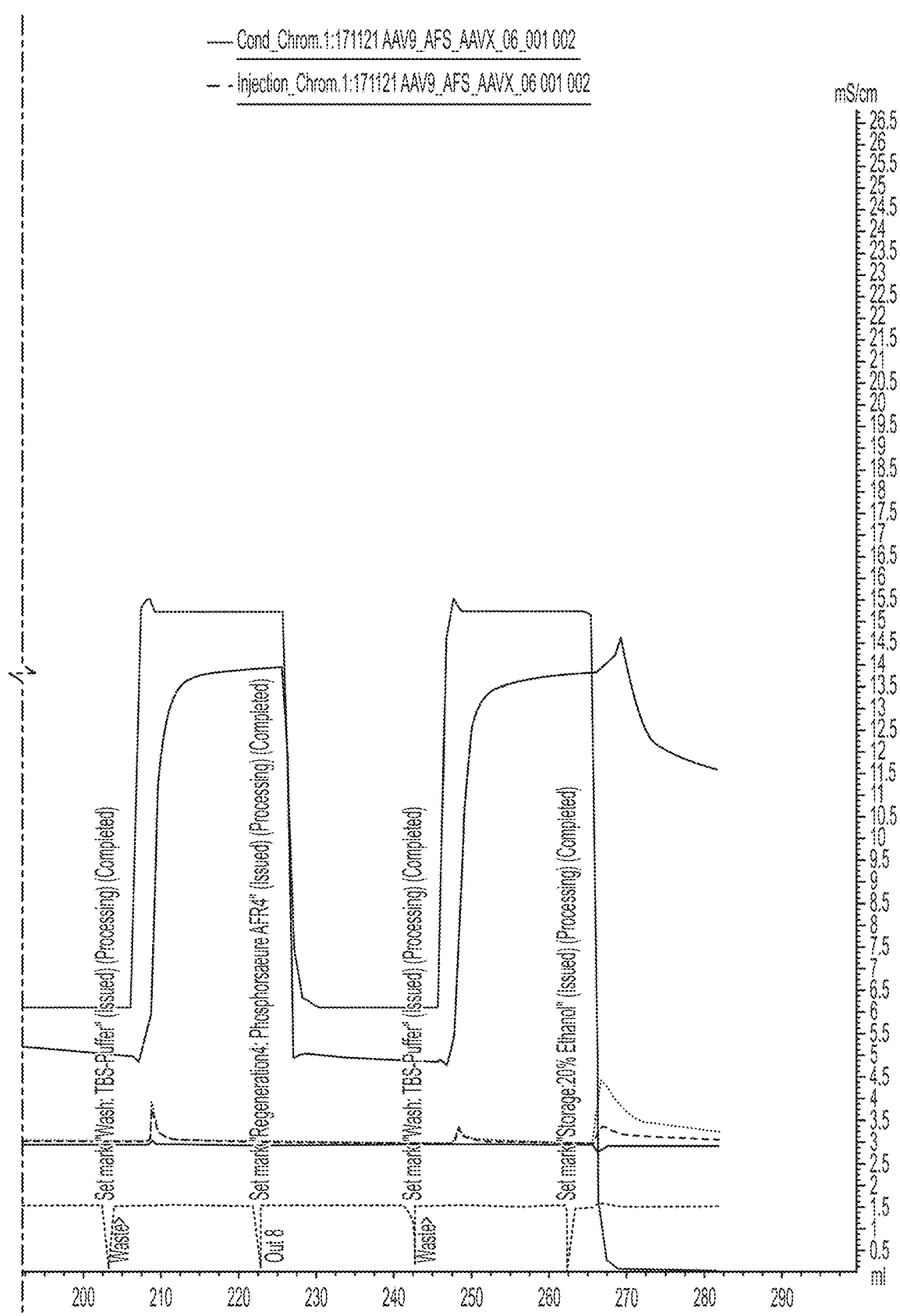

The samples taken were assayed by each of ITR qPCR, ELISA against AAV antigens and ELISA against HEK293 HP (as described in Examples 8 and 9 above) to assess yield and whether losses may have occurred in the steps. The chromatogram associated with the above example is shown in FIG. 16. The following Table 36 shows the samples taken at each of the above steps, with the yield of each component shown in Table 37.

TABLE 36

| Step | Buffer | Flowrate | CV | Fraction |
|---|---|---|---|---|
| Resin activation | — | 39 cm/h | 10 | Waste |
| Equilibration | 20 mM TrisHCl, 150 mM NaCl, pH 7.4 | | 10 | Waste |
| Sample application | 2x Flow through from TMAE | | X | FT/Wash1 |
| WASH 1 Re-equilibration | 20 mM TrisHCl, 150 mM NaCl, pH 7.4 | | 10 | FT/Wash1 |
| WASH 2 | 100 mM NaAcetate, 0.1% Polysorbate80, pH 6.0 | | 10 | Wash 2 |
| WASH 3 | 50 mM TrisHCl, 125 mM NaCl, pH 8.5 | | 10 | Wash 3 |
| WASH 4 | 50 mM TrisHCl, 50% (w/w) Ethylenglyocl, pH 8.5 | | 10 | Wash 4 |
| WASH 5 | 50 mM TrisHCl, 60% (w/w) Ethylene glycol + 750 mM NaCl pH 8.0 | | 10 | Wash 5 |
| WASH 6 | 20 mM TrisHCl, 150 mM NaCl, pH 7.4 | | 10 | Wash 6 |
| ELUTION 1 | 100 mM GlycineHCl, 200 mM NaCl, pH 2.5 | | 10 | Elution |
| WASH 7 | 20 mM TrisHCl, 150 mM NaCl, pH 7.4 | | | Wash 7 |
| STRIP | 50 mM Phosphoric acid pH 2.0 | | 10 | Strip 1 |
| WASH 8 | 20 mM TrisHCl, 150 mM NaCl, pH 7.4 | | 10 | Wash 8 |
| STRIP 2 | 50 mM Phosphoric acid pH 2.0 | | 10 | Strip 2 |

TABLE 37

| Step | Amount [ml] | ITR-qPCR E + 11 vg/ml | Total ITR-qPCR E + 11 vg | % ITR-qPCR |
|---|---|---|---|---|
| LOAD | 22.46 | 41.1 | 923.11 | 100.0% |
| Elution 1 | 19.97 | 53.10 | 1060.41 | 114.9% |

Samples above were also assayed by SDS-PAGE and 12% silver stain to detect total protein. The results of an SDS-PAGE assay are shown in FIG. 14 (see lanes 12-20).

Samples were then assayed by SDS-PAGE and a Western blot against AAV antigens. The primary antibodies are monoclonal antibodies against VP1, VP2 and VP3 of AAV while the secondary antibody is a goat anti-mouse coupled with alkaline phosphatase. The results of the Western blot assay are shown in FIG. 15 (see lanes 12-20).

Example 16

This example demonstrates elution conditions that are enhanced for AAV9, relative to use of acidic glycine or phosphoric acid.

AAV9 production was developed in a HEK293 cell line after transfection with a triple plasmid system containing encoding cDNA of the protein of interest and AAV9-. VP1. -VP2 and -VP3. From a 30 L Harvest aliquot the cells were disrupted by using a Megatron MT3000(Pall), followed by filtration of the AAV9 containing solution on a) depth filter PDP8 Area 0.5 m², b) depth filter V100 Area: 0.5 m² and c) Kleenpak Capsule 0.2 μm Area 0.15 m². The clarified cell free culture supernatant was concentrated and diafiltrated with Pall Omega T-Series Cassette 300 kDa. The viral particles were loaded onto a membrane adsorber (MustangQ. Pall Part Number XT140MSTGQP05) at nonbinding conditions for AAV9. The load was applied onto a column containing POROS™ CaptureSelect™ AAVX Affinity Matrix (Thermo Fisher, Catalog No. A36739, Thermo Fisher) ID 16 mm, Bed height 50 mm, volume 10.0 ml followed by buffer steps with column volumes as indicated.

Samples from the various wash and elution steps were taken at various points to assay how much AAV9 is present in the sample. The assays indicate how much AAV9 was lost in various wash steps. The following test procedure was undertaken. First, the column was equilibrated with at least five column volumes of 50 mM TrisHCl, 125 mM NaCl at pH 8.5. The load was applied onto the column containing affinity resin. A portion of the sample loaded onto the column was saved and later assayed by ITR qPCR, ELISA against AAV antigens, and ELISA against HEK293 HCP antigens. The column was then re-equilibrated (Wash 1, W1) with 5 column volumes of 50 mM TrisHCl, 125 mM NaCl at pH 8.5. A sample of the flow through was saved and later assayed by ITR qPCR, ELISA against AAV antigens, and ELISA against HEK293 HCP antigens.

The column was then washed with 5 column volumes of Wash 2 (W2): 100 mM NaAcetate, 0.1% Polysorbate80 at pH 6.0. The column was then washed with 10 column volumes of Wash 3 (W3): 50 mM TrisHCl, 125 mM NaCl at pH 8.5. A sample from eluate of each of W2 and W3 was taken and assayed according to ITR qPCR, ELISA against AAV antigens, and ELISA against HEK293 HCP antigens.

Elution was undertaken by first applying 20 column volumes of purified water, then 20 column volumes of 1 mM HCl at pH 3.2, and then 20 column volumes of 50 mM TrisHCl, 750 mM NaCl, 50% DMSO (w/w) at pH 8.0. The column was washed with 20 column volumes of purified water followed by 10 column volumes of 33 mM HCl at pH 2.0.

The above test procedure is described in more detail in Table 38. A linear flow rate of 39 cm/h was applied in all steps.

TABLE 38

| STEP | |
|---|---|
| Equilibration | 50 mM TrisHCl |
|  | 125 mM NaCl |
|  | pH 8.5 |
| LOAD | AAV9 PPHT2_1813MUQ_FT, pH 8.5 |
| Wash 1 | 50 mM Tris HCl |
| (Re-equilibration) | 125 mM NaCl |
|  | pH 8.5 |
| Wash 2 | 100 mM Sodium Acetate |
|  | 0.1% Polysorbate 80 |
|  | pH 6.0 |
| Wash 3 | 50 mM Tris HCl |
|  | 125 mM NaCl |
|  | pH 8.5 |
| ELUTION 1 | Purified Water |
| ELUTION 2 | 1 mM HCl, pH 3.2 |
| ELUTION 3 | 50 mM Tris HCl |
|  | 750 mM NaCl |
|  | 50% DMSO (w/w) |
|  | pH 8.0 |
| Wash 4 | Purified Water |
| ELUTION 4 | 33 mM HCl, pH 2.0 |

Figure 17:
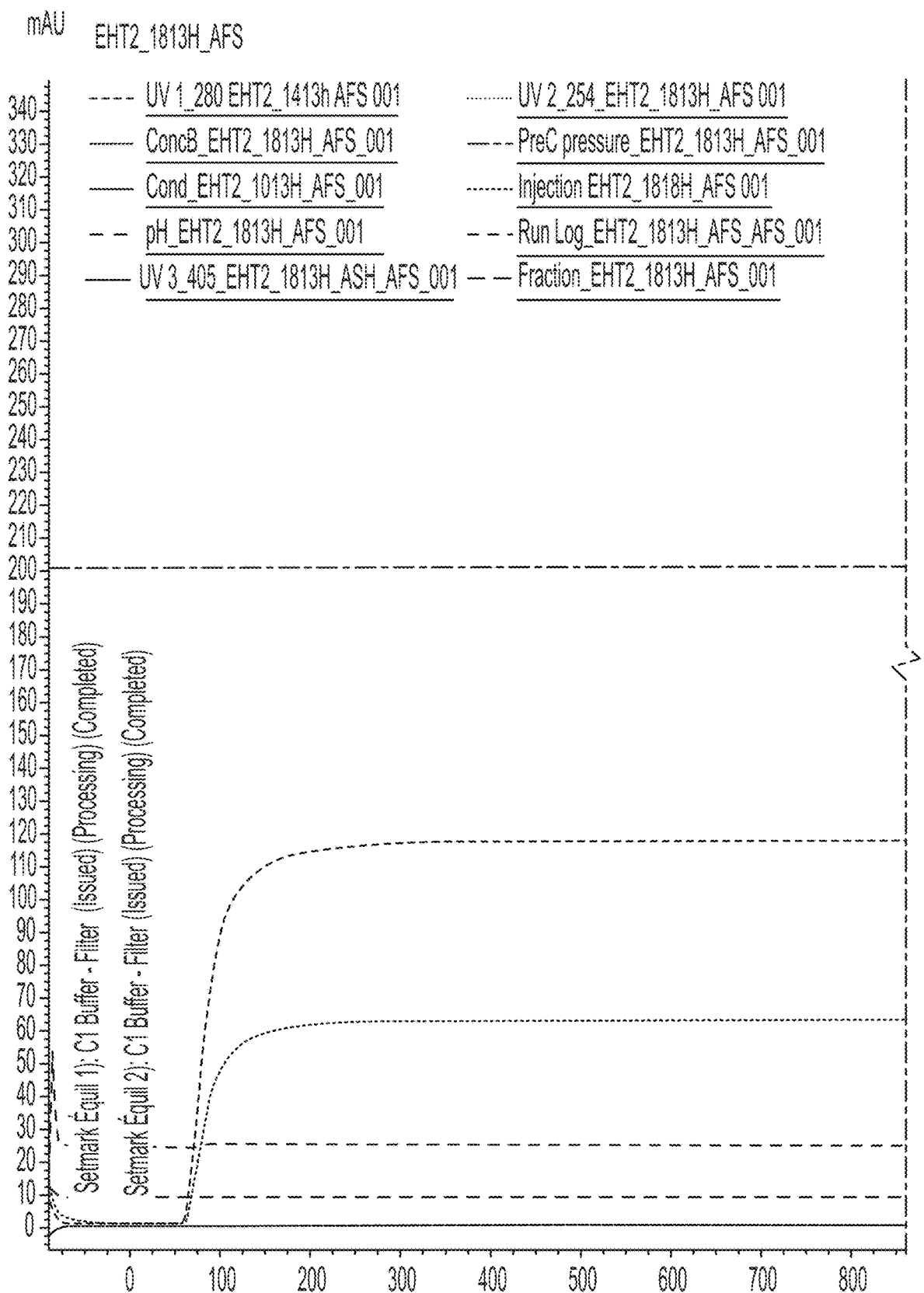
FIG. 17 depicts the chromatogram of the separation procedure according to Example 16.
Figure 17:
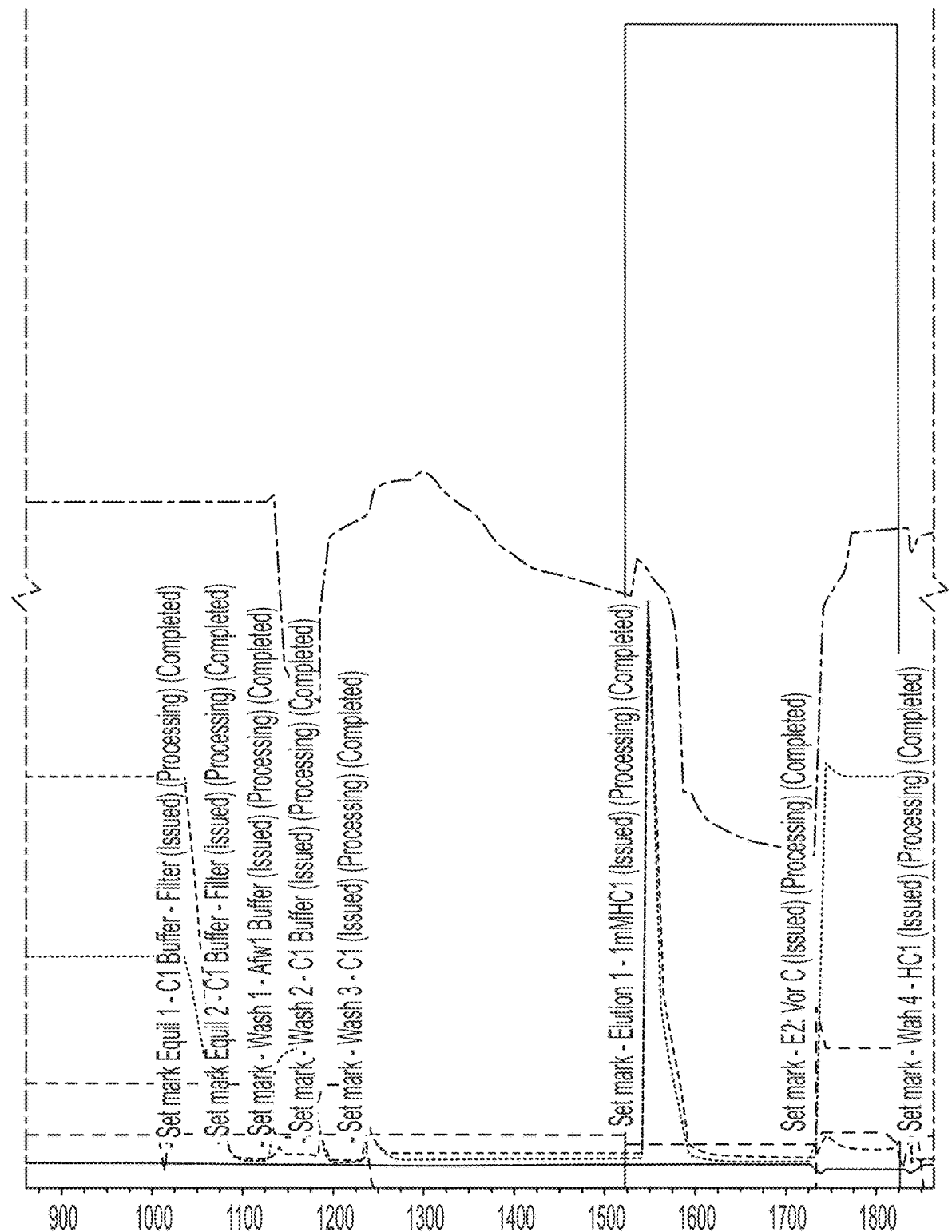
Figure 17:
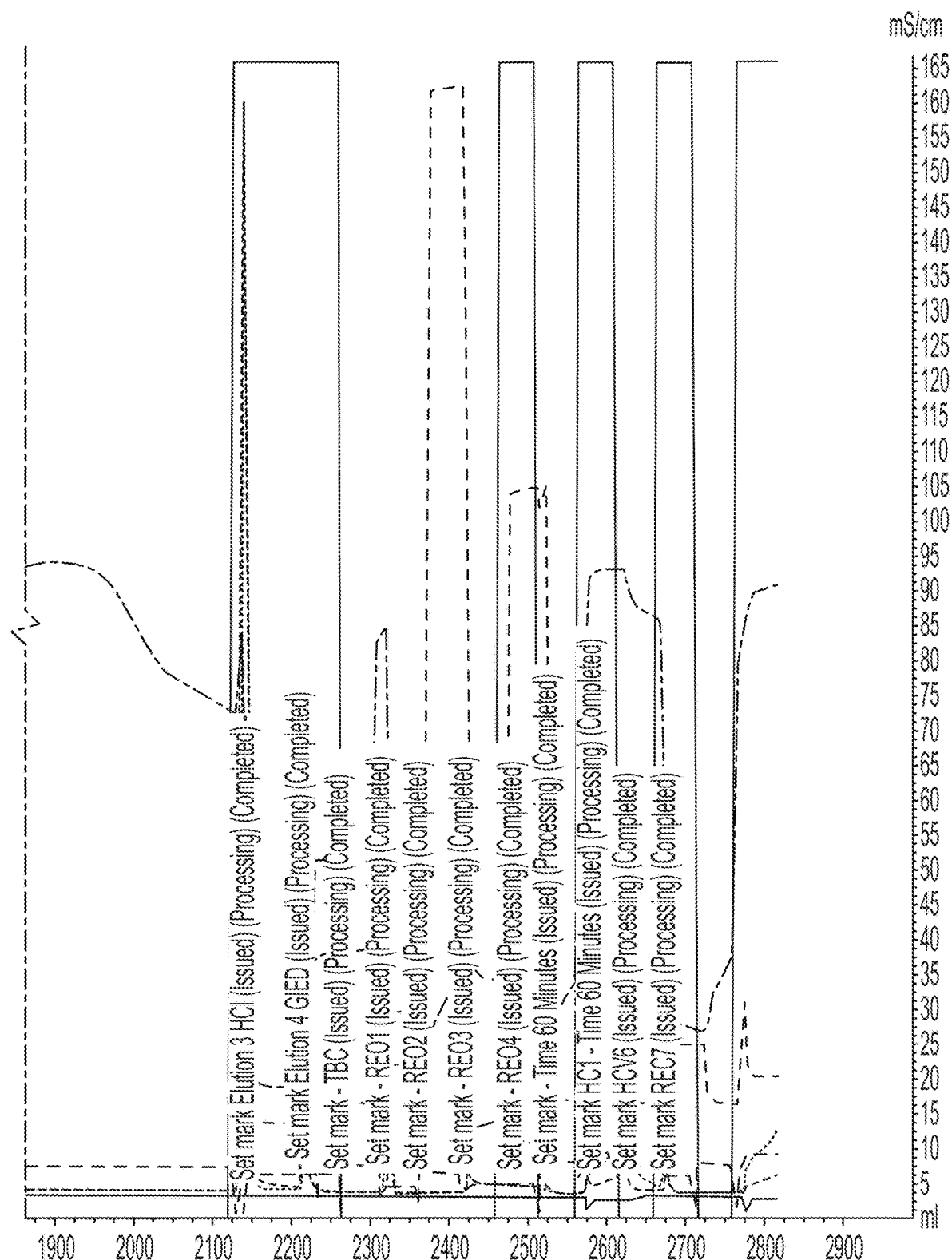

The samples taken were assayed by each of ITR qPCR and ELISA (as described in Example 8 above) against AAV antigens and ELISA against HEK293 HCP to assess yield and whether losses may have occurred in the steps. The chromatogram associated with the above example is shown in FIG. 17. The following Table 39 shows the samples taken at each of the above steps, with the yield of certain components shown in Table 40.

TABLE 39

| Step | Buffer | Flowrate | CV | Fraction |
|---|---|---|---|---|
| Equilibration | 50 mM Tris HCl, 125 mM NaCl, pH 8.5 | 39 cm/h | 5 | Waste |
| Sample application | AAV9 PPHT2_1813MUQ_FT, pH 8.5 | | X | FT/Wash 1 |
| WASH 1 Re-equilibration | 50 mM Tris HCl, 125 mM NaCl, pH 8.5 | | 5 | FT/Wash 1 |
| WASH 2 | 100 mM NaAcetate, 0,1% Polysorbate80, pH 6.0 | | 5 | Wash 2 |
| WASH 3 | 50 mM TrisHCl, 125 mM NaCl, pH 8.5 | | 5 | Wash 3 |
| Elution 1 | Purified water | | 20 | Wash 5 |
| Elution 2 | 1 mM Hydrochloric acid, pH 3.2 | | 20 | Wash 6 |
| Elution 3 | 50 mM TrisHCl, 750 mM NaCl, 50% DMSO (w/w), pH 8.0 | | 10 | Elution |
| Wash | Purified water | | 20 | Wash 7 |
| Elution 4 | 33 mM Hydrochloric acid, pH 2.0 | | 10 | Strip 1 |
| Other steps | Regeneration procedure | | x | X |

TABLE 40

| Step | Amount [ml] | AAV9 Antigen cp/ml [10 + 11] | Total AAV9:AG Cp [10 + 11] | % |
|---|---|---|---|---|
| LOAD | 1011.85 | 7.44 | 7528.16 | 100.0 |
| Elution 2 1 mM HCl | 40.06 | 117.0 | 4687.02 | 62.3 |
| Elution 3 DMSO | 6.19 | 61 | 377.6 | 5.0 |
| STRIP 33 mM HCl | 9.31 | 54.5 | 507.4 | 6.7 |

Figure 18:
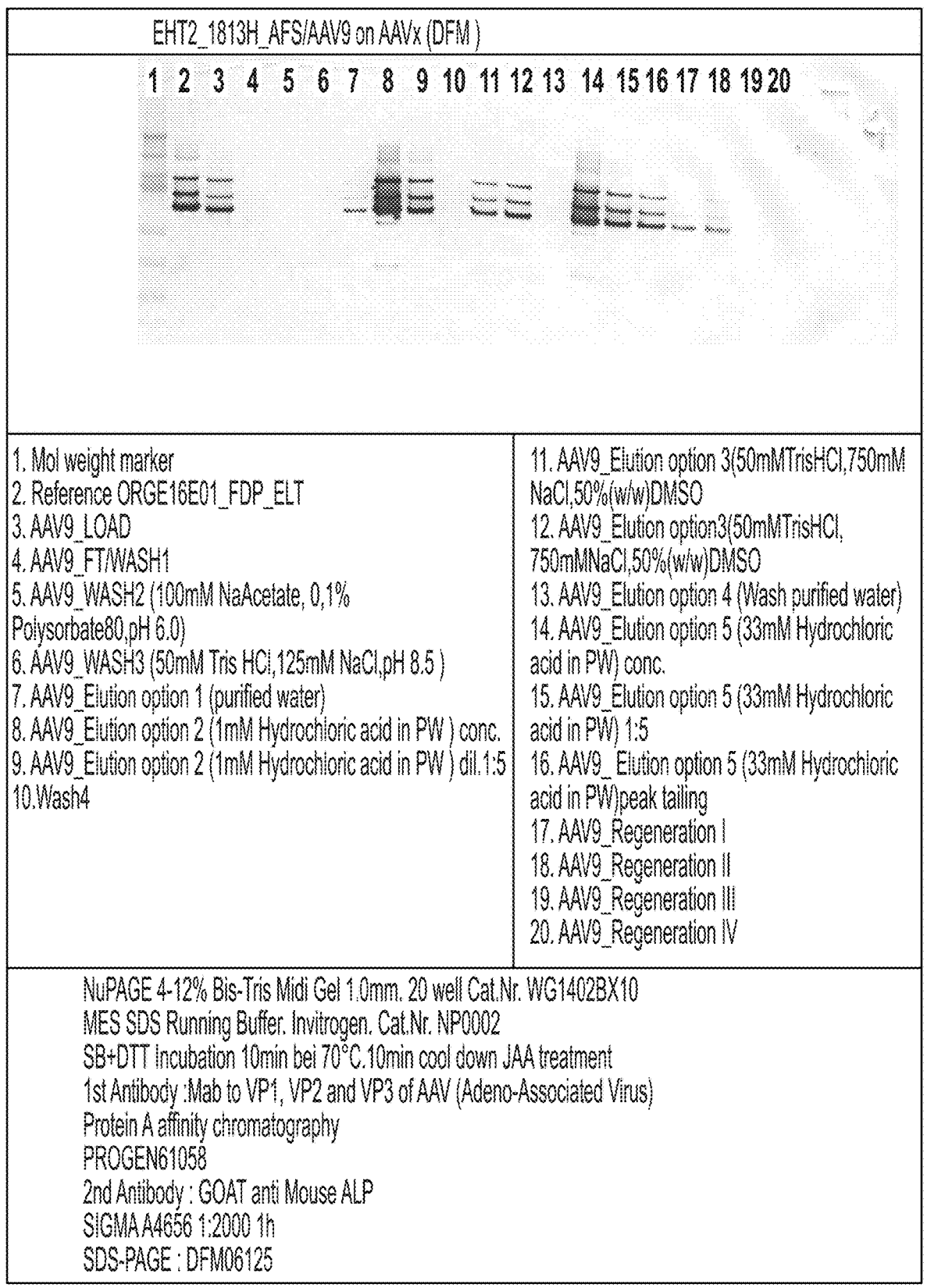
FIG. 18 depicts a Western Blot against AAV antigens from the various fractions taken from wash steps and eluates as described in Example 16.

Samples above were also assayed by SDS-PAGE and Western Blotting, with the results shown in FIG. 18.

AAV9 can be eluted from Capture select AAVx with 1 mM Hydrochloric acid which has the benefit of introducing only very low amount of free acid into the aqueous system. A further elution procedure near neutral pH can be carried out with a DMSO containing aqueous buffer solution (750 mM NaCl, 50 mM TrisHCl, 50% w/w Dimethylsulfoxide). DMSO may be beneficial if the DMSO-containing eluate is applied to a ultracentrifugation using a sucrose gradient. Both elution strategies potentially have improved properties to maintain the biopotency during elution from AAVX resin for all AAV subtypes compared to harsh elution conditions a 100 mM at pH below 3 and/or high amounts of sodium or magnesium chloride.

Example 17

This example demonstrates elution conditions that are enhanced for AAV9, relative to use of acidic glycine or phosphoric acid.

AAV9 production was developed in a HEK293 cell line after transfection with a triple plasmid system containing encoding cDNA of the protein of interest (FIX-padua, double stranded) and AAV9-. VP1. -VP2 and -VP3. From a 30 L Harvest aliquot the cells were disrupted by using a Megatron MT3000(Pall), followed by filtration of the AAV9 containing solution on a) depth filter PDP8 Area 0.5 m² b) depth filter V100 Area: 0.5 m² and c) Kleenpak Capsule 0.2 μm Area 0.15 m². The clarified cell free culture supernatant was concentrated and diafiltrated with Pall Omega T-Series Cassette 300 kDa. The viral particles were loaded onto a membrane adsorber (MustangQ. Pall Part Number XT140MSTGQP05) at nonbinding conditions for AAV9. The load was applied onto a column containing POROS™ CaptureSelect™ AAVX affinity matrix (Thermo Fisher, Catalog No. A36739; 10 mm, Bed height 28 mm, volume 2.2 ml).

Samples from the various wash and elution steps were taken at various points to assay how much AAV9 is present in the sample. The assays indicate how much AAV9 was lost in various wash steps. The following test procedure was undertaken. First, a column containing affinity resin ID 10 mm, with a bed height of 28 mm and a volume 2.2 ml, was equilibrated with at least ten column volumes of 50 mM TrisHCl, 125 mM NaCl at pH 8.5. The load was applied onto the column containing affinity resin. A portion of the sample loaded onto the column was saved and later assayed by ITR qPCR, ELISA against AAV antigens, and ELISA against HEK293 HCP antigens. The column was then re-equilibrated (Wash 1, W1) with 10 column volumes of 50 mM TrisHCl and 125 mM NaCl at pH 8.5. A sample of the flow through was saved and later assayed by ITR qPCR, ELISA against AAV antigens, and ELISA against HEK293 HCP antigens.

The column was then washed with 10 column volumes of Wash 2 (W2): 100 mM NaAcetate and 0.1% Polysorbate80 at pH 6.0. The column was then washed with 10 column volumes of Wash 3 (W3): 50 mM TrisHCl and 125 mM NaCl at pH 8.5. The column was then washed with 30 column volumes of purified water (Wash 4 (W4)). A sample from eluate of each of W2, W3 and W4 was taken and assayed according to ITR qPCR, ELISA against AAV antigens, and ELISA against HEK293 HCP antigens.

Elution was undertaken by first applying 20 column volumes of a gradient of 0 to 100% 33 mM Hydrochloric acid/1000 mMNaCl in 1 mM Hydrochloric acid.

The above test procedure is described in more detail in Table 41. A linear flow rate of 39 cm/h was applied in all steps.

TABLE 41

| STEP | |
|---|---|
| Equilibration | 50 mM TrisHCl<br>125 mM NaCl<br>pH 8.5 |
| LOAD | AAV9 EHT2_1831_MUQ_FT |
| Wash 1 (Re-equilibration) | 50 mM Tris HCl<br>125 mM NaCl<br>pH 8.5 |
| Wash 2 | 100 mM NaAcetate<br>0.1% Polysorbate80<br>pH 6.0 |
| Wash 3 | 50 mM TrisHCl<br>125 mM NaCl<br>pH 8.5 |
| Wash 4 | Purified Water |
| ELUTION | Gradient of 0 to 100% 33 mM Hydrochloric acid/<br>1000 mM NaCl in 1 mM Hydrochloric acid |
| Regeneration | |

Figure 19:
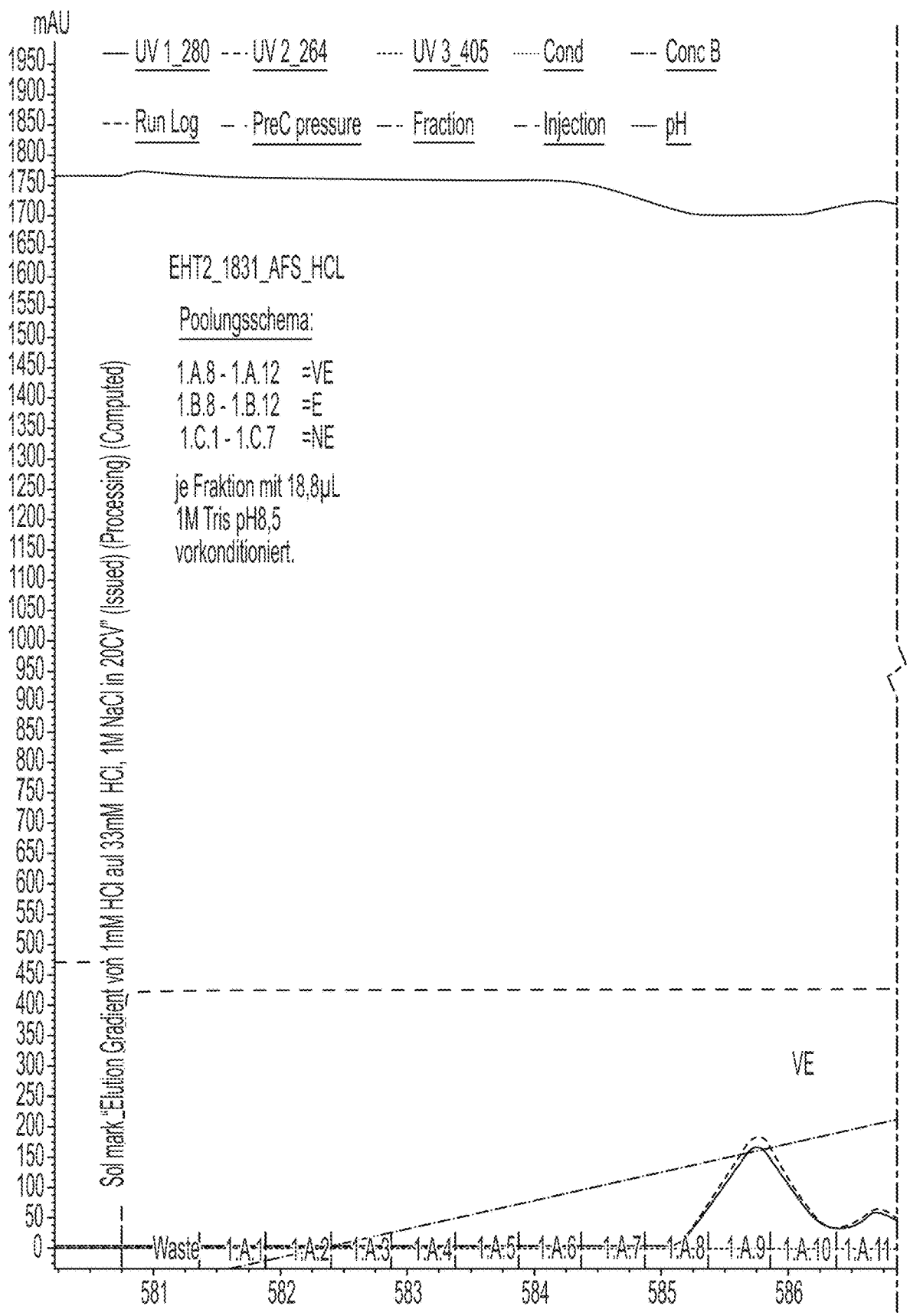
FIG. 19 depicts the chromatogram of the separation procedure according to Example 17.
Figure 19:
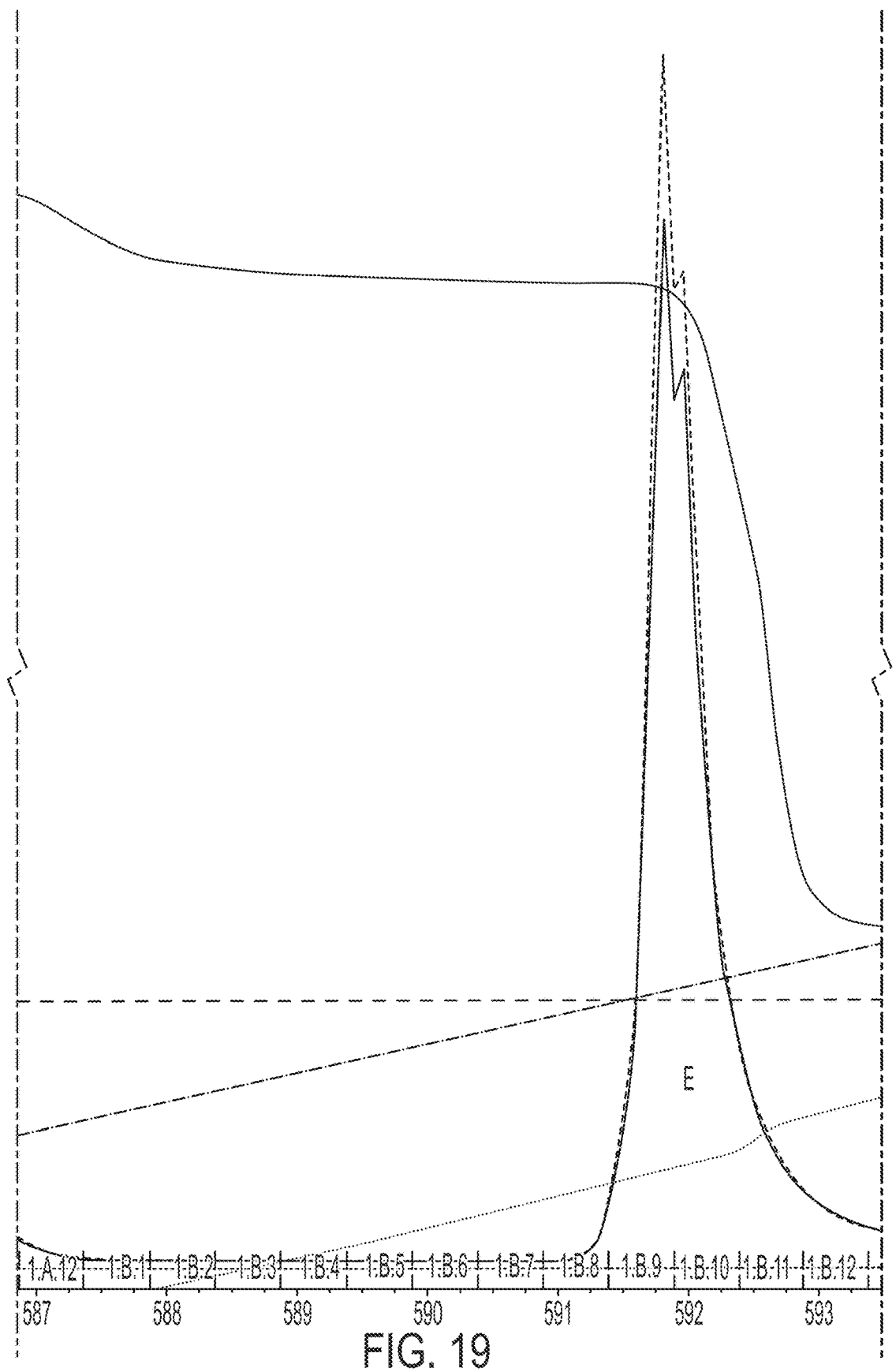
Figure 19:
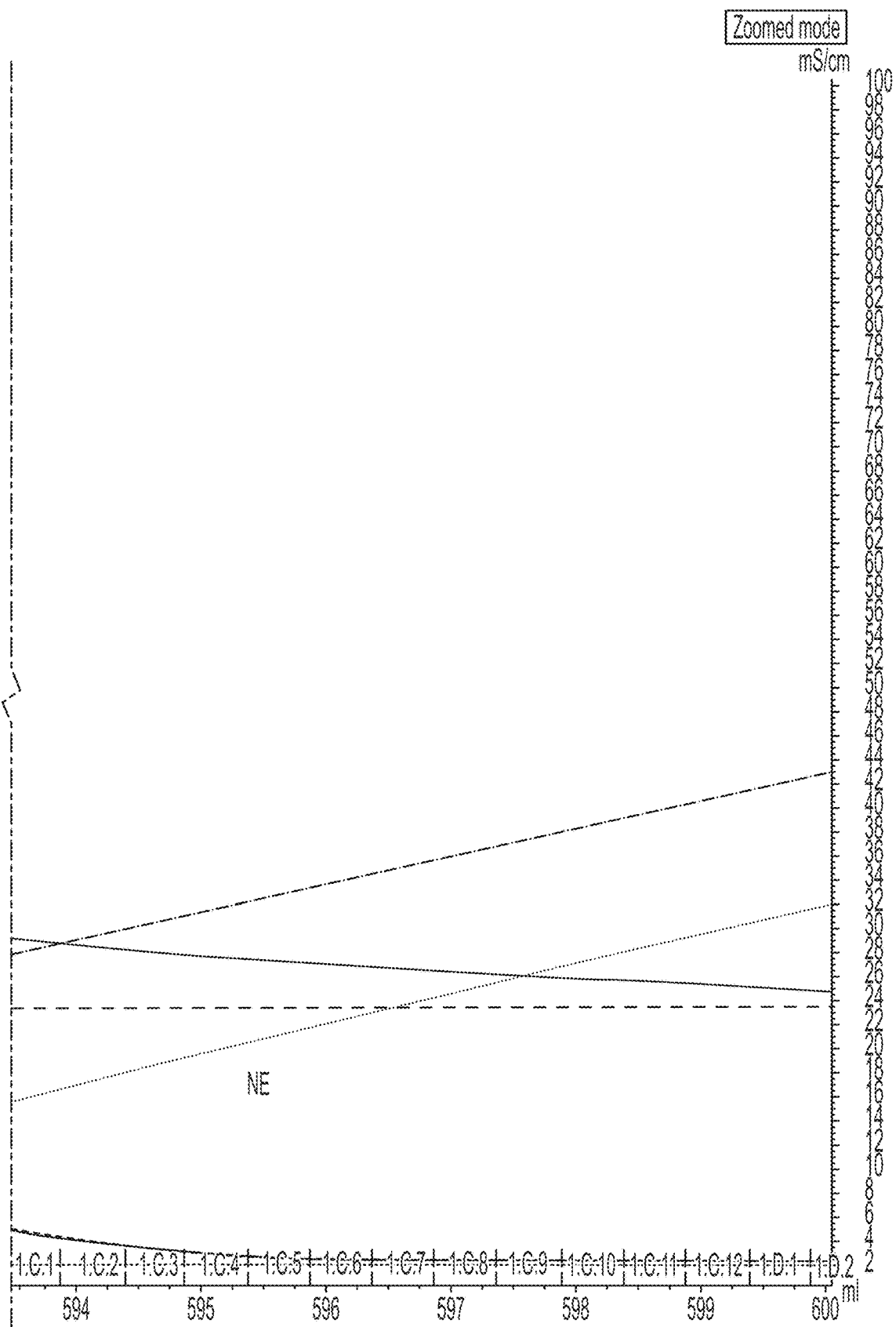
Figure 20:
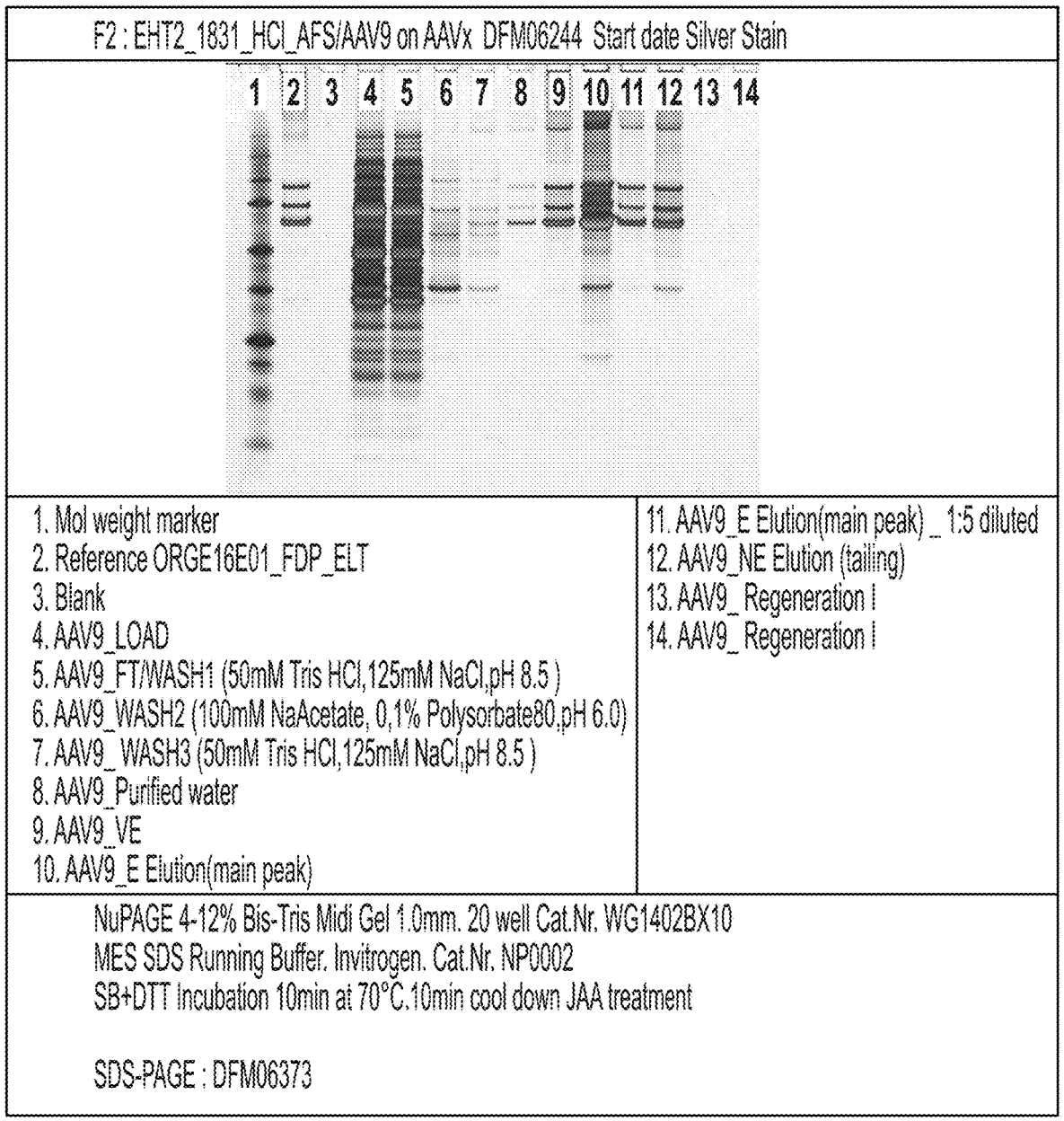
FIG. 20 depicts an SDS-PAGE silver stain gel showing the proteins present in various fractions taken from wash steps and eluates as described in Example 17.

The samples taken were assayed by each of ITR qPCR and ELISA (as described in Example 8 above) against AAV antigens and ELISA against HEK293 HCP to assess yield and whether losses may have occurred in the steps. The chromatogram associated with the above example is shown in FIG. 19. The silver stain is shown in FIG. 20.

The biopotency of the eluted AAV9 was 0.51 BPU.

Example 18

The elution properties of various resin types were assessed with regards to different elution buffers. A polyol elution buffer was prepared that comprises 50% Ethylene glycol (w/w), 50 mM TrisHCl, 750-2000 mM NaCl, pH 8.0. An acidic elution buffer was prepared that comprises 100 mM Glycine pH 2.5, 100 mM Na-Citrate pH 3.0, and 50 mM Phosphoric acid pH 2.0. An MgCl₂-containing elution buffer was prepared that comprises 2M MgCl₂ and 50 mM TrisHCl, at pH 7.4.

Several resins were tested. The results are shown in Table 42 below. In the table "Yes" indicates that AAV8 can be eluted from the resin with a potential "elution buffer" with an amount of greater than 10% of the load, while "No" indicates that AAV can be eluted from the resin with a "potential elution" buffer at an amount of less than 1% of the load.

TABLE 42

| Resin type | Polyol buffer | Acidic buffer | MgCl2 |
|---|---|---|---|
| Capture Select AAV8 [1] | Yes | Yes | Not tested |
| Capture Select AAV9 [1] | No | Yes | Yes |
| Capture SelectAAVX [1] | No | Yes | Yes |
| ADK8-Sepharose [2] | Yes | Yes | Not tested |
| AVB Sepharose [3] | Not tested | Yes | Not tested |

[1] Thermo Fisher Scientific
[2] The resin was prepared by immobilizing a monoclonal antibody type ADK8 from Progen AG onto a CNBr-SepharoseFastFlow affinity resin at a density of 0.94 mg/ml resin.
[3] GE Healthcare Various buffers were tested for their ability to elute AAV8 from the above Capture Select AAV8 resin. The results are shown in Table 43 below.

TABLE 43

| Resin type AAV8 | DMSO Organic solvent 50 mM Tris HCl 750 mM NaCl 50% (w/w) DMSO pH 8.0 | Carbohydrate Sucrose, Mannose, Sorbitol (Polyol) 50 mM Arginine Arginine-HCl, 55% (w/w) Sucrose, 2 mM MgCl2, 800 mM NaCl, pH 8.0 or 20% (w/w) Sucrose 10% (w/w) Sorbitol 5% (w/w) Mannitol (Sucrose) 15% (w/w) Glycerol 50 mM Histidine 800 mM NaCl pH 8.0 | Glycerol (Polyol) 50 mM Arginine Arginine-HCl, 50% (w/w) Glycerol 800 mM NaCl, pH 8.0 | Ethylen glycol (Polyol) 50 mM Taurine 60% (w/w) Ethylene glycol 750 mM NaCl 0.1% Octylglyco-pyranoside pH 8.0 or 50 mM Tris HCl 55% (w/w) Ethylene glycol 750 mM NaCl pH 8.0 or 50 mM TrisHCl, 1 M Ammonsulfate, 50% Ethylene glycol pH 7.0 |
|---|---|---|---|---|
| Polyol/organic solvent content | ≥50% | ≥50% | ≥50% | ≥50% |
| Elution of AAV8 | No | Yes | Yes | Yes |

Elution buffers listed in Table 44 were also tested to determine whether they were satisfactory for eluting AAV from Capture Select® AAV9 available from Thermo Fisher Scientific.

TABLE 44

| Buffer | pH | Composition |
|---|---|---|
| Glycine, alkaline | pH 8.0 ± 0.2 | 20 mM Glycine |
| 2 M NaCl/TrisHCl | pH 7.4 ± 0.2 | 50 mM Tris, 2 M NaCl |
| Sodium citrate | pH 3.0 ± 0.2 | 100 mM Sodium Citrate |
| Magnesium chloride/TrisHCl | pH 7.4 ± 0.2 | 50 mM Tris, 2 M MgCl2 |
| Regeneration buffer NaP/EG | pH 2.5 ± 0.2 | 50 mM Sodium Phosphate, 50% Ethylene glycol |

TABLE 44-continued

| Buffer | pH | Composition |
|---|---|---|
| Regeneration buffer Arginine/EDTA/Urea | pH 8.5 ± 0.2 | 20 mM Arginine, 2 mM EDTA. 4 M Urea |

Figure 21:
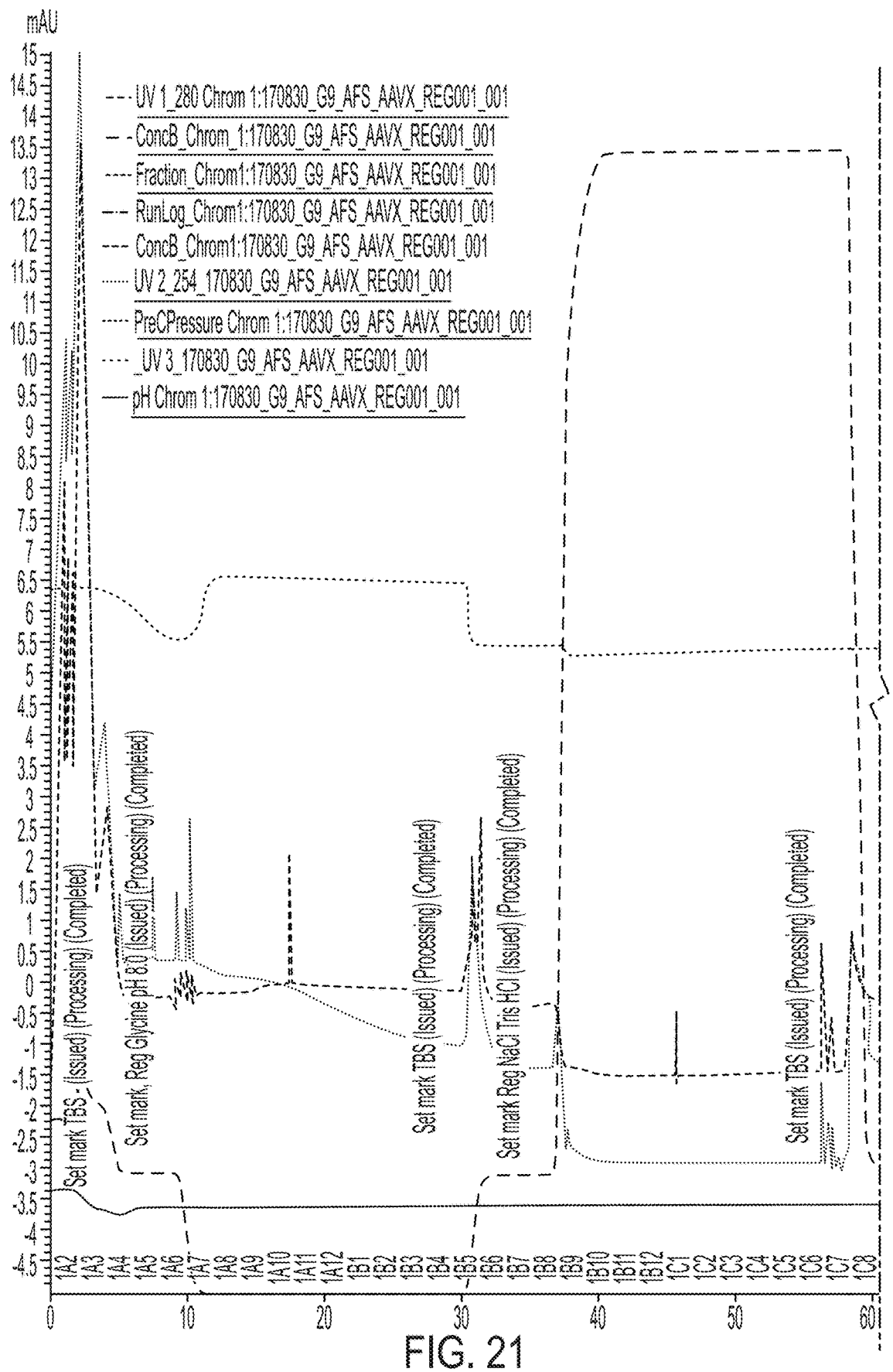
FIG. 21 depicts the chromatogram showing results from an elution screen described in Example 18.
Figure 21:
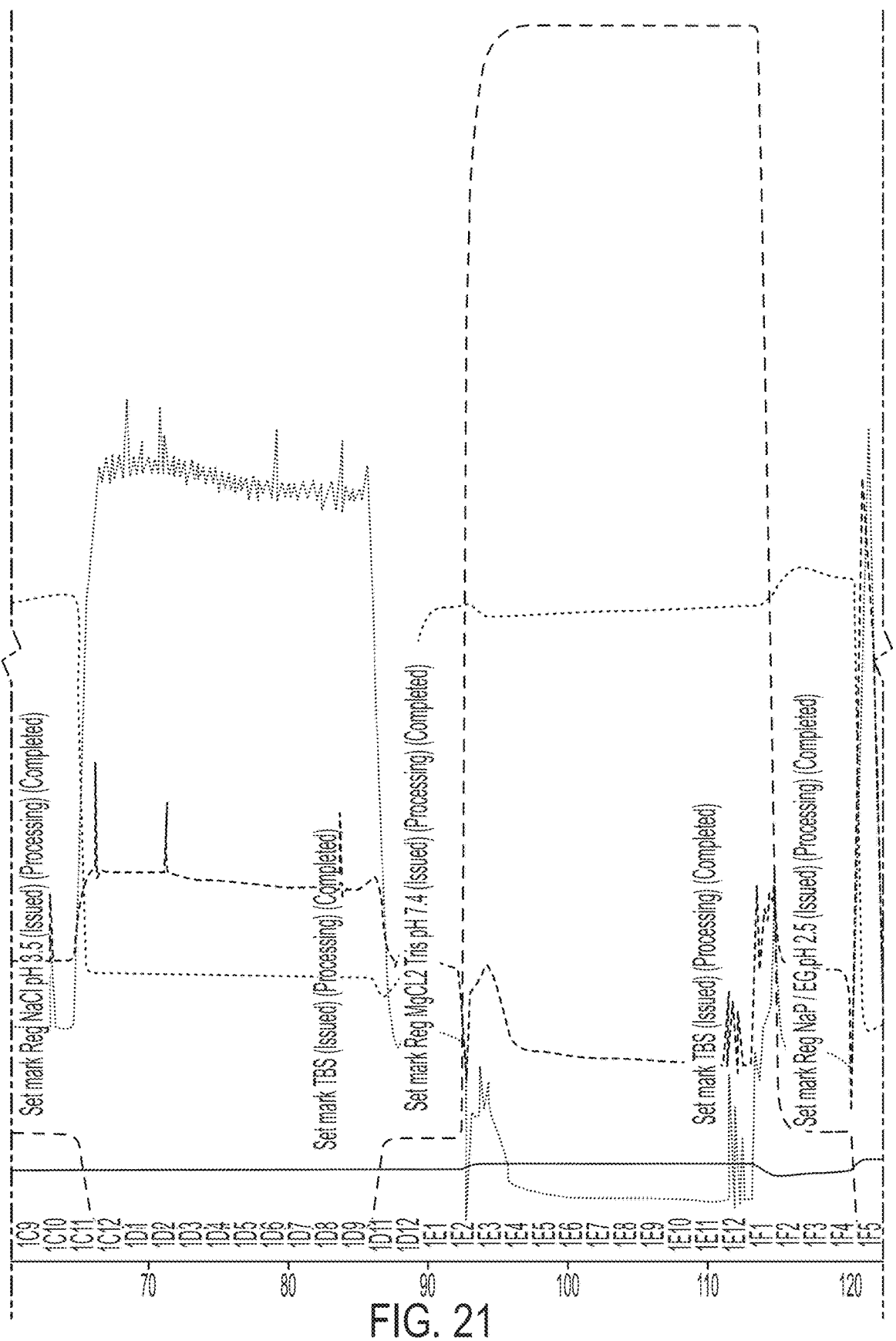
Figure 21:
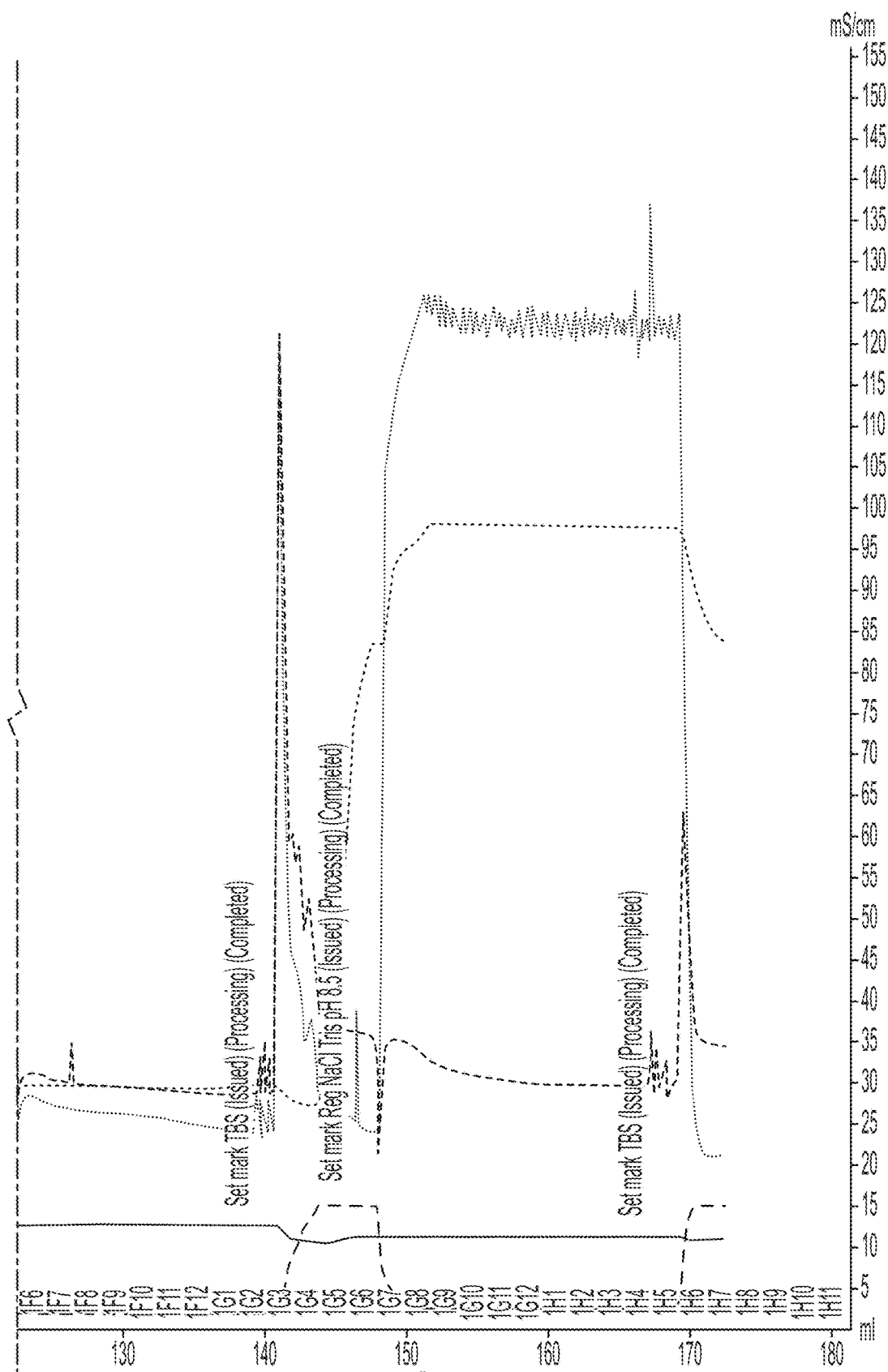

Each of the potential elution buffers as described in Table 44 were applied in succession as part of an elution screen to determine which elution buffers could be used on Capture select AAVx. The screen started with the elution buffer with the potentially lowest elution strength and ends with the buffer with the potentially highest elution strength. The chromatogram is shown in FIG. 21. This is an example which elution options can be applied on Capture select AAVx.

All references, including publications, patent applications, and patents, cited herein are hereby incorporated by reference to the same extent as if each reference were individually and specifically indicated to be incorporated by reference and were set forth in its entirety herein.

What is claimed is:

1. A method of purifying an adeno-associated virus (AAV) comprising
   (a) loading an AAV containing solution onto an affinity resin targeted against AAV under conditions that allow binding between the AAV in the solution and the affinity resin;
   (b) undertaking at least two wash steps; and
   (c) eluting the AAV from the affinity resin;
   wherein at least one of the wash steps comprises applying to the affinity resin a buffer comprising an organic solvent or detergent.

2. The method of claim 1, further comprising contacting the AAV containing solution with an anion exchanger and eluting the AAV containing solution from the anion exchanger prior to loading the AAV containing solution onto the affinity resin.

3. The method of claim 1, wherein at least one of the buffers comprises (a) TrisHCl and a salt; (b) sodium acetate; (c) TrisHCl and ethylene glycol; (d) Arginine-HCl and one of sucrose and glycerol; (e) Taurine and ethylene glycol; (f) Arginine-HCl, Lysine-HCl, and Histidine-HCl; (g) TrisHCl and DMSO; or (h) combinations thereof.

4. The method of claim 1 wherein the organic solvent or detergent is polysorbate 80, ethylene glycol, sorbitol, mannitol, xylitol, DMSO, sucrose, trehalose, 2-[4-(2,4,4-trimethylpentan-2-yl)phenoxy]ethanol, tri (n-butyl) phosphate (TNBP), or combinations thereof.

5. The method of claim 1, wherein the first wash step comprises applying to the affinity resin a first buffer comprising from about 50 to about 2000 mM sodium acetate and from about 0.05 to about 0.2% polysorbate 80, and wherein the first buffer has a pH from about 5.2 to about 6.8; and
   wherein the second wash step comprises applying to the affinity resin a second buffer comprising from about 30 to about 200 mM TrisHCl and from about 75 to about 500 mM salt, and wherein the second buffer has a pH from about 7.5 to about 9.2.

6. The method of claim 1, wherein the first wash step comprises applying to the affinity resin a first buffer comprising from about 50 to about 500 mM sodium salt of 2-(N-morpholino)ethanesulfonic acid (MES-Na), from about 3 to about 30 mM EDTA, and a solvent/detergent mixture comprising polysorbate 80, DMSO and tri(n-butyl) phosphate (TNBP), and wherein the first buffer has a pH from about 5.2 to about 6.8;
  wherein the second wash step comprises applying to the affinity resin a second buffer comprising from about 30 to about 200 mM TrisHCl or Arginine-HCl and from about 75 to about 500 mM salt, and wherein the second buffer has a pH from about 7.5 to about 9.2; and
  wherein the third wash step comprises applying to the affinity resin a third buffer comprising from about 20 to about 80 mM Arginine-HCl and from about 50 to about 200 mM salt, and wherein the third buffer has a pH from about 7.3 to about 8.8.

7. The method of claim 1, wherein the first wash step comprises applying to the affinity resin a first buffer comprising from about 50 to about 200 mM taurine, and 0.2 to 1.5% PEG wherein the first buffer has a pH from about 5.2 to about 6.8;
  wherein the second wash step comprises applying to the affinity resin a second buffer comprising from about 30 to about 300 mM glycine, and wherein the second buffer has a pH from about 7.5 to about 9.2; and
  wherein the third wash step comprises applying to the affinity resin a third buffer comprising from about 20 to about 150 mM taurine, from about 30 to about 75 vol % ethylene glycol, and from 0.05 to 0.2% octylglycopyranoside, and wherein the third buffer has a pH from about 7.3 to about 8.8.

8. The method of claim 1 wherein the first wash step comprises applying to the affinity resin a first buffer comprising from about 80 to about 400 mM Bis-Tris, and about 10 to about 20 grams of a solvent/detergent mixture comprising about 2-[4-(2,4,4-trimethylpentan-2-yl)phenoxy] ethanol, polysorbate 80 and TNBP in a ratio of about 11:3:3 (by weight) wherein the first buffer has a pH from about 5.2 to about 6.8;
  wherein the second wash step comprises applying to the affinity resin a second buffer comprising from about 5 to about 20 mmol sodium citrate, and wherein the second buffer has a pH from about 7.5 to about 9.2; and
  wherein the third wash step comprises applying to the affinity resin a third buffer comprising from about 50 to about 200 mM Arginine-HCl, from about 50 to about 200 mM Lysine HCl, from about 50 to about 200 mM Histidine-HCl, and from about 1 mM to about 4 mM N-acetyl-D,L-tryptophan, and about 10% to about 40% (w/w) polysorbate 80, and wherein the third buffer has a pH from about 7.3 to about 8.8.

9. The method of claim 1, wherein the first wash step comprises applying to the affinity resin a first buffer comprising from about 50 nM to about 200 mM NaAcetate and from about 0.05 to about 0.2% Polysorbate 80, wherein the first buffer has a pH of about 5.2 to about 6.8;
  wherein the second wash step comprises applying to the affinity resin a second buffer comprising from about 20 nM to about 100 mM TrisHCl and from about 50 nM to about 200 nM of salt, wherein the second buffer has a pH of about 7.5 to about 8.8; and
  wherein the third wash step comprises applying to the affinity resin a third buffer comprising about 20 mM to 100 mM TrisHCl, from about 40% to about 60% (w/w) ethylene glycol, and wherein the third buffer has a pH from about 7.5 to about 8.8.

10. The method of claim 5, wherein the salt is selected from NaCl, KCl, $MgCl_2$, $CaCl_2$), Sodium Citrate, LiCl, CsCl, Sodium Acetate, and a combination of one or more of NaCl, KCl, $MgCl_2$, $CaCl_2$), Sodium Citrate, LiCl, CsCl, and Sodium Acetate.

11. The method of claim 5, further comprising prior to the first wash step applying to the affinity resin a fourth buffer comprising from about 10 to about 30 mM TrisHCl and from about 75 to about 250 mM NaCl, and wherein the fourth buffer has a pH from about 6.5 to about 8.0.

12. The method of claim 5, wherein the first buffer comprises about 100 mM sodium acetate, about 0.1% polysorbate 80, and wherein the first buffer has a pH of about 6.0.

13. The method of claim 5, wherein the second buffer comprises about 50 mM TrisHCl and about 125 mM NaCl, and wherein the second buffer has a pH of about 8.5.

14. The method of claim 5, wherein a third buffer comprises about 50 mM TrisHCl and about 50 vol % ethylene glycol, and wherein the third buffer has a pH of about 8.5.

15. The method of claim 1, wherein the first wash step comprises applying to the affinity resin a first buffer comprising from about 50 to about 200 mM sodium acetate and from about 0.05 to about 0.2% polysorbate 80, and wherein the first buffer has a pH from about 5.5 to about 6.5;
  wherein the second wash step comprises applying to the affinity resin a second buffer comprising from about 10 to about 70 mM TrisHCl and from about 75 to about 250 mM NaCl, and wherein the second buffer has a pH from about 8.0 to about 9.0; and
  wherein the third wash step comprises applying to the affinity resin a third buffer comprising from about 10 to about 70 mM TrisHCl and from about 30 to about 75 vol % ethylene glycol, and wherein the third buffer has a pH from about 8.0 to about 9.0.

16. The method of claim 1, wherein eluting comprises contacting the affinity resin with an elution buffer comprising ethylene glycol, a salt, and a buffer such as TrisHCl, wherein the pH is at least 7.0.

17. The method of claim 16, wherein the salt concentration is about 750 mM, the buffer concentration is about 50 mM, and the ethylene glycol is 50-60% (w/w).

18. The method of claim 1 wherein eluting comprises contacting the affinity resin with an elution buffer comprising about 2 mM magnesium chloride, about 50 mM Arginine-HCl, about 750 mM to about 1000 mM NaCl and at least about 55% (w/w) sucrose at a pH of at least about 8.0.

19. The method of claim 1, wherein eluting comprises contacting the affinity resin with an elution buffer comprising about 2 mM magnesium chloride, about 50 mM Arginine-HCl, about 750 mM to about 1000 mM NaCl and at least about 50% (w/w) glycerol at a pH of at least about 8.0.

20. The method of claim 1, wherein eluting comprises contacting the affinity resin with an elution buffer comprising about 2 mM magnesium chloride, about 50 mM Taurine, about 600 mM to about 1000 mM NaCl, about 0.05 to about 0.2% octylglycopyranoside, and about 60% (w/w) ethylene glycol at a pH of at least about 7.8.

21. The method of claim 1, wherein eluting comprises contacting the affinity resin with an elution buffer comprising about 20% (w/w) sucrose, about 10% (w/w) sorbitol, about 5% (w/w) mannitol or about 5% (w/w) sucrose, about 15% (w/w) glycerol, about 50 mM Histidine, and about 750 mM to about 1000 mM NaCl at a pH of at least about 7.8.

22. The method of claim 1, wherein eluting comprises contacting the affinity resin with an elution buffer comprising about 100 mM Glycine-HCl, about 200 mM NaCl, at a pH of about 2.5.

23. The method of claim 1, wherein eluting comprises applying a gradient of 0 to 100% 20-50 mM Hydrochloric acid/800-1200 mM NaCl in 0.5-2.0 mM Hydrochloric acid.

24. The method of any one of claim 1, wherein
(a) the AAV is AAV8, the affinity resin is an AAV8 affinity matrix, and wherein eluting comprises contacting the affinity resin with an elution buffer and the elution buffer is acidic and does not comprise ethylene glycol;
(b) the AAV is AAV9, the affinity resin is an AAV9 affinity matrix, and wherein eluting comprises contacting the affinity resin with an elution buffer and the elution buffer is acidic and does not comprise ethylene glycol;
(c) the AAV is AAV8, and wherein the affinity resin is an immune affinity resin consisting of an immobilized monoclonal antibody against AAV8 from type ADK8 or ADK8/9 immobilized on a chromatography matrix; or
(d) the AAV is AAV9, and wherein the affinity resin is an immune affinity resin consisting of an immobilized monoclonal antibody against AAV9 from type ADK9 or ADK8/9 immobilized on a chromatography matrix.

25. The method of claim 5, wherein the third wash step comprises applying to the affinity resin a third buffer comprising from about 30 to about 200 mM TrisHCl and from about 30 to about 75 vol % ethylene glycol, and wherein the third buffer has a pH from about 7.3 to about 8.8.

26. The method of claim 5, wherein a third wash step comprises applying to the affinity resin purified water.

27. The method of claim 1, wherein eluting comprises contacting the affinity resin with an elution buffer comprising about 1 mM HCl in purified water, at a pH of about 3.2.

28. The method of claim 1, wherein eluting comprises contacting the affinity resin with an elution buffer comprising from about 30 to about 70 mM TrisHCl, from about 700 mM to about 900 mM NaCl, and from 40% to 60% (w/w) DMSO, at a pH of about 7.5 to about 8.5.

29. The method of claim 1, wherein eluting comprises contacting the affinity resin with an elution buffer comprising about 2M $MgCl_2$, about 50 mM TrisHCl, at a pH of about 7.4.

* * * * *